(12) United States Patent
Bergmann et al.

(10) Patent No.: US 9,229,013 B2
(45) Date of Patent: Jan. 5, 2016

(54) VASOACTIVE HORMONE-BASED STRATIFICATION OF PATIENTS SUFFERING FROM DISEASES RELATED TO ENDOTHELIAL FUNCTION/DYSFUNCTION

(75) Inventors: Andreas Bergmann, Berlin (DE); Joachim Struck, Berlin (DE); Oliver Hartmann, Berlin (DE); Leong Loke Ng, Leicester (GB)

(73) Assignee: B.R.A.H.M.S GMBH, Henningsdorf (DE)

(*) Notice: Subject to any disclaimer, the term of this patent is extended or adjusted under 35 U.S.C. 154(b) by 1013 days.

(21) Appl. No.: 13/318,488

(22) PCT Filed: May 5, 2010

(86) PCT No.: PCT/EP2010/056081
§ 371 (c)(1),
(2), (4) Date: Feb. 8, 2012

(87) PCT Pub. No.: WO2010/128071
PCT Pub. Date: Nov. 11, 2010

(65) Prior Publication Data
US 2012/0142120 A1 Jun. 7, 2012

(30) Foreign Application Priority Data

May 5, 2009 (EP) .................... 09159472
Jun. 19, 2009 (EP) .................... 09163269
Dec. 30, 2009 (EP) .................... 09016143

(51) Int. Cl.
G01N 31/00 (2006.01)
G01N 33/53 (2006.01)
G01N 33/74 (2006.01)

(52) U.S. Cl.
CPC ........ *G01N 33/74* (2013.01); *G01N 2333/5754* (2013.01); *G01N 2333/5757* (2013.01); *G01N 2333/58* (2013.01); *G01N 2800/52* (2013.01)

(58) Field of Classification Search
CPC ............... G01N 2333/575; G01N 2333/5754; G01N 2333/5757; G01N 2800/325
See application file for complete search history.

(56) References Cited

U.S. PATENT DOCUMENTS 7,915,002 B2 * 3/2011 Bergmann .................... 435/7.1

FOREIGN PATENT DOCUMENTS

DE 10 2006 060 835 A1 6/2008
DE 10 2007 010 834 A1 9/2008

OTHER PUBLICATIONS

International Search Report of PCT/EP2010/056081 (Jun. 10, 2010).
Written Opinion of the International Searching Authority of PCT/EP2010/056081 (Jun. 10, 2010).
S. Von Haehling et al., "Comparison of Midregional Pro-Atrial Natriuretic Peptide With N-Terminal Pro-B-Type Natriuretic Peptide in Predicting Survival in Patients with Chronic Heart Failure", Journal of the American College of Cardiology, vol. 50, No. 20 (Oct. 29, 2007) pp. 1973-1980.
A. Gegenhuber et al., "Comparative Evaluation of B-Type Natriuretic Peptide, Mid-Regional Pro-A-Type Natriuretic Peptide, Mid-Regional Pro-Adrenomedullin, and Copeptin to Predict 1-Year Mortality in Patients with Acute Destabilized Heart Failure", Journal of Cardiac Failure, vol. 13, No. 1 (Mar. 3, 2007) pp. 42-49.
S. Q. Khan et al., "C-Terminal Provasopressin (Copeptin) as a Novel and Prognostic Marker in Acute Myocardial Infarction Leicester Acute Myocardial Infarction Peptide (LAMP) Study", Circulation, vol. 115, No. 16 (Apr. 1, 2007) pp. 2103-2110.

* cited by examiner

*Primary Examiner* — Lisa Cook
(74) *Attorney, Agent, or Firm* — Miller, White, Zelano, Branigan, P.C.

(57) ABSTRACT

The present invention relates to a method for the stratification of a subject having an acute or a chronic disease, wherein the disease affects endothelial function/dysfunction, comprising the steps of (i) taking a sample of bodily fluid from the subject; (ii) determining in the sample of bodily fluid the concentration of a vasoactive hormone or fragments thereof or precursors or fragments thereof having a length of at least 12 amino acid residues; (iii) stratifying the subjects into either of the categories: (a) responder to a medication for treatment of the disease, (b) non-responder to a medication for treatment of the disease not showing an unfavorable effect after having received the medication; (c) subjects showing an unfavorable effect after having received the medication. The invention also relates to the use of an antibody or a functional fragment thereof in the method according to the invention.

17 Claims, 34 Drawing Sheets

VASOACTIVE HORMONE-BASED STRATIFICATION OF PATIENTS SUFFERING FROM DISEASES RELATED TO ENDOTHELIAL FUNCTION/DYSFUNCTION

The instant application contains a Sequence Listing which has been submitted electronically in ASCII format and is hereby incorporated by reference in its entirety. Said ASCII copy, created on May 18, 2015, is named BOEHMERP-0114_SL.txt and is 20,991 bytes in size.

FIELD OF THE INVENTION

The present invention is in the field of clinical diagnostics. Particularly the present invention relates to the determination of the concentration of vasoactive hormones and their precursors and fragments thereof in a sample derived from a bodily fluid of a patient and the stratification of patients suffering from a disease related to endothelial function/dysfunction.

BACKGROUND OF THE INVENTION

Increased BNP and NT-proBNP blood concentrations are associated with the severity and mortality in heart failure (HF) patients. In several studies the titration of drug treatment to reduce NT-proBNP levels in patients suffering from HF was investigated (Wasywich, et al. *Changes in tissue-Doppler echocardiographic assessment of left ventricular filling during NT-proBNP guided heart failure treatment titration: a pilot study. Heart Lung and Circulation* 2009; 18:38-44; Mant, et al. *Identification and guided treatment of ventricular dysfunction in general practice using blood B-type natriuretic peptide. British Journal of General Practice* 2008; 58:393-9; Davis, et al. *Introduction of metoprolol increases plasma B-type cardiac natriuretic peptides in mild, stable heart failure. Circulation* 2006; 113:977-85, Beck-da-Silva, et al. *BNP-guided therapy not better than expert's clinical assessment for beta-blocker titration in patients with heart failure. Congestive Heart Failure* 2005; 11:248-53; quiz 254-5).

It has been investigated whether vasoactive biomarkers and their precursors and fragments thereof stratify patients exhibiting a positive effect due to a specific medication. For example, the use of NT-proBNP for stratification of HF patients for medication was presented in the PRIMA-Study at the ACC Congress Orlando (29 Mar. 2009). Moreover, the utility of NT-proBNP measurements to identify patients with enhanced benefit from clopidogrel therapy was investigated by Tang et al., but no NT-proBNP subgroup could be identified with an overproportional benefit from clopidogrel therapy (Tang et al. *Risk stratification for patients undergoing nonurgent percutaneous coronary intervention using N-terminal pro-B-type natriuretic peptide: a Clopidogrel for the Reduction of Events During Observation (CREDO) substudy. American Heart Journal* 2007; 153:36-41). Kropp et al. hypothesized that NT-proBNP could be used as a marker for the tolerability and safety of antipsychotic drugs. (Kropp, et al. *N-terminal fragment of B-type natriuretic peptide (NT-proBNP), a marker of cardiac safety during antipsychotic treatment. Annals of General Psychiatry* 2005; 4:10). In addition, it has been contemplated that other neuroendocrine markers, e.g. AVP, ET-1, Big-ET-1, [NT-pro]ANP and [NT-pro]BNP, may be of value in the choice and titration of medical treatment for an individual patient in the future (Kjaer 2000; *Videnskab og Praksis* 162:5910-3). For example, it has been shown that elevated ANP levels before treatment with the beta-blocker carvedilol are predictive for reductions of mortality, and ANP and BNP are predictive for reductions of hospital admission in patients with chronic stable heart failure (Richards et al. *Neurohumoral prediction of benefit from carvedilol in ischemic left ventricular dysfunction. Australia-New Zealand Heart Failure Group. Circulation* 1999; 99:786-92). In contrast to the cardiac peptides, higher plasma levels of Arg-Vasopressin (AVP) did not predict benefit from carvedilol in this study. In addition the same study group revealed, that carvedilol reduced mortality and heart failure in patients with chronic ischemic left ventricular dysfunction exhibiting a higher pre-treatment plasma NT-proBNP and adrenomedullin (ADM) (Richards et al. *Plasma N-terminal pro-brain natriuretic peptide and adrenomedullin—prognostic utility and prediction of benefit from carvedilol in chronic ischemic left ventricular dysfunction. Journal of the American College of Cardiology* 2001; 37:1781-7). However, patients were stratified according to peptide concentrations below and above median and a beneficial effect of carvedilol was not apparent until 300 days after treatment initiation, indicating that elevated plasma levels of the measured peptides may only predict a long-term benefit of the Beta-blocker carvedilol. Swedberg et al. demonstrated, that markedly elevated levels of ANP before ACE inhibitor treatment (namely elanapril) were related to reductions in mortality levels in patients with severe congestive heart failure in NYHA class IV (Swedberg et al. *Hormones regulating cardiovascular function in patients with severe congestive heart failure and their relation to mortality. CONSENSUS Trial study group. Circulation* 1990; 82:1730-6). Again, patients were stratified according to peptide concentrations below and above median in this study. A beneficial effect of elanapril was demonstrated for mortality after 6 months.

In the patent application WO 2009/123730 methods for diagnosis and prognosis of pulmonary hypertension are described. A variety of markers has been suggested.

DESCRIPTION OF THE INVENTION

The present invention is based on the surprising finding of the inventors that the levels of vasoactive hormones and their precursors and fragments thereof in samples of bodily fluids do not only correlate with a prognosis or diagnosis for a variety of diseases but can also be used to stratify patients into risk groups with respect to certain medications. In other words, the inventors have found that certain populations of patients exist for which the administration of particular medications has no effect on their outcome or even has an adverse (i.e. unfavourable) effect, e.g. a higher mortality as compared to patients that did not receive said medication. Such groups of patients can be identified with the methods of the present invention. This enables to avoid unnecessary or even harmful medications. Thus, one important object of the present methods of stratification is to avoid medication which is harmful to the patient.

In the context of the present invention vasoactive hormones are molecules, e.g. peptides, causing constriction or dilation of blood vessels.

Vasoactive hormones, in particular vasoactive peptides, are unstable in bodily fluids like blood, urine or cerebrospinal fluid. Therefore, direct measurement of vasoactive peptides in bodily fluids is challenging. However, the precursors or precursor fragments of vasoactive peptides are more stable than the mature hormones, and their measurement can be used as a substitute or surrogate measurement for the mature vasoactive peptides. This has already been shown for a number of vasoactive peptides e.g. insulin and its stable precursor fragment C-peptide (Melani et al. *Identification of proinsulin and C-peptide in human serum by a specific immunoassay.*

PNAS 1970; 67:148-55), Arginine-Vasopressin and its stable precursor fragment copeptin (Struck et al. *Copeptin, a stable peptide derived from the vasopressin precursor, is elevated in serum of sepsis patients. Peptides* 2005; 25:2500-4; Morgenthaler et al. *Assay for the measurement of copeptin, astable peptide derived from the precursor of vasopressin. Clinical Chemistry* 2006; 52:112-9), adrenomedullin and its stable precursor fragment MR-proADM (Struck et al. *Identification of an adrenomedullin precursor fragment in plasma of sepsis patients. Peptides* 2004; 25:1369-72; Morgenthaler et al. *Measurement of midregional proadrenomedullin in plasma with an immunoluminometric assay. Clinical Chemistry* 2005; 51:1823-9), atrial natriuretic peptide and its stable precursor fragment MR-proANP (Morgenthaler et al. *Immunoluminometric assay for the midregion of pro-atrial natriuretic peptide in human plasma. Clinical Chemistry* 2004; 50:234-6), endothelin-1 and its stable precursor fragment CT-proET-1 (Struck et al. *Proteolytic processing pattern of the endothelin-1 precursor in vivo. Peptides* 2005; 26:2482-6; Papassotiriou et al. *Immunoluminometric assay for the measurement of the C-terminal endothelin-1 precursor fragment in human plasma. Clinical Chemistry* 2006; 52:1144-51), the enkephalins and their stable precursor fragment MR-PENK (Ernst et al. *Proenkephalin A 119-159, a stable proenkephalin A precursor fragment identified in human circulation. Peptides* 2006; 27:1835-40), the mature tachykinins substance P and neurokinin A and their stable precursor fragment NT-PTA (Ernst et al. *Detection of a stable N-terminal protachykinin A immunoreactivity in human plasma and cerebrospinal fluid. Peptides* 2008; 29:1201-6), neurotensin and its stable precursor fragment proneurotensin 1-117 (Ernst et al. *Proneurotensin 1-117, a stable neurotensin precursor fragment identified in human circulation. Peptides* 2006; 27:1787-93).

Endothelial dysfunction is a physiological dysfunction of normal biochemical processes carried out by the endothelium, the cells lining the inner surface of blood vessels. Endothelial dysfunction is characterized by an impaired vasodilation (imbalance between relaxing and contracting factors) as well as changes in the proinflammatory state and prothrombic properties (Endemann and Schiffrin, *Endothelial Dysfunction. Journal American Society of Nephrology* 2004; 15:1983-92). It is associated with cardiovascular diseases, such as hypertension, coronary artery disease, heart failure, peripheral artery disease, diabetes, and chronic renal failure. Moreover, endothelial dysfunction is thought to be a key event in the development of atherosclerosis and predates clinically obvious vascular pathology by many years. Endothelial dysfunction has also been shown to be of prognostic significance in predicting vascular events including stroke and myocardial infarctions. In addition, endothelial dysfunction was shown to be implicated in inflammation and infection (Stenvinkel. *Endothelial dysfunction and inflammation—is there a link? Nephrology Dialysis and Transplantation* 2001; 16:1968-71), sepsis (Vallet. *Bench-to-bedside review: Endothelial cell dysfunction in severe sepsis: a role in organ dysfunction? Critical Care* 2003; 7:130-8; Peters et al. *Molecular basis of endothelial dysfunction in sepsis. Cardiovascular Research* 2003; 60:49-57) as well as COPD (Moro. *Endothelial dysfunction in chronic obstructive pulmonary disease. Angiology* 2008; 59:357-64).

Thus, the present invention pertains to a method for the stratification of a subject having an acute or a chronic disease, wherein said disease effects endothelial function/dysfunction, comprising the steps of:
 taking a sample of bodily fluid from said subject;
 determining in said sample of bodily fluid the concentration of a vasoactive hormone or fragments thereof or precursors or fragments thereof having a length of at least 12 amino acids;
 stratifying said subjects into one of the following categories:
  (i) responder to a medication for treatment of said disease,
  (ii) non-responder to a medication for treatment of said disease not showing an unfavourable effect after having received said medication;
  (iii) subjects showing an unfavourable effect after having received said medication.

In one embodiment the methods of the present invention comprise the provision of a system comprising the three categories (i), (ii) and (iii). In an even more preferred embodiment the methods of the present invention comprise the provision of at least two thresholds that are used in order to establish said system comprising and/or consisting of the three categories (i), (ii) and (iii).

In the context of the present invention the term "responder" refers to a subject showing a favourable effect after having received a medication for treatment of a disease.

The term "non-responder" in the context of the present invention refers to a subject showing no effect (neither a favourable nor an unfavourable effect) after having received a medication for treatment of a disease.

In some embodiments according to the invention, categories (i) and (ii) are pooled and distinguished from category (iii), i.e. the subjects are stratified into subjects showing an unfavourable effect and subjects not showing an unfavourable effect.

In this embodiment the methods of the present invention comprise the provision of a system comprising and/or consisting of two categories. In an even more preferred embodiment this includes the provision of at least one threshold that is used to establish said two-categories-system. The ultimate object the two-categories-system is the prevention of harm by medications.

The invention also relates to a method for the stratification of a subject having an acute or a chronic disease, wherein said disease effects endothelial function/dysfunction, comprising the steps of:
 taking a sample of bodily fluid from said subject;
 determining in said sample of bodily fluid the concentration of a vasoactive hormone or fragments thereof or precursors or fragments thereof having a length of at least 12 amino acid residues;
 stratifying said subjects into one of the following categories:
  (i) responder or non-responder to a medication for treatment of said disease not showing an unfavourable effect after having received said medication;
  (ii) subjects showing an unfavourable effect after having received said medication.

In a particular aspect the present invention also relates to a method for the stratification of a subject having an acute or a chronic disease, wherein said disease affects endothelial function/dysfunction, comprising the steps of:
 taking a sample of bodily fluid from said subject;
 determining in said sample of bodily fluid the concentration of a vasoactive hormone or fragments thereof or precursors or fragments thereof having a length of at least 12 amino acid residues;
 attributing the concentration of the vasoactive hormone or fragments thereof or precursors or fragments thereof in the sample to a risk of the subject of experiencing an unfavourable effect after receiving a particular medication.

"Subjects showing an unfavourable effect after having received said medication" in the context of the present invention are subjects which are expected to experience an unfavourable effect upon administration of said medication.

Preferably herein, the vasoactive hormone is:
(i) a peptide hormone selected from the group consisting of Adrenomedullin (ADM), Atrial Natriuretic Peptide (ANP), Brain natriuretic peptide (BNP), C-type natriuretic peptide (CNP), Endothelin-1, Endothelin-2, Endothelin-3, Arginine-Vasopressin (AVP), Dendroaspis natriuretic peptide (DNP), Urodilatin, Angiotensin II, Urocortin, Urocortin-2 (Stresscopin-related peptide), Urocortin-3 (Stresscopin), Urotensin-II, Urotensin II-related protein (URP), Neuropeptide Y (NPY), Vasoactive intestinal peptide (VIP), Calcitonin gene-related peptide I (CGRP I) and Calcitonin gene-related peptide II (CGRP II), Insulin, Proenkephalin (PENK), Endokinin A, Dynorphin, Ghrelin, Relaxin or fragments thereof or precursors or fragments thereof having a length of at least 12 amino acid residues or
(ii) a small peptide hormone selected from the group consisting of Bradykinin, Apelin, Neurotensin, Substance P, Neurokinin A (Substance K), Endokinin A/B, Endokinin C, Methionine-Enkephalin, Leucine-Enkephalin, or fragments thereof or precursors or fragments thereof having a length of at least 12 amino acid residues or
(iii) a hormone selected from the group consisting of Serotonin, Prostaglandins and Thromboxane.

More preferably herein, the vasoactive hormone is:
(i) a peptide hormone selected from the group consisting of Adrenomedullin (ADM), Atrial Natriuretic Peptide (ANP), Brain natriuretic peptide (BNP), C-type natriuretic peptide (CNP), Endothelin-1, Endothelin-2, Endothelin-3, Arginine-Vasopressin (AVP), Dendroaspis natriuretic peptide (DNP), Urodilatin, Angiotensin II, Urocortin, Urocortin-2 (Stresscopin-related peptide), Urocortin-3 (Stresscopin), Urotensin-II, Urotensin II-related protein (URP), Neuropeptide Y (NPY), Vasoactive intestinal peptide (VIP), Calcitonin gene-related peptide I (CGRP I) and Calcitonin gene-related peptide II (CGRP II), Endokinin A, Relaxin or fragments thereof or precursors or fragments thereof having a length of at least 12 amino acid residues or
(ii) a small peptide hormone selected from the group consisting of Bradykinin, Apelin, Neurotensin, Substance P, Neurokinin A (Substance K), Endokinin A/B, Endokinin C, Methionine-Enkephalin, Leucine-Enkephalin, or fragments thereof or precursors or fragments thereof having a length of at least 12 amino acid residues or
(iii) a hormone selected from the group consisting of Serotonin, Prostaglandins and Thromboxane.

"Small" peptide hormones in the context of the present invention are peptide hormones comprising 13 or less amino acid residues, in particular Bradykinin, Apelin, Neurotensin, Substance P, Neurokinin A (Substance K), Methionine-Enkephalin and Leucine-Enkephalin.

Proenkephalin (PENK) is the precursor polypeptide of Methionine-Enkephalin and Leucine-Enkephalin.

In one particularly preferred embodiment the precursor fragment of the vasoactive hormone ADM is Midregional pro-Adrenomedullin (MR-proADM) or a fragment thereof having a length of at least 12 amino acid residues.

In another particularly preferred embodiment the precursor fragment of the vasoactive hormone ANP is Midregional pro-Atrial Natriuretic Peptide (MR-proANP) or a fragment thereof having a length of at least 12 amino acid residues.

In yet another particularly preferred embodiment the precursor fragment of the vasoactive hormone ET-1 is C-terminal pro-Endothelin-1 (CT-proET-1) or a fragment thereof having a length of at least 12 amino acid residues.

In yet another particularly preferred embodiment the precursor fragment of the vasoactive hormone AVP is C-terminal pro-AVP (Copeptin) or a fragment thereof having a length of at least 12 amino acid residues.

The disease may, e.g., be selected from the group consisting of: chronic heart failure, shortness of breath (SOB), acute coronary syndrome, acute heart failure (AHF), arrhythmia, asthma exacerbation, bronchitis, chest pain, influenza, chronic obstructive pulmonary disease (COPD), pneumonia and pulmonary embolism, pulmonary arterial hypertension (PAH), post stroke condition, post myocardial infarct condition, diabetes type II, cancer, atherosclerosis, infections, inflammatory diseases, and post surgery condition.

The disease may, e.g., be selected from the group consisting of: chronic heart failure, shortness of breath (SOB), acute coronary syndrome, acute heart failure (AHF), arrhythmia, asthma exacerbation, bronchitis, chest pain, influenza, chronic obstructive pulmonary disease (COPD), pneumonia and pulmonary embolism, post stroke condition, post myocardial infarct condition, diabetes type II, cancer, atherosclerosis, infections, inflammatory diseases, and post surgery condition.

In one particularly preferred embodiment, the disease is selected from the group consisting of shortness of breath (SOB), acute coronary syndrome, acute heart failure (AHF), arrhythmia, asthma exacerbation, bronchitis, chest pain, influenza, chronic obstructive pulmonary disease (COPD), pneumonia and pulmonary embolism and pulmonary arterial hypertension (PAH).

In one particularly preferred embodiment, the disease is selected from the group consisting of shortness of breath (SOB), acute coronary syndrome, acute heart failure (AHF), arrhythmia, asthma exacerbation, bronchitis, chest pain, influenza, chronic obstructive pulmonary disease (COPD), pneumonia and pulmonary embolism.

In another particularly preferred embodiment, the disease is a post stroke condition, i.e. is related to subjects having suffered from ischemic or haemorrhagic stroke or transient ischemic attack (TIA).

Heart failure (HF), also termed congestive heart failure (CHF) is a cardiac condition that occurs when a problem with the structure or function of the heart impairs its ability to supply sufficient blood flow to meet the body's needs. Chronic heart failure is a long term situation, usually with stable treated symptomatology. Acute heart failure is a term used to describe exacerbated or decompensated heart failure, referring to episodes in which a patient can be characterized as having a change in heart failure signs and symptoms resulting in a need for urgent therapy or hospitalization.

Shortness of breath (SoB; also known as dyspnea or difficulty breathing) relates to a sensation of difficult or uncomfortable breathing or a feeling of not getting enough air in a subject. SoB may have many different causes, among them heart diseases such as heart attack, congestive heart failure, and pulmonary diseases (incl. pneumonia).

Acute coronary syndrome is an umbrella term used to cover any group of clinical symptoms compatible with acute myocardial ischemia. Acute myocardial ischemia is chest pain due to insufficient blood supply to the heart muscle that results from coronary artery disease (also called coronary heart disease). An acute coronary syndrome (ACS) is a set of signs and symptoms, usually a combination of chest pain and other features, interpreted as being the result of abruptly decreased blood flow to the heart (cardiac ischemia); the most common cause for this is the disruption of atherosclerotic plaque in an epicardial coronary artery. The subtypes of acute coronary syndrome include unstable angina (UA, not associated with heart muscle damage), and two forms of myocardial infarction (heart attack), in which heart muscle is damaged. These types are named according to the appearance of the electrocardiogram (ECG/EKG) as non-ST segment elevation myocardial infarction (NSTEMI) and ST segment elevation myocardial infarction (STEMI).

Arrhythmia is a term for any of a large and heterogeneous group of conditions in which there is abnormal electrical activity in the heart. The heart beat may be too fast or too slow, and may be regular or irregular. Some arrhythmias are life-threatening medical emergencies that can result in cardiac arrest and sudden death. Others cause symptoms such as an abnormal awareness of heart beat (palpitations), and may be merely annoying. These palpitations have also been known to be caused by atrial/ventricular fibrillation, wire faults, and other technical or mechanical issues in cardiac pacemakers/defibrillators. Still others may not be associated with any symptoms at all, but may predispose the patient to potentially life threatening stroke or embolism.

Asthma is a common chronic inflammatory disease of the airways characterized by variable and recurring symptoms, airflow obstruction, and bronchospasm. Symptoms include wheezing, cough, chest tightness, and shortness of breath. Some individuals will have stable asthma for weeks or months and then suddenly develop an episode of acute asthma. Different asthmatic individuals react differently to various factors. However, most individuals can develop severe exacerbation of asthma from several triggering agents.

Bronchitis is inflammation of the mucous membranes of the bronchi, the airways that carry airflow from the trachea into the lungs. Bronchitis can be classified into two categories, acute and chronic, each of which has unique etiologies, pathologies, and therapies. Acute bronchitis is characterized by the development of a cough, with or without the production of sputum, mucus that is expectorated (coughed up) from the respiratory tract. Acute bronchitis often occurs during the course of an acute viral illness such as the common cold or influenza. Viruses cause about 90% of cases of acute bronchitis while bacteria account for less than 10%. Chronic bronchitis, a type of chronic obstructive pulmonary disease, is characterized by the presence of a productive cough that lasts for 3 months or more per year for at least 2 years. Chronic bronchitis most often develops due to recurrent injury to the airways caused by inhaled irritants. Cigarette smoking is the most common cause, followed by air pollution and occupational exposure to irritants, and cold air.

Chronic obstructive pulmonary disease (COPD) refers to chronic bronchitis and emphysema, a pair of two commonly co-existing diseases of the lungs in which the airways become narrowed. This leads to a limitation of the flow of air to and from the lungs causing shortness of breath. In contrast to asthma, the limitation of airflow is poorly reversible and usually gets progressively worse over time. COPD is caused by noxious particles or gas, most commonly from tobacco smoking, which triggers an abnormal inflammatory response in the lung. The inflammatory response in the larger airways is known as chronic bronchitis, which is diagnosed clinically when people regularly cough up sputum. In the alveoli, the inflammatory response causes destruction of the tissues of the lung, a process known as emphysema. The natural course of COPD is characterized by occasional sudden worsenings of symptoms called acute exacerbations, most of which are caused by infections or air pollution.

Pneumonia is an abnormal inflammatory condition of the lung. It is often characterized as including inflammation of the parenchyma of the lung (that is, the alveoli) and abnormal alveolar filling with fluid (consolidation and exudation). The alveoli are microscopic air-filled sacs in the lungs responsible for gas exchange. Pneumonia can result from a variety of causes, including infection with bacteria, viruses, fungi, or parasites, and chemical or physical injury to the lungs. Its cause may also be officially described as idiopathic—that is, unknown—when infectious causes have been excluded. Typical symptoms associated with pneumonia include cough, chest pain, fever, and difficulty in breathing. Diagnostic tools include x-rays and examination of the sputum. Treatment depends on the cause of pneumonia; bacterial pneumonia is treated with antibiotics. Pneumonia is a common illness which occurs in all age groups, and is a leading cause of death among the elderly and people who are chronically and terminally ill. Additionally, it is the leading cause of death in children under five years old worldwide.

Pulmonary embolism (PE) is a blockage of the main artery of the lung or one of its branches by a substance that has traveled from elsewhere in the body through the bloodstream (embolism). Usually this is due to embolism of a thrombus (blood clot) from the deep veins in the legs, a process termed venous thromboembolism. A small proportion is due to the embolization of air, fat or amniotic fluid. The obstruction of the blood flow through the lungs and the resultant pressure on the right ventricle of the heart leads to the symptoms and signs of PE. The risk of PE is increased in various situations, such as cancer and prolonged bed rest. Symptoms of pulmonary embolism include difficulty breathing, chest pain on inspiration, and palpitations. Clinical signs include low blood oxygen saturation and cyanosis, rapid breathing, and a rapid heart rate. Severe cases of PE can lead to collapse, abnormally low blood pressure, and sudden death.

Pulmonary arterial hypertension (PAH) is a syndrome characterised by a progressive increase in pulmonary vascular resistance leading to right ventricular overload and eventually to right ventricular failure and premature death. Pulmonary Arterial Hypertension (PAH) is defined as a sustained elevation of mean pulmonary arterial pressure to more than 25 mmHg at rest or to more than 30 mmHg while exercising, with a normal pulmonary wedge pressure (<15 mmHg). In most cases the earliest symptom is dyspnea on physical exertion. Other symptoms include syncope or near syncope, fatigue and peripheral oedema. Chest tightness and pain similar to angina may occur, particularly on physical exertion.

Stroke is defined as an acute focal neurological deficit resulting from a cerebrovascular disease. The two main types of stroke are ischemic and hemorrhagic, accounting for approximately 85% and 15%, respectively (Hickey 2003. *The clinical practice of neurological and neurosurgical nursing* (5$^{th}$ ed.). Philadelphia: Lippincott, Williams & Wilkins). When an ischemic stroke occurs, the blood supply to the brain is interrupted, and brain cells are deprived of glucose and oxygen. Approximately 45% of ischemic strokes are caused by small or large artery thrombus, 20% are embolic origin, and others have an unknown cause (Hickey 2003. *The clinical practice of neurological and neurosurgical nursing* (5$^{th}$ ed.). Philadelphia: Lippincott, Williams & Wilkins).

Transient ischemic attack (TIA) (also known as "mini-stroke") is a syndrome characterized by the sudden onset of discrete neurological symptoms that resolve completely within 24 hours. TIA may be reported by 0.5-8% of the elderly population (Bots et al., 1997. *Stroke* 28(4): 768-73). A patient representing with a TIA is at high risk of subsequent adverse events. The 90-day risk of stroke has been reported to be greater than 10%, with the highest risk occurring within the first 2 days (Jonston et al., 2003. *Neurology* 60: 1429-34).

Myocardial infarction (MI) or acute myocardial infarction (AMI), commonly known as a heart attack, is the interruption of blood supply to part of the heart, causing some heart cells to die. This is most commonly due to occlusion (blockage) of a coronary artery following the rupture of a vulnerable atherosclerotic plaque, which is an unstable collection of lipids (fatty acids) and white blood cells (especially macrophages) in the wall of an artery. The resulting ischemia (restriction in blood supply) and oxygen shortage, if left untreated for a sufficient period of time, can cause damage or death (infarction) of heart muscle tissue (myocardium). On the basis of the ECG, a distinction is made between ST elevation MI (STEMI) or non-ST elevation MI (non-STEMI).

Diabetes mellitus type 2 or type 2 diabetes (formerly called non-insulin-dependent diabetes mellitus (NIDDM), or adult-onset diabetes) is a disorder that is characterized by high blood glucose in the context of insulin resistance and relative insulin deficiency.

Atherosclerosis (also known as arteriosclerotic vascular disease or ASVD) is the condition in which an artery wall thickens as the result of a build-up of fatty materials such as cholesterol. It is a syndrome affecting arterial blood vessels, a chronic inflammatory response in the walls of arteries, in large part due to the accumulation of macrophage white blood cells and promoted by low-density lipoproteins (plasma proteins that carry cholesterol and triglycerides) without adequate removal of fats and cholesterol from the macrophages by functional high density lipoproteins (HDL). It is commonly referred to as a hardening or furring of the arteries. It is caused by the formation of multiple plaques within the arteries.

In another particularly preferred embodiment, the disease is a post myocardial infarct condition, i.e. subjects having suffered a myocardial infarction.

Accordingly, the medication may, for example, be selected from the group consisting of anti-coagulant, thrombolytic drugs, platelet aggregation inhibitor, β-blocker, anti-oxidant, lipid lowering substance, diuretic, ACE (Angiotensin-Converting Enzyme) inhibitor, calcium channel blocker, endothelin-receptor antagonists, phosphodiesterase type 5 inhibitors, prostacyclin derivatives, soluble guanylate cyclise activators, hormone therapeutic agent, NO substituent, adenosine receptor blocker, cardiac glycoside, angiotensin-II antagonist, anti-diabetic drug, antiarrhythmic and antibiotic. Particularly preferred medications are ACE inhibitors, diuretics and β-blockers.

Accordingly, the medication may, for example, be selected from the group consisting of anti-coagulant, thrombolytic drugs, platelet aggregation inhibitor, β-blocker, anti-oxidant, lipid lowering substance, diuretic, ACE (Angiotensin-Converting Enzyme) inhibitor, calcium channel blocker, hormone therapeutic agent, NO substituent, adenosine receptor blocker, cardiac glycoside, angiotensin-II antagonist, anti-diabetic drug, antiarrhythmic and antibiotic. Particularly preferred medications are ACE inhibitors, diuretics and β-blockers.

The medication may also be a combination of two or more drugs such as β-blocker/calcium channel blocker (e.g. Belnif®, i.e. active ingredients: metoprolol+nifedipin), angiotensin-II antagonisten/diuretic (e.g. Blopress®—active ingredients: candesartan+hydrochlorothiazid).

The calcium channel blocker may for example be selected from the group consisting of dihydropyridine (e.g. Nicardipine), phenylalkylamine (e.g. Verapamil), Benzothiazepine (e.g. Diltiazem), Mibefradil and Fendiline.

The lipid lowering substance may for example be selected from the group consisting of statin (e.g. Lovastatin, Simvastatin, Pravastatin, Fluvastatin, Cerivastatin, Atorvastatin, Mevastatin, Pitavastatin, Rosuvastatin), Fibrate (e.g. Bezafibrate, Fenofibrate, Etofibrate, Gemfibrozil), bile acid sequestrant (e.g. Cholestyramine, Colestipol) and nicotinic acid derivative (e.g. Acipimox, Xantinol nicotinate, Inositol nicotinate).

The anti-oxidant may for example be selected from the group consisting of vitamin A, vitamin C, Oxypurionol, Superoxide dismutase, and Probucol.

The ACE inhibitor may for example be selected from the group coconsisting of Captopril, Enalapril, Quanalapril, Peridopril, Temocapril, Ramipril, Lisinopril.

The hormone therapeutic agent may for example be selected from the group consisting of β-Estradiol and Progesterone.

The NO substituent may for example be selected from the group consisting of organic nitrates (e.g. nitroglycerine), sydnonimine and L-arginine.

The anti-coagulant may for example be selected from the group consisting of a vitamin K antagonist (e.g. Phenprocoumon, Warfarin), a direct thrombin inhibitor (e.g. Lepirudin, Desirudin, Argatroban), Heparin.

The thrombolytic drug may for example be selected from the group consisting of tissue plasminogen activator (tPA), reteplase, tenecteplase, anistreplase, streptokinase, and urikinase.

The platelet aggregation inhibitor may for example be selected from the group consisting of, Ticlopidin, Clopidogrel, Acetylsalicylic Acid.

The cardiac glycoside may for example be selected from the group consisting of Digoxin, Digitoxin, Deslanoside, Ouabain and Proscillaridin.

The diuretic may for example be selected from the group consisting of a loop diuretic (e.g. Furosemide), a benzothiadiazide diuretic (e.g. Metolazone), a potassium sparing diuretic (e.g. Spironolactone) and an osmotic diuretic (e.g. Mannitol).

The angiotensin-II antagonist may for example be selected from the group consisting of Candesartan, Eprosartan, Irbesartan, Telmisartan, Losartan, Valsartan and Olmesartan.

The β-blocker may for example be selected from the group consisting of a non-selective β-blocker (e.g. Nadolol, Penbutolol), a β1-selective agent (e.g. Bisoprolol, Metoprolol), and a α1/β-adrenergic antagonist (e.g. Carvedilol, Celiprolol).

The endothelin-receptor antagonists may for example be selected from the group consisting of a selective endothelin receptor type A antagonist (e.g. sitaxentan, ambrisentan, atrasentan, BQ-123), a selective endothelin receptor B antagonist (e.g. sarafotoxin B), and a endothelin receptor A/B antagonist (e.g. bosentan, tezosentan).

The phoshodiesterase type 5 inhibitors may for example be selected from the group consisting of sildenafil, sildenfil citrate, avanafil, lodenafil, mirodenafil, tadalafil, vardenafil, udenafil.

The prostacyclin derivatives may for example be selected from the group consisting of epoprostenol, treprostinil, iloprost, beraprost.

The soluble guanylate cyclise activators may for example be selected from the group consisting of cinaciguat, riociguat.

The antiarrhythmic may for example be selected from the group consisting of Chinidin, class I antiarrhythmics (e.g. Disopyramide, Lidocaine, Propafenone), class II antiarrhythmics (e.g. Metoprolol), class III antiarrhythmics (e.g. Amiodarone, Sotalol), class IV antiarrhythmics (e.g. Verapamil, Diltiazem).

The antibiotic may for example be selected from the group consisting of a Penicillin (e.g. Flucloxacillin, Amoxicillin, Ampicillin, Mezlocillin), a Cephalosporine (e.g. Cefazolin, Cefuroxim, Cefotaxim, Cefaclor, Cefalexin), a β-Lactamase Inhibitor (e.g. Sulbactam, Tazobactam), a Tetracycline (e.g. Doxycyclin, Minocyclin, Tetracyclin, Oxytetracyclin), an Aminoglycoside (e.g. Gentamicin, Neomycin, Streptomycin), a Makrolid-Antibiotic (e.g. Azithromycin, Clarithromycin, Erythromycin, Roxithromycin, Spiramycin, Clindamycin), a Lincosamide (e.g. Lincomycin), a Gyrase inhibitor (e.g. Ciprofloxacin, Ofloxacin, Norfloxacin), Sulfonamides, Trimethoprim, a Glycopeptide Antibiotic (e.g. Vancomycin), a polypeptide antibiotic (e.g. Colistin, Polymyxin), an Amphenicole (e.g. Chloramphenicol).

The anti-diabetic drug may for example be selected from the group consisting of insulins, alpha-glucosidase inhibitors, Biguanid derivatives (e.g. Metformin), Sulfonylurea derivatives (e.g. Glibenclamid, Tolbutamid) Pioglitazone, Repaglinid, Nateglinid, and Rosiglitazonemaleat.

In one particularly preferred embodiment of the method according to the present invention the disease is ischemic stroke, the hormone precursor fragment to be determined is MR-proADM or a fragment thereof having a length of at least 12 amino acids and wherein the medication is statin. In this case the patients are preferably stratified into said categories using the following thresholds:
  (i) responder to a medication for treatment of said disease: >0.9 pmol/L MR-proADM
  (ii) non-responder to a medication for treatment of said disease not showing an unfavourable effect after having received said medication: 0.5-0.9 pmol/L MR-proADM.
  (iii) subjects showing an unfavourable effect after having received said medication: <0.5 pmol/L MR-proADM.

In another particularly preferred embodiment of the method according to the present invention the disease is ischemic stroke, the hormone precursor fragment to be determined is MR-proADM or a fragment thereof having a length of at least 12 amino acids and wherein the medication is clopidogrel.

In yet another particularly preferred embodiment of the method according to the present invention the disease is ischemic stroke, the hormone precursor fragment to be determined is CT-proAVP or a fragment thereof having a length of at least 12 amino acids and wherein the medication is acetylsalicylic acid.

In yet another particularly preferred embodiment of the method according to the present invention the disease is ischemic stroke, the hormone precursor fragment to be determined is CT-proAVP or a fragment thereof having a length of at least 12 amino acids and wherein the medication is a diuretics. In this case the patients are preferably stratified into said categories using the following thresholds:
  (i) responder to a medication for treatment of said disease or non-responder to a medication for treatment of said disease not showing an unfavourable effect after having received said medication: <4 pmol/L CT-proAVP.
  (ii) subjects showing an unfavourable effect after having received said medication: >4 pmol/L CT-proAVP.

In yet another particularly preferred embodiment of the method according to the present invention the disease is myocardial infarction, the hormone precursor fragment to be determined is MR-proADM or a fragment thereof having a length of at least 12 amino acids and wherein the medication is a diuretic. In this case the patients are preferably stratified into said categories using the following thresholds:
  (i) responder to a medication for treatment of said disease or non-responder to a medication for treatment of said disease not showing an unfavourable effect after having received said medication: >0.5 pmol/L MR-proADM.
  (ii) subjects showing an unfavourable effect after having received said medication: <0.5 pmol/L MR-proADM.

In yet another particularly preferred embodiment of the method according to the present invention the disease is post-myocardial infarction condition, the hormone precursor fragment to be determined is CT-proAVP or a fragment thereof having a length of at least 12 amino acids and wherein the medication is an ACE inhibitor/adenosine receptor blocker (ARB). In this case the patients are preferably stratified into said categories using the following thresholds:
  (i) responder to a medication for treatment of said disease: >19 pmol/L CT-proAVP
  (ii) non-responder to a medication for treatment of said disease not showing an unfavourable effect after having received said medication: 3.6-19 pmol/L CT-proAVP.
  (iii) subjects showing an unfavourable effect after having received said medication: <3.6 pmol/L CT-proAVP.

The threshold values cited herein above are to be understood as values for very particular, illustrative embodiments.

The unfavourable effect herein may e.g. be death or major adverse cardiac event (MACE). The outcome in terms of an unfavourable effect may be at a given time after entry of the patients into treatment, e.g. after admission in the emergency department. The outcome may be after several days, several weeks, several months or several years, e.g. 1, 2, 3, 4, 5, 6, 7, 8, 9, 10, 11 or 12 weeks or 1, 2, 3, 4, 5, 6, 7, 8, 9, 10, 11 or 12 months after admission.

The bodily fluid is preferably selected from the group of blood, serum, plasma, cerebrospinal fluid, urine, saliva, sputum, and pleural effusions. More preferably the sample is selected from whole blood, plasma or serum, most preferably the sample is plasma.

The present invention also pertains to the use of an assay for the determination of the concentration of a vasoactive hormone or fragments thereof or precursors or fragments thereof having a length of at least 12 amino acid residues in a sample derived from a bodily fluid of a subject for the stratification of a subject having an acute or a chronic disease, into either of the categories:
  (i) responder to a medication for treatment of said disease,
  (ii) non-responder to a medication for treatment of said disease not showing an unfavourable effect after having received said medication;
  (iii) subjects showing an unfavourable effect after having received said medication,
  (iv) wherein said disease effects endothelial function/dysfunction.

In the context of the present invention also combinations of two or more vasoactive hormone levels or fragments thereof or precursors or fragments thereof having a length of at least 12 amino acid residues can be employed. Furthermore, some subjects according to the present invention may also receive a combination of two or more medications. Also these subjects may be stratified in the context of the present invention.

The invention also relates to the use of an antibody or a functional fragment thereof specific for a vasoactive hormone or fragments thereof or precursors or fragments thereof having a length of at least 12 amino acid residues selected from the group of Adrenomedullin (ADM), Atrial Natriuretic Peptide (ANP), Brain natriuretic peptide (BNP), C-type natriuretic peptide (CNP), Endothelin-1, Endothelin-2, Endothelin-3, Arginine-Vasopressin (AVP), Dendroaspis natriuretic peptide (DNP), Urodilatin, Angiotensin II, Urocortin, Urocortin-2 (Stresscopin-related Ser. No. peptide), Urocortin-3 (Stresscopin), Urotensin-II, Urotensin II-related protein (URP), Neuropeptide Y (NPY), Vasoactive intestinal peptide (VIP), Calcitonin gene-related peptide I (CGRP I), Calcitonin gene-related peptide II (CGRP II), Bradykinin, Relaxin, Apelin, Neurotensin, Substance P, and Neurokinin A (Substance K), Endokinin A, Endokinin A/B, Endokinin C, Methionine-Enkephalin, Leucine-Enkephalin in a method for the stratification of a subject having an acute or a chronic disease, into either of the categories:
(i) responder to a medication for treatment of said disease,
(ii) non-responder to a medication for treatment of said disease not showing an unfavourable effect after having received said medication;
(iii) subjects showing an unfavourable effect after having received said medication,
wherein said disease effects endothelial function/dysfunction.

Suitable threshold levels for the stratification of subjects into different groups (categories) have to be determined for each particular combination of vasoactive hormone or fragments thereof or precursors or fragments thereof, medication and disease. This can e.g. be done by grouping a reference population of patients according to their level of vasoactive hormone into certain quantiles, e.g. tertiles, quartiles, quintiles or even according to suitable percentiles. For each of the quantiles or groups above and below certain percentiles, hazard ratios can be calculated comparing the risk for an adverse outcome, i.e. an "unfavourable effect", e.g. in terms of survival rate, between those patients who have received a certain medication and those who did not. In such a scenario, a hazard ratio (HR) above 1 indicates a higher risk for an adverse outcome for the patients who have received a treatment than for patients who did not. A HR below 1 indicates beneficial effects of a certain treatment in the group of patients. A HR around 1 (e.g. +/−0.1) indicates no elevated risk but also no benefit from medication for the particular group of patients. By comparison of the HR between certain quantiles of patients with each other and with the HR of the overall population of patients, it is possible to identify those quantiles of patients who have an elevated risk and those who benefit from medication and thereby stratify subjects according to the present invention.

In a preferred embodiment of the method according to the present invention, at least two threshold levels of a vasoactive hormone or fragments thereof or precursors or fragments thereof having a length of at least 12 amino acids, have to be determined to stratify said subjects into one of the following categories:
(i) responder to a medication for treatment of said disease,
(ii) non-responder to a medication for treatment of said disease not showing an unfavourable effect after having received said medication;
(iii) subjects showing an unfavourable effect after having received said medication.

In some cases unfavourable effects will affect patients with high levels (e.g. in the fifth quintile) of vasoactive hormones or fragments thereof or precursors or fragments thereof, while in other cases only patients with low levels of vasoactive hormones or fragments thereof or precursors or fragments thereof will be affected (e.g. in the first quintile). This depends on the particular medication, hormone and disease. However, with the above explanations, a skilled person is able to identify those groups of patients for which the medication has an unfavourable effect, those groups that do neither benefit nor suffer from the medication and those groups that benefit from the medication. Exemplarily, some combinations of hormone precursor fragments and medications are listed for several diseases in the appended examples.

In the appended examples, such an analysis of patients groups is demonstrated for patients from various clinical studies that have been treated with a variety of different drugs and for which the levels of various vasoactive hormone precursor fragments has been measured. However, the present invention is not limited to those combinations of medications, diseases and vasoactive hormones or fragments thereof or precursors or fragments thereof demonstrated in the examples, but provides for a more general method.

Determining (or measuring or detecting) the level of a vasoactive peptide hormone or fragment thereof or precursor or fragment thereof (also termed "marker peptide") herein may be performed using a detection method and/or a diagnostic assay as explained below.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8 \, M^{-1}$.

In the context of the present invention, "capture molecules" are molecules which may be used to bind target molecules or molecules of interest, i.e. analytes (i.e. in the context of the present invention the cardiovascular and/or vasoactive peptide(s)), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules may for instance be selected from the group comprising a nucleic acid molecule, a carbohydrate molecule, a RNA molecule, a protein, an antibody, a peptide or a glycoprotein. Preferably, the capture molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

The preferred detection methods comprise immunoassays in various formats such as for instance radioimmunoassay (RIA), chemiluminescence- and fluorescence-immunoassays, Enzyme-linked immunoassays (ELISA), LUMINEX-based bead arrays, protein microarray assays, and rapid test formats such as for instance immunochromatographic strip tests.

The assays can be homogenous or heterogeneous assays, competitive and non-competitive assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person. (*The Immunoassay Hand-* book, Ed. David Wild, Elsevier LTD, Oxford; 3rd ed. (May 2005), ISBN-13: 978-0080445267; Hultschig C et al., Curr Opin Chem Biol. 2006 February; 10(1):4-10. PMID: 16376134), incorporated herein by reference).

In a particularly preferred embodiment the assay comprises two capture molecules, preferably antibodies which are both present as dispersions in a liquid reaction mixture, wherein a first labeling component is attached to the first capture molecule, wherein said first labeling component is part of a labeling system based on fluorescence- or chemiluminescence-quenching or amplification, and a second labeling component of said marking system is attached to the second capture molecule, so that upon binding of both capture molecules to the analyte a measurable signal is generated that allows for the detection of the formed sandwich complexes in the solution comprising the sample.

Even more preferred, said labeling system comprises rare earth cryptates or rare earth chelates in combination with a fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), RHODAMINE, RHODAMINE GREEN, RHODAMINE RED, RHODAMINE 110, BODIPY dyes, such as BODIPY TMR, OREGON GREEN, Coumarines such as Umbelliferone, Benzimides, such as Hoechst 33258; Phenanthridines, such as TEXAS RED, YAKIMA YELLOW, ALEXA FLUOR, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, Encyclopedia of chemical technology, 4$^{th}$ ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridiniumesters.

The levels, i.e. the concentrations, of the one or more vasoactive hormones (or fragments thereof or precursors or fragments thereof) in the sample of the subject are used for the stratification of the subject into different risk groups for particular medications. For instance, concentrations of the vasoactive hormone (or fragments thereof or precursors or fragments thereof) above or in other cases below a certain threshold value is indicative for the risk of an unfavourable effect in the subject after having received said medication.

Survival analysis (Cox regression and hazard ratios) and Kaplan-Meier estimators may be used for the assessment or prediction of the risk (e.g. morbidity) of a certain medication for a patient with a vasoactive hormone level (or fragments thereof or precursors or fragments thereof) e.g. above or below a cut off.

Sequences

The amino acid sequence of the precursor peptide of Adrenomedullin (pre-pro-Adrenomedullin) is given in SEQ ID NO: 1. Pro-Adrenomedullin relates to amino acid residues 22 to 185 of the sequence of pre-pro-Adrenomedullin. The amino acid sequence of pro-Adrenomedullin (pro-ADM) is given in SEQ ID NO:2. The pro-ADM N-terminal 20 peptide (PAMP) relates to amino acid residues 22-41 of pre-proADM. The amino acid sequence of PAMP is given in SEQ ID NO:3. MR-pro-Adrenomedullin (MR-pro-ADM) relates to amino acid residues 45-92 of pre-pro-ADM. The amino acid sequence of MR-pro-ADM is provided in SEQ ID NO:4. The amino acid sequence of mature Adrenomedullin (ADM) is given in SEQ ID NO:5.

```
(amino acid sequence of pre-pro-ADM):
                                                        SEQ ID NO: 1
  1 MKLVSVALMY LGSLAFLGAD TARLDVASEF RKKWNKWALS RGKRELRMSS

51 SYPTGLADVK AGPAQTLIRP QDMKGASRSP EDSSPDAARI RVKRYRQSMN

101 NFQGLRSFGC RFGTCTVQKL AHQIYQFTDK DKDNVAPRSK ISPQGYGRRR

151 RRSLPEAGPG RTLVSSKPQA HGAPAPPSGS APHFL (amino acid sequence of pro-ADM):
                                                        SEQ ID NO: 2
  1 ARLDVASEFR KKWNKWALSR GKRELRMSSS YPTGLADVKA GPAQTLIRPQ

51 DMKGASRSPE DSSPDAARIR VKRYRQSMNN FQGLRSFGCR FGTCTVQKLA

101 HQIYQFTDKD KDNVAPRSKI SPQGYGRRRR RSLPEAGPGR TLVSSKPQAH

151 GAPAPPSGSA PHFL (amino acid sequence of pro-ADM N20):
                                                        SEQ ID NO: 3
  1 ARLDVASEFR KKWNKWALSR (amino acid sequence of MR-pro-ADM):
                                                        SEQ ID NO: 4
  1 ELRMSSSYPT GLADVKAGPA QTLIRPQDMK GASRSPEDSS (amino acid sequence of ADM):
                                                        SEQ ID NO: 5
  1 YRQSMNNFQG LRSFGCRFGT CTVQKLAHQI YQFTDKDKDN VAPRSKISPQ

51 GY
```

The amino acid sequence of the atrial natriuretic peptide (ANP) is given in SEQ ID NO:8. The sequence of the 153 amino acid pre-pro-ANP is shown in SEQ ID NO:6. Upon cleavage of an N-terminal signal peptide (25 amino acids) and the two C-terminal amino acids (127/128) proANP (SEQ ID NO:7) is released. ANP comprises residues 99-126 from the C-terminus of the precursor prohormone pro-ANP. This pro-hormone is cleaved into the mature 28 amino acid peptide ANP, also known as ANP (1-28) or α-ANP, and the amino terminal fragment ANP (1-98) (NT-proANP, SEQ ID NO:9).

Mid-regional proANP (MR-proANP) is defined as NT-proANP or any fragments thereof comprising at least amino acid residues 53-90 (SEQ ID NO:10) of proANP. The C-terminal two arginine residues (positions 152 and 153 in pre-pro-ANP, SEQ ID NO:6, are not present in another allele of the gene encoding pre-pro-ANP, thus pre-pro-ANP may comprise only residues 1 to 151. This of course is also true for the respective fragments of pre-pro-ANP, particularly pro-ANP.

```
(amino acid sequence of pre-pro-ANP):
                                                   SEQ ID NO: 6
  1 MSSFSTTTVS FLLLLAFQLL GQTRANPMYN AVSNADLMDF KNLLDHLEEK

51 MPLEDEVVPP QVLSEPNEEA GAALSPLPEV PPWTGEVSPA QRDGGALGRG

101 PWDSSDRSAL LKSKLRALLT APRSLRRSSC FGGRMDRIGA QSGLGCNSFR

151 YRR (amino acid sequence of pro-ANP):
                                                   SEQ ID NO: 7
  1 NPMYNAVSNA DLMDFKNLLD HLEEKMPLED EVVPPQVLSE PNEEAGAALS

51 PLPEVPPWTG EVSPAQRDGG ALGRGPWDSS DRSALLKSKL RALLTAPRSL

101 RRSSCFGGRM DRIGAQSGLG CNSFRY (amino acid sequence of ANP):
                                                   SEQ ID NO: 8
1 SLRRSSCFGG RMDRIGAQSG LGCNSFRY (amino acid sequence of NT-proANP):
                                                   SEQ ID NO: 9
  1 NPMYNAVSNA DLMDFKNLLD HLEEKMPLED EVVPPQVLSE PNEEAGAALS

51 PLPEVPPWTG EVSPAQRDGG ALGRGPWDSS DRSALLKSKL RALLTAPR (amino acid sequence of amino acids 53-90 of proANP):
                                                   SEQ ID NO: 10
 1 PEVPPWTGEV SPAQRDGGAL GRGPWDSSDR SALLKSKL
```

The sequence of the 164 amino acid precursor peptide of Vasopressin (pre-pro-Vasopressin) is given in SEQ ID NO:11. Pro-Vasopressin relates to the amino acid residues 29 to 164 of the sequence of pre-pro-Vasopressin. The amino acid sequence of pro-Vasopressin is given in SEQ ID NO:12. Pro-Vasopressin is cleaved into mature Vasopressin, Neurophysin II and C-terminal proVasopressin (CT-proAVP or Copeptin). Vasopressin relates to the amino acid residues 20 to 28 of pre-pro-Vasopressin. The amino acid sequence of Vasopressin is shown in SEQ ID NO:13. Coeptin relates to amino acid residues 126 to 164 of pre-pro-Vasopressin. The amino acid sequence of Copeptin is provided in SEQ ID NO:14. Neurophysin II comprises the amino acid residues 32 to 124 of pre-pro-Vasopressin and its sequence is shown in SEQ ID NO:15.

```
(amino acid sequence of pre-pro-AVP):
                                                   SEQ ID NO: 11
  1 MPDTMLPACF LGLLAFSSAC YFQNCPRGGK RAMSDLELRQ CLPCGPGGKG

51 RCFGPSICCA DELGCFVGTA EALRCQEENY LPSPCQSGQK ACGSGGRCAA

101 FGVCCNDESC VTEPECREGF HRRARASDRS NATQLDGPAG ALLLRLVQLA

151 GAPEPFEPAQ PDAY (amino acid sequence of pro-AVP):
                                                   SEQ ID NO: 12
  1 CYFQNCPRGG KRAMSDLELR QCLPCGPGGK GRCFGPSICC ADELGCFVGT

51 AEALRCQEEN YLPSPCQSGQ KACGSGGRCA AFGVCCNDES CVTEPECREG
```

```
101 FHRRARASDR SNATQLDGPA GALLLRLVQL AGAPEPFEPA QPDAY (amino acid sequence of AVP):
                                                    SEQ ID NO: 13
  1 CYFQNCPRG (amino acid sequence of CT-pre-proAVP or Copeptin):
                                                    SEQ ID NO: 14
  1 ASDRSNATQL DGPAGALLLR LVQLAGAPEP FEPAQPDAY (amino acid sequence of Neurophysin II):
                                                    SEQ ID NO: 15
  1 AMSDLELRQC LPCGPGGKGR CFGPSICCAD ELGCFVGTAE ALRCQEENYL

51 PSPCQSGQKA CGSGGRCAAF GVCCNDESCV TEPECREGFH RRA
```

The sequence of the 212 amino acid precursor peptide of Endothelin-1 (pre-pro-Endothelin-1) is given in SEQ ID NO:16. Pro-ET-1 relates to the amino acid residues 18 to 212 of the sequence of pre-pro-ET-1. The amino acid sequence of pro-ET-1 is given in SEQ ID NO:17. Pro-ET-1 is cleaved into mature ET-1, big-ET-1 and C-terminal proET-1 (CT-proET-1). ET-1 relates to the amino acid residues 53 to 73 of pre-pro-ET-1. The amino acid sequence of ET-1 is shown in SEQ ID NO:18. CT-proET-1 relates to amino acid residues 168 to 212 of pre-pro-ET-1. The amino acid sequence of CT-proET-1 is provided in SEQ ID NO:19. Big-ET-1 comprises the amino acid residues 53 to 90 of pre-pro-ET-1 and its sequence is shown in SEQ ID NO:20.

```
(amino acid sequence of pre-pro-ET-1):
                                                    SEQ ID NO: 16
  1 MDYLLMIFSL LFVACQGAPE TAVLGAELSA VGENGGEKPT PSPPWRLRRS

51 KRCSCSSLMD KECVYFCHLD IIWVNTPEHV VPYGLGSPRS KRALENLLPT

101 KATDRENRCQ CASQKDKKCW NFCQAGKELR AEDIMEKDWN NHKKGKDCSK

151 LGKKCIYQQL VRGRKIRRSS EEHLRQTRSE TMRNSVKSSF HDPKLKGKPS

201 RERYVTHNRA HW (amino acid sequence of pro-ET-1):
                                                    SEQ ID NO: 17
  1 APETAVLGAE LSAVGENGGE KPTPSPPWRL RRSKRCSCSS LMDKECVYFC

51 HLDIIWVNTP EHVVPYGLGS PRSKRALENL LPTKATDREN RCQCASQKDK

101 KCWNFCQAGK ELRAEDIMEK DWNNHKKGKD CSKLGKKCIY QQLVRGRKIR

151 RSSEEHLRQT RSETMRNSVK SSFHDPKLKG KPSRERYVTH NRAHW (amino acid sequence of ET-1):
                                                    SEQ ID NO: 18
  1 CSCSSLMDKE CVYFCHLDII W (amino acid sequence of CT-pro-ET-1):
                                                    SEQ ID NO: 19
  1 RSSEEHLRQT RSETMRNSVK SSFHDPKLKG KPSRERYVTH NRAHW (amino acid sequence of Big-ET-1):
                                                    SEQ ID NO: 20
  1 CSCSSLMDKE CVYFCHLDII WVNTPEHVVP YGLGSPRS
```

The sequence of the 134 amino acid precursor peptide of brain natriuretic peptide (pre-pro-BNP) is given in SEQ ID NO:21. Pro-BNP relates to amino acid residues 27 to 134 of pre-pro-BNP. The sequence of pro-BNP is shown in SEQ ID NO:22. Pro-BNP is cleaved into N-terminal pro-BNP (NT-pro-BNP) and mature BNP. NT-pro-BNP comprises the amino acid residues 27 to 102 and its sequence is shown in SEQ ID NO:23. The SEQ ID NO:24 shows the sequence of BNP comprising the amino acid residues 103 to 134 of the pre-pro-BNP peptide.

```
(amino acid sequence of pre-pro-BNP):
                                                    SEQ ID NO: 21
  1 MDPQTAPSRA LLLLLFLHLA FLGGRSHPLG SPGSASDLET SGLQEQRNHL

51 QGKLSELQVE QTSLEPLQES PRPTGVWKSR EVATEGIRGH RKMVLYTLRA
```

```
101 PRSPKMVQGS GCFGRKMDRI SSSSGLGCKV LRRH (amino acid sequence of pro-BNP):
                                              SEQ ID NO: 22
  1 HPLGSPGSAS DLETSGLQEQ RNHLQGKLSE LQVEQTSLEP LQESPRPTGV

51 WKSREVATEG IRGHRKMVLY TLRAPRSPKM VQGSGCFGRK MDRISSSSGL

101 GCKVLRRH (amino acid sequence of NT-pro-BNP):
                                              SEQ ID NO: 23
  1 HPLGSPGSAS DLETSGLQEQ RNHLQGKLSE LQVEQTSLEP LQESPRPTGV

51 WKSREVATEG IRGHRKMVLY TLRAPR (amino acid sequence of BNP):
                                              SEQ ID NO: 24
  1 SPKMVQGSGC FGRKMDRISS SSGLGCKVLR RH
```

DESCRIPTION OF DRAWINGS

FIG. 1: Marker MR-proADM and medicament ACE-Inhibitor; solid line means no medication, dashed line means medication; A: overall population (n=974), n=506 without medication (deaths=64), n=441 with medication (deaths=42); B: 1st MR-proADM quintile (0.03-0.657 nmol/L; n=188), n=135 without medication (deaths=2), n=53 with medication (deaths=2); C: 2nd to 4th MR-proADM quintiles (0.658-1.89 nmol/L; n=570), n=271 without medication (deaths=31), n=299 with medication (deaths=23); D: 5th MR-proADM quintile (1.90-14.6 nmol/L; n=189), n=100 without medication (deaths=31), n=89 with medication (deaths=17).

FIG. 2: Marker MR-proANP and medicament Statin; solid line means no medication, dashed line means medication; A: overall population (n=1330), n=887 without medication (deaths=57), n=443 with medication (deaths=22); B: 1st MR-proANP quintile (3.9-54.6 pmol/L; n=259), n=234 without medication (deaths=1), n=25 with medication (deaths=1); C: 2nd to 4th MR-proANP quintiles (54.7-431 pmol/L; n=805), n=501 without medication (deaths=28), n=304 with medication (deaths=8); D: 5th MR-proADM quintile (431.1-2510 pmol/L; n=266), n=152 without medication (deaths=28), n=144 with medication (deaths=13).

FIG. 3: Marker CT-proAVP and medicament Diuretic; solid line means no medication, dashed line means medication; A: overall population (n=943), n=588 without medication (deaths=59), n=355 with medication (deaths=47); B: 1st CT-proAVP quintile (0.71-5.44 pmol/L; n=188), n=159 without medication (deaths=8), n=29 with medication (deaths=2); C: 2nd to 4th CT-proAVP quintiles (5.45-43.2 pmol/L; n=566), n=354 without medication (deaths=26), n=212 with medication (deaths=19); D: 5th CT-proAVP quintile (43.3-1050 pmol/L; n=189), n=75 without medication (deaths=25), n=114 with medication (deaths=26).

FIG. 4: Marker BNP and medicament Calcium-Channel Blocker; solid line means no medication, dashed line means medication; A: overall population (n=892), n=666 without medication (deaths=59), n=226 with medication (deaths=11); B: 1st BNP quintile (3-65 pg/mL; n=183), n=152 without medication (deaths=4), n=31 with medication (deaths=2); C: 2nd to 4th BNP quintiles (65-904 pg/mL; n=537), n=378 without medication (deaths=27), n=159 with medication (deaths=7); D: 5th BNP quintile (904-7850 pg/mL; n=172), n=136 without medication (deaths=28), n=36 with medication (deaths=2).

FIG. 5: Marker CT-proET-1 and medicament Beta-Blocker; solid line means no medication, dashed line means medication; A: overall population (n=895), n=432 without medication (deaths=39), n=463 with medication (deaths=31); B: 1st CT-proET-1 quintile (6.92-67 pmol/L; n=184), n=121 without medication (deaths=0), n=63 with medication (deaths=1); C: 2nd to 4th CT-proET-1 quintiles (67-182 pmol/L; n=542), n=249 without medication (deaths=21), n=293 with medication (deaths=18); D: 5th CT-proET-1 quintile (182-709 pmol/L; n=169), n=62 without medication (deaths=18), n=107 with medication (deaths=12).

FIG. 6: Marker NT-proBNP and medicament Warfarin; solid line means no medication, dashed line means medication; A: overall population (n=875), n=651 without medication (deaths=53), n=224 with medication (deaths=15); B: 1st NT-proBNP quintile (3-280 pg/mL; n=174), n=159 without medication (deaths=4), n=15 with medication (deaths=1); C: 2nd to 4th NT-proBNP quintiles (280-7080 pg/mL; n=535), n=374 without medication (deaths=26), n=161 with medication (deaths=7); D: 5th NT-proBNP quintile (7080-112000 pg/mL; n=166), n=118 without medication (deaths=23), n=48 with medication (deaths=7).

FIG. 7: Marker combination MR-proADM and CT-proET-1 and medicament ACE-Inhibitor; solid line means no medication, dashed line means medication; A: overall population (n=1330), n=739 without medication (deaths=51), n=591 with medication (deaths=28); B: 1st quintile with both biomarkers below the median (n=560; median MR-proADM concentration 0.875 nmol/L, median CT-proET-1 concentration 88.2 pmol/L), n=396 without medication (deaths=6), n=164 with medication (deaths=3); C: $2^{nd}$ to $4^{th}$ quintile with either MR-proADM or CT-proET-1 above the respective median (n=167), n=89 without medication (deaths=6), n=78 with medication (deaths=5); D: $5^{th}$ quintile with both biomarkers above the respective median (n=603), n=254 without medication (deaths=39), n=349 with medication (deaths=20).

FIG. 8: Marker CT-proET-1 and medicament combination ACE-Inhibitor and Beta-Blocker; solid line means no medication, dashed line means medication; A: overall population (n=607), n=344 without medication (deaths=43), n=263 with medication (deaths=27); B: 1st CT-proET-1 quintile (6,9-67 pmol/L, n=137), n=101 without medication (deaths=1), n=36 with medication (deaths=2); C: 2nd to 4th CT-proET-1 quintile (67-182 pmol/L, n=353), n=194 without medication (deaths=26), n=159 with medication (deaths=11); D: 5th CT-proET-1 quintile (182-709 pmol/L, n=117), n=49 without medication (deaths=16), n=68 with medication (deaths=14).

FIG. 9: Marker CT-proAVP and Medicament Diuretic; solid line means no medication, dashed line means medication; A: overall population (n=418), n=279 without medication (deaths=13), n=139 with medication (deaths=24); B: 1st CT-proAVP quintile (0.9-3.93 pmol/L; n=87), n=67 without medication (deaths=1), n=20 with medication (deaths=0); C: 2nd to 4th CT-proAVP quintiles (3.93-32.9 pmol/L; n=247), n=170 without medication (deaths=6), n=77 with medication (deaths=8); D: 5th CT-proAVP quintile (32.9-778 pmol/L; n=84), n=42 without medication (deaths=6), n=42 with medication (deaths=16).

FIG. 10: Marker CT-proET-1 and Medicament Statin; solid line means no medication, dashed line means medication; A: overall population (n=415), n=310 without medication (deaths=26), n=105 with medication (deaths=9); B: 1st CT-proET-1 quintile (1-51.4 pmol/L; n=85), n=75 without medication (deaths=3), n=10 with medication (deaths=2); C: 2nd to 4th CT-proET-1 quintiles (51.4-93.1 pmol/L; n=252), n=178 without medication (deaths=10), n=74 with medication (deaths=4); D: 5th CT-proET-1 quintile (93.1-571 pmol/L; n=78), n=57 without medication (deaths=13), n=21 with medication (deaths=3).

FIG. 11: Marker MR-proADM and Medicament Statin; solid line means no medication, dashed line means medication; A: overall population (n=417), n=312 without medication (deaths=26), n=105 with medication (deaths=9); B: 1st MR-proADM quintile (0.05-0.47 nmol/L; n=93), n=80 without medication (deaths=3), n=13 with medication (deaths=2); C: 2nd to 4th MR-proADM quintiles (0.47-0.91 nmol/L; n=245), n=176 without medication (deaths=8), n=69 with medication (deaths=5); D: 5th MR-proADM quintile (0.91-5.49 nmol/L; n=79), n=56 without medication (deaths=15), n=23 with medication (deaths=2).

FIG. 12: Marker MR-proANP and Medicament Acetylsalicylic Acid; solid line means no medication, dashed line means medication; A: overall population (n=449), n=240 without medication (deaths=22), n=209 with medication (deaths=20); B: 1st MR-proANP quintile (22.3-69.5 pmol/L; n=91), n=40 without medication (deaths=0), n=51 with medication (deaths=0); C: 2nd to 4th MR-proANP quintiles (69.5-250 pmol/L; n=272), n=148 without medication (deaths=12), n=124 with medication (deaths=6); D: 5th MR-proANP quintile (250-1540 pmol/L; n=86), n=52 without medication (deaths=10), n=34 with medication (deaths=14).

FIG. 13: Marker combination MR-proADM and CT-proET-1 and Antihypertensive Medication; solid line means no medication, dashed line means medication; A: overall population (n=432), n=164 without medication (deaths=8), n=268 with medication (deaths=30); B: 1st quintile with both biomarkers below the median (n=176; median MR-proADM concentration 0.67 nmol/L, median CT-proET-1 concentration 69.1 pmol/L), n=101 without medication (deaths=1), n=75 with medication (deaths=4); C: 2nd to 4th quintile with either MR-proADM or CT-proET-1 above the respective median (n=89), n=32 without medication (deaths=1), n=61 with medication (deaths=8); D: 5th quintile with both biomarkers above the respective median (n=163), n=31 without medication (deaths=6), n=132 with medication (deaths=18).

FIG. 14: Marker MR-proADM and Medicament Diuretic; solid line means no medication, dashed line means medication; A: overall population (n=1160), n=869 without medication (deaths=56), n=291 with medication (deaths=24); B: 1st MR-proADM quintile (0.04-0.47 nmol/L; n=229), n=209 without medication (deaths=5), n=20 with medication (deaths=3); C: 2nd to 4th MR-proADM quintiles (0.47-1.18 nmol/L; n=700), n=542 without medication (deaths=15), n=158 with medication (deaths=7); D: 5th MR-proADM quintile (1.18-6.75 nmol/L; n=231), n=118 without medication (deaths=36), n=113 with medication (deaths=14).

FIG. 15: Marker MR-proANP and Medicament Diuretic; solid line means no medication, dashed line means medication; A: overall population (n=1464), n=990 without medication (deaths=55), n=474 with medication (deaths=37); B: 1st MR-proANP quintile (4.9-65 pmol/L; n=300), n=250 without medication (deaths=1), n=50 with medication (deaths=2); C: 2nd to 4th MR-proANP quintiles (65-264 pmol/L; n=871), n=612 without medication (deaths=21), n=259 with medication (deaths=14); D: 5th MR-proANP quintile (264-1630 pmol/L; n=293), n=128 without medication (deaths=33), n=165 with medication (deaths=21).

FIG. 16: Marker CT-proAVP and Medicament Nitrate; solid line means no medication, dashed line means medication; A: overall population (n=1161), n=667 without medication (deaths=58), n=494 with medication (deaths=23); B: 1st CT-proAVP quintile (0.31-4.6 pmol/L; n=231), n=162 without medication (deaths=1), n=69 with medication (deaths=2); C: 2nd to 4th CT-proAVP quintiles (4.6-42.1 pmol/L; n=698), n=380 without medication (deaths=19), n=318 with medication (deaths=11); D: 5th CT-proAVP quintile (42.1-1040 pmol/L; n=232), n=125 without medication (deaths=38), n=107 with medication (deaths=10).

FIG. 17: Marker CT-proET-1 and Medicament Calcium Channel Blocker; solid line means no medication, dashed line means medication; A: overall population (n=1459), n=1207 without medication (deaths=77), n=252 with medication (deaths=16); B: 1st CT-proET-1 quintile (4.6-56.6 pmol/L; n=295), n=252 without medication (deaths=6), n=43 with medication (deaths=2); C: 2nd to 4th CT-proET-1 quintiles (56.6-118 pmol/L; n=877), n=723 without medication (deaths=23), n=154 with medication (deaths=7); D: 5th CT-proET-1 quintile (118-671 pmol/L; n=287), n=232 without medication (deaths=48), n=55 with medication (deaths=7).

FIG. 18: Marker NT-proBNP and Medicament Calcium Channel Blocker; solid line means no medication, dashed line means medication; A: overall population (n=1174), n=1026 without medication (deaths=78), n=148 with medication (deaths=7); B: 1st NT-proBNP quintile (0.3-204 pg/mL; n=223), n=200 without medication (deaths=3), n=23 with medication (deaths=1); C: 2nd to 4th NT-proBNP quintiles (204-3160 pg/mL; n=713), n=618 without medication (deaths=34), n=95 with medication (deaths=4); D: 5th NT-proBNP quintile (3160-11800 pg/mL; n=238), n=208 without medication (deaths=41), n=30 with medication (deaths=2).

FIG. 19: Marker CT-proAVP and combination of medicaments Nitrate and Diuretic; solid line means no medication, dashed line means medication; A: overall population (n=647), n=511 without medication (deaths=43), n=136 with medication (deaths=10); B: $1^{st}$ CT-proAVP quintile (0.31-4.6 pmol/L; n=159), n=141 without medication (deaths=1), n=18 with medication (deaths=2); C: $2^{nd}$ to $4^{th}$ CT-proAVP quintiles (4.6-42.1 pmol/L; n=364), n=285 without medication (deaths=13), n=79 with medication (deaths=3); D: $5^{th}$ CT-proAVP quintile (42.1-1040 pmol/L; n=124), n=85 without medication (deaths=29), n=39 with medication (deaths=5).

FIG. 20: Marker combination CT-proAVP and MR-proADM and Medicament Diuretic; solid line means no medication, dashed line means medication; A: overall population (n=1161), n=870 without medication (deaths=56), n=291 with medication (deaths=24); B: $1^{st}$ quintile with both biomarkers below the median (n=362, median CT-proAVP concentration 10.75 pmol/L, median MR-proADM concentration 0.72 nmol/L), n=326 without medication (deaths=2), n=36 with medication (deaths=1); C: $2^{nd}$ to $4^{th}$ quintile with either CT-proAVP or MR-proADM above the respective median (n=437), n=343 without medication (deaths=15), n=94 with medication (deaths=7); D: $5^{th}$ quintile with both biomarkers above the respective median (n=362), n=201 without medication (deaths=39), n=161 with medication (deaths=16).

FIG. 21: Marker combination CT-proAVP and MR-proANP and combination of medicaments Nitrate and Diuretic; solid line means no medication, dashed line means medication; A: overall population (n=646), n=511 without medication (deaths=43), n=135 with medication (deaths=10); B: $1^{st}$ quintile with both biomarkers below the median (n=239, median CT-proAVP concentration 10.75 pmol/L, median MR-proANP concentration 117 pmol/L), n=223 without medication (deaths=3), n=16 with medication (deaths=1); C: $2^{nd}$ to $4^{th}$ quintile with either CT-proAVP or MR-proANP above the respective median (n=210), n=161 without medication (deaths=6), n=49 with medication (deaths=2); D: $5^{th}$ quintile with both biomarkers above the respective median (n=197), n=127 without medication (deaths=34), n=70 with medication (deaths=7).

FIG. 22: Marker MR-proADM and Medicament Diuretic; solid line means no medication, dashed line means medication; A: overall population (n=1160), n=869 without medication (MACE=116), n=291 with medication (MACE=67); B: $1^{st}$ MR-proADM quintile (0.04-0.47 nmol/L; n=229), n=209 without medication (MACE=16), n=20 with medication (MACE=6); C: $2^{nd}$ to $4^{th}$ MR-proADM quintiles (0.47-1.18 nmol/L; n=700), n=542 without medication (MACE=51), n=158 with medication (MACE=28); D: $5^{th}$ MR-proADM quintile (1.18-6.75 nmol/L; n=231), n=118 without medication (MACE=49), n=113 with medication (MACE=33).

FIG. 23: Marker MR-proANP and Medicament Calcium Channel Blocker; solid line means no medication, dashed line means medication; A: overall population (n=1160), n=1015 without medication (MACE=162), n=145 with medication (MACE=21); B: $1^{st}$ MR-proANP quintile (14.5-59.6 pmol/L; n=230), n=215 without medication (MACE=5), n=15 with medication (MACE=1); C: $2^{nd}$ to $4^{th}$ MR-proANP quintiles (59.6-283 pmol/L; n=698), n=600 without medication (MACE=72), n=98 with medication (MACE=14); D: $5^{th}$ MR-proANP quintile (283-1650 pmol/L; n=232), n=200 without medication (MACE=85), n=32 with medication (MACE=6).

FIG. 24: Marker CT-proAVP and Medicament ACE Inhibitor; solid line means no medication, dashed line means medication; A: overall population (n=1463), n=399 without medication (MACE=74), n=1064 with medication (MACE=128); B: $1^{st}$ CT-proAVP quintile (0.3-3.6 pmol/L; n=293), n=75 without medication (MACE=3), n=218 with medication (MACE=20); C: $2^{nd}$ to $4^{th}$ CT-proAVP quintiles (3.6-18.7 pmol/L; n=880), n=226 without medication (MACE=25), n=654 with medication (MACE=66); D: $5^{th}$ CT-proAVP quintile (18.7-441 pmol/L; n=290), n=98 without medication (MACE=46), n=192 with medication (MACE=42).

FIG. 25: Marker CT-proET-1 and Medicament Calcium Channel Blocker; solid line means no medication, dashed line means medication; A: overall population (n=1459), n=1207 without medication (MACE=164), n=252 with medication (MACE=38); B: $1^{st}$ CT-proET-1 quintile (4.6-56.6 pmol/L; n=295), n=252 without medication (MACE=9), n=43 with medication (MACE=8); C: $2^{nd}$ to $4^{th}$ CT-proET-1 quintiles (56.6-118 pmol/L; n=877), n=723 without medication (MACE=75), n=154 with medication (MACE=16); D: $5^{th}$ CT-proET-1 quintile (118-671 pmol/L; n=287), n=232 without medication (MACE=80), n=55 with medication (MACE=14).

FIG. 26: Marker NT-proBNP and Medicament Beta Blocker; solid line means no medication, dashed line means medication; A: overall population (n=1174), n=234 without medication (MACE=64), n=940 with medication (MACE=128); B: $1^{st}$ NT-proBNP quintile (0.3-204 pg/mL; n=224), n=31 without medication (MACE=1), n=193 with medication (MACE=14); C: $2^{nd}$ to $4^{th}$ NT-proBNP quintiles (204-3160 pg/mL; n=712), n=123 without medication (MACE=25), n=589 with medication (MACE=71); D: $5^{th}$ NT-proBNP quintile (3160-11800 pg/mL; n=238), n=80 without medication (MACE=38), n=158 with medication (MACE=43).

FIG. 27: Marker MR-proADM and combination of medicaments Nitrate and Diuretic; solid line means no medication, dashed line means medication; A: overall population (n=647), n=511 without medication (MACE=80), n=136 with medication (MACE=37); B: $1^{st}$ MR-proADM quintile (0.035-0.47 nmol/L; n=113), n=104 without medication (MACE=8), n=9 with medication (MACE=3); C: $2^{nd}$ to $4^{th}$ MR-proADM quintiles (0.47-1.18 nmol/L; n=406), n=333 without medication (MACE=37), n=73 with medication (MACE=14); D: $5^{th}$ MR-proADM quintile (1.18-6.75 nmol/L; n=128), n=74 without medication (MACE=35), n=54 with medication (MACE=20).

FIG. 28: Marker MR-proANP and combination of medicaments Nitrate and Diuretic; solid line means no medication, dashed line means medication; A: overall population (n=788), n=592 without medication (MACE=76), n=196 with medication (MACE=47); B: $1^{st}$ MR-proANP quintile (4.9-65 pmol/L; n=172), n=154 without medication (MACE=3), n=18 with medication (MACE=2); C: $2^{nd}$ to $4^{th}$ MR-proANP quintiles (65-264 pmol/L; n=455), n=357 without medication (MACE=41), n=98 with medication (MACE=20); D: $5^{th}$ MR-proANP quintile (264-1630 pmol/L; n=161), n=81 without medication (MACE=32), n=80 with medication (MACE=25).

FIG. 29: Marker CT-proAVP and combination of medicaments Nitrate and Thrombolytic Drug; solid line means no medication, dashed line means medication; A: overall population (n=788), n=559 without medication (MACE=72), n=229 with medication (MACE=30); B: 1st CT-proAVP quintile (0.3-3.6 pmol/L; n=178), n=127 without medication (MACE=4), n=51 with medication (MACE=6); C: $2^{nd}$ to $4^{th}$ CT-proAVP quintiles (3.6-18.7 pmol/L; n=475), n=328 without medication (MACE=33), n=147 with medication (MACE=17); D: $5^{th}$ CT-proAVP quintile (18.7-441 pmol/L; n=135), n=104 without medication (MACE=35), n=31 with medication (MACE=7).

FIG. 30: Marker CT-proET-1 and combination of medicaments Nitrate and Diuretic; solid line means no medication, dashed line means medication; A: overall population (n=339), n=238 without medication (MACE=35), n=56 with medication (MACE=12); B: $1^{st}$ CT-proET-1 quintile (3.7-65.4 pmol/L; n=80), n=75 without medication (MACE=3), n=5 with medication (MACE=1); C: $2^{nd}$ to $4^{th}$ CT-proET-1 quintiles (65.4-136 pmol/L; n=200), n=170 without medication (MACE=14), n=30 with medication (MACE=4); D: $5^{th}$ CT-proET-1 quintile (136-468 pmol/L; n=59), n=38 without medication (MACE=18), n=21 with medication (MACE=7).

FIG. 31: Marker NT-proBNP and combination of medicaments Beta Blocker and Diuretic; solid line means no medication, dashed line means medication; A: overall population (n=371), n=154 without medication (MACE=41), n=217 with medication (MACE=49); B: $1^{st}$ NT-proBNP quintile (0.3-204 pg/mL; n=50), n=28 without medication (MACE=1), n=22 with medication (MACE=2); C: $2^{nd}$ to $4^{th}$ NT-proBNP quintiles (204-3160 pg/mL; n=202), n=81 without medication (MACE=15), n=121 with medication (MACE=26); D: $5^{th}$ NT-proBNP quintile (3160-11800 pg/mL; n=119), n=45 without medication (MACE=25), n=74 with medication (MACE=21).

FIG. 32: Marker combination MR-proADM and MR-proANP and Medicament Calcium Channel Blocker; solid line means no medication, dashed line means medication; A: overall population (n=1161), n=1015 without medication (MACE=162), n=146 with medication (MACE=22); B: $1^{st}$ quintile with both biomarkers below the median (n=429, median MR-proADM concentration 0.72 nmol/L, median MR-proANP concentration 117 pmol/L), n=383 without medication (MACE=19), n=46 with medication (MACE=5); C: $2^{nd}$ to $4^{th}$ quintile with either MR-proADM or MR-proANP above the respective median (n=303), n=271 without medication (MACE=36), n=32 with medication (MACE=4); D: $5^{th}$ quintile with both biomarkers above the respective median (n=429), n=361 without medication (MACE=107), n=68 with medication (MACE=13).

FIG. 33: Marker combination MR-proADM and CT-proAVP and Medicament ACE Inhibitor; solid line means no medication, dashed line means medication; A: overall population (n=1163), n=209 without medication (MACE=60), n=954 with medication (MACE=124); B: $1^{st}$ quintile with both biomarkers below the median (n=362, median MR-proADM concentration 0.72 nmol/L, median CT-proAVP concentration 10.75 pmol/L), n=57 without medication (MACE=2), n=305 with medication (MACE=18); C: $2^{nd}$ to $4^{th}$ quintile with either MR-proADM or CT-proAVP above the respective median (n=439), n=66 without medication (MACE=16), n=373 with medication (MACE=46); D: $5^{th}$ quintile with both biomarkers above the respective median (n=362), n=86 without medication (MACE=42), n=276 with medication (MACE=60).

FIG. 34: Marker combination MR-proADM and MR-proANP and combination of medicaments Beta Blocker and Diuretic; solid line means no medication, dashed line means medication; A: overall population (n=365), n=151 without medication (MACE=40), n=214 with medication (MACE=48); B: $1^{st}$ quintile with both biomarkers below the median (n=75, median MR-proADM concentration 0.72 nmol/L, median MR-proANP concentration 117 pmol/L), n=45 without medication (MACE=1), n=30 with medication (MACE=4); C: $2^{nd}$ to $4^{th}$ quintile with either MR-proADM or MR-proANP above the respective median (n=89), n=36 without medication (MACE=9), n=53 with medication (MACE=13); D: $5^{th}$ quintile with both biomarkers above the respective median (n=201), n=70 without medication (MACE=30), n=131 with medication (MACE=31).

EXAMPLE

Example 1

Measurement of Biomarkers

Figure 1:
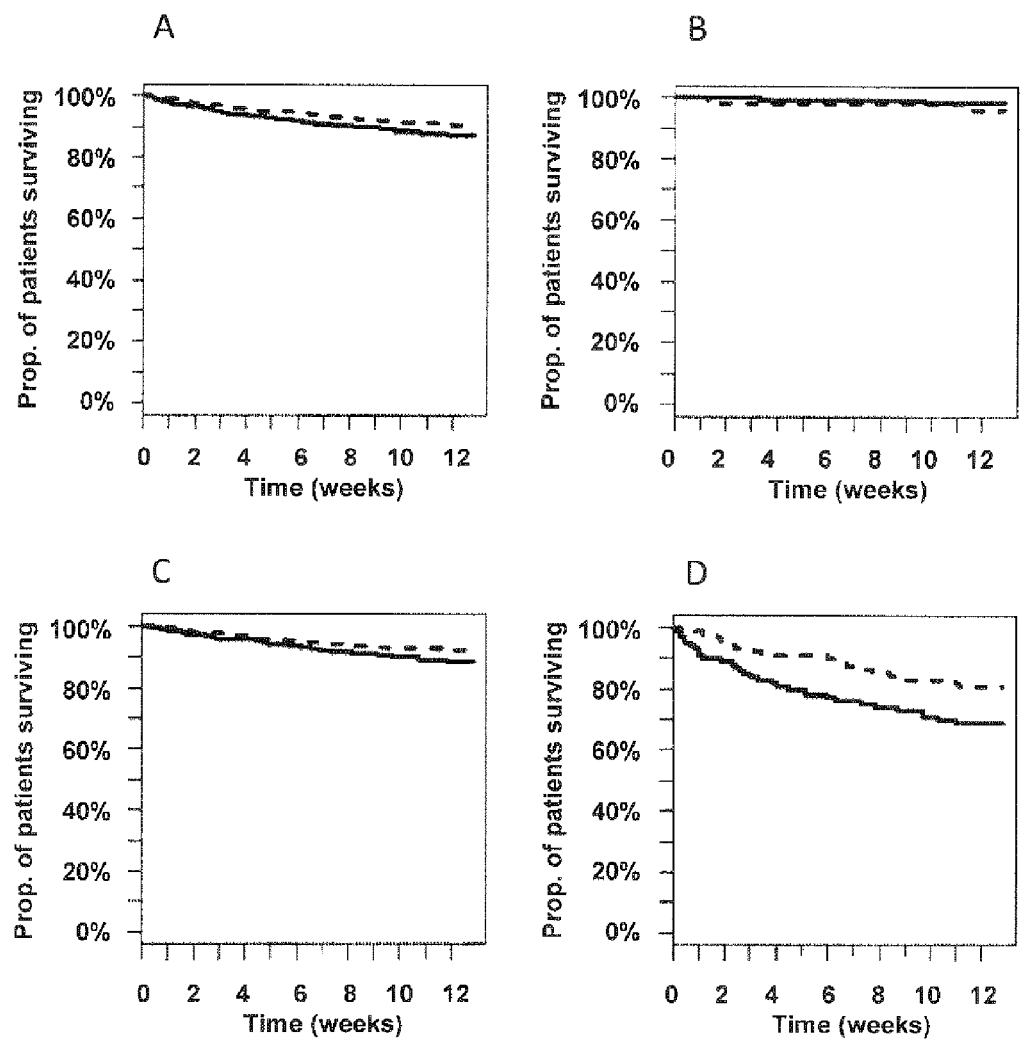
FIGS. 1 to 8 illustrate the survival rate for patients suffering from shortness of breath (SOB), acute coronary syndrome, acute heart failure (AHF), arrhythmia, asthma exacerbation, bronchitis, chest pain, influenza, chronic obstructive pulmonary disease (COPD), pneumonia and pulmonary embolism from the "Biomarkers in the Assessment of Congestive Heart failure study" ("BACH").
Figure 2:
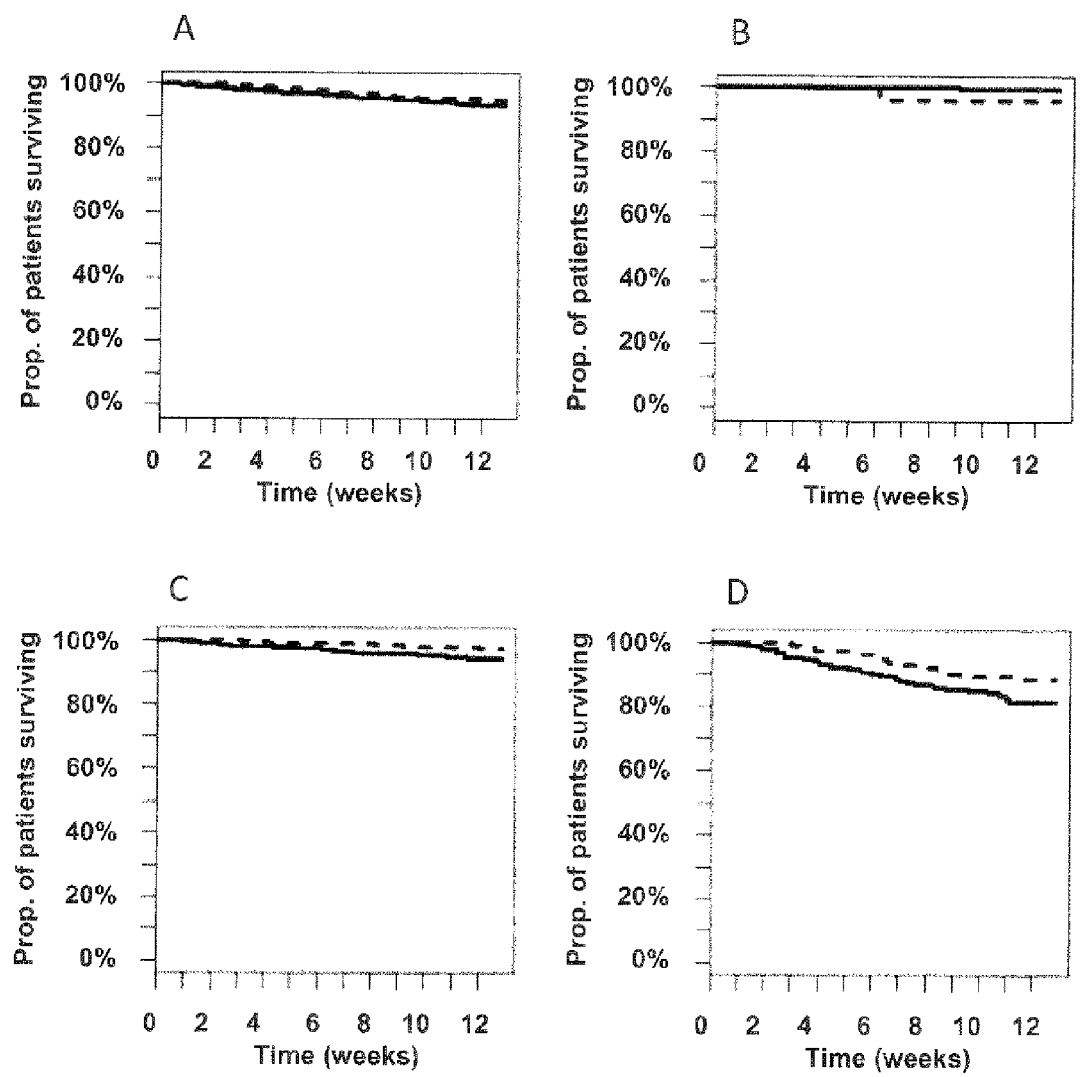
Figure 3:
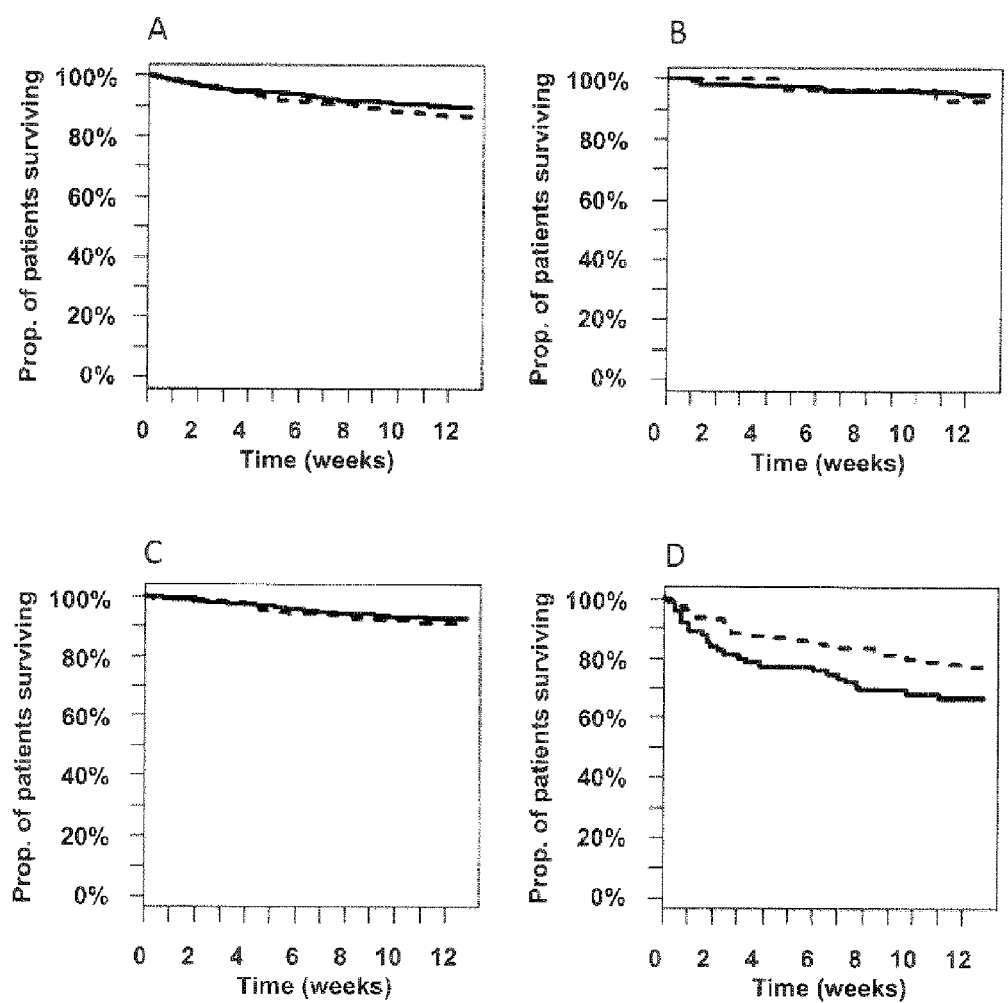
Figure 4:
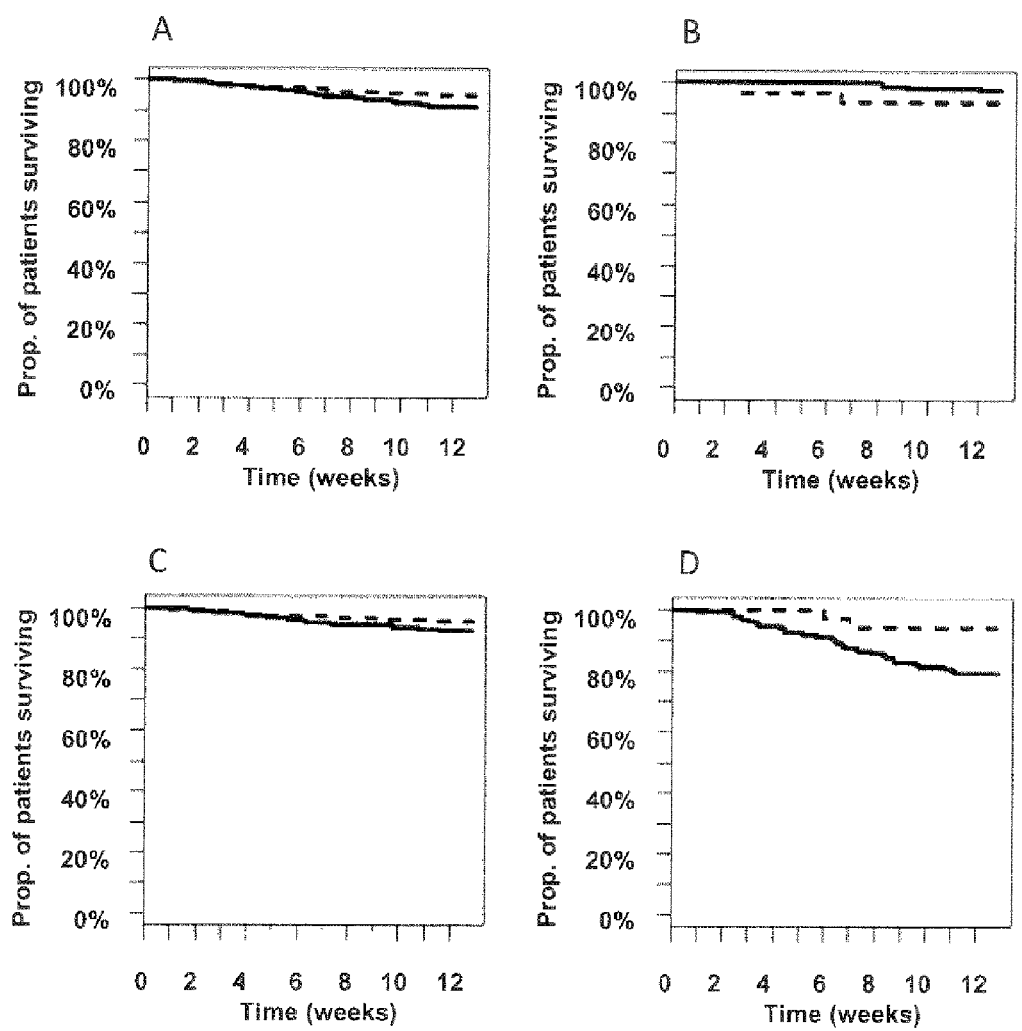
Figure 5:
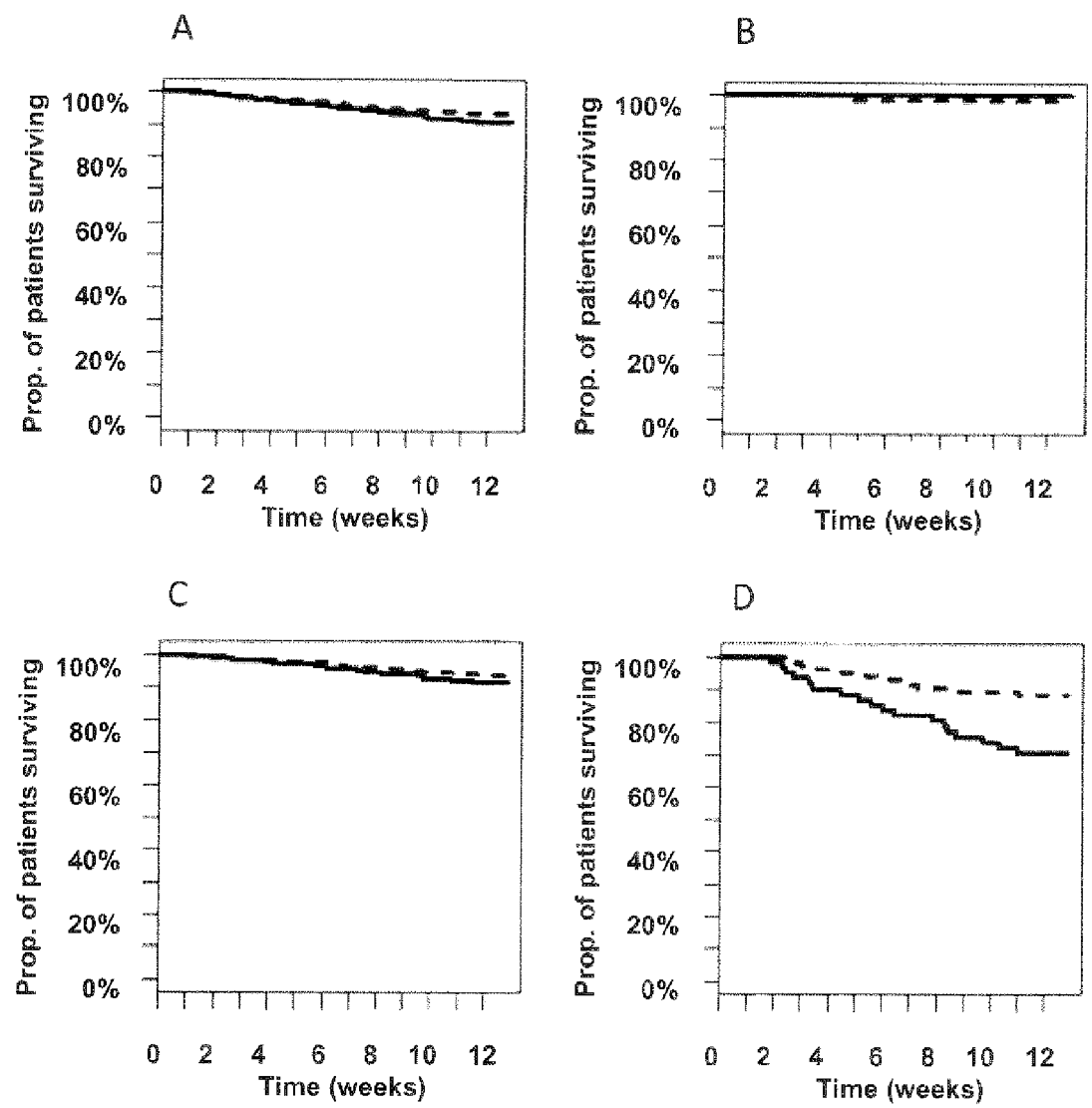
Figure 6:
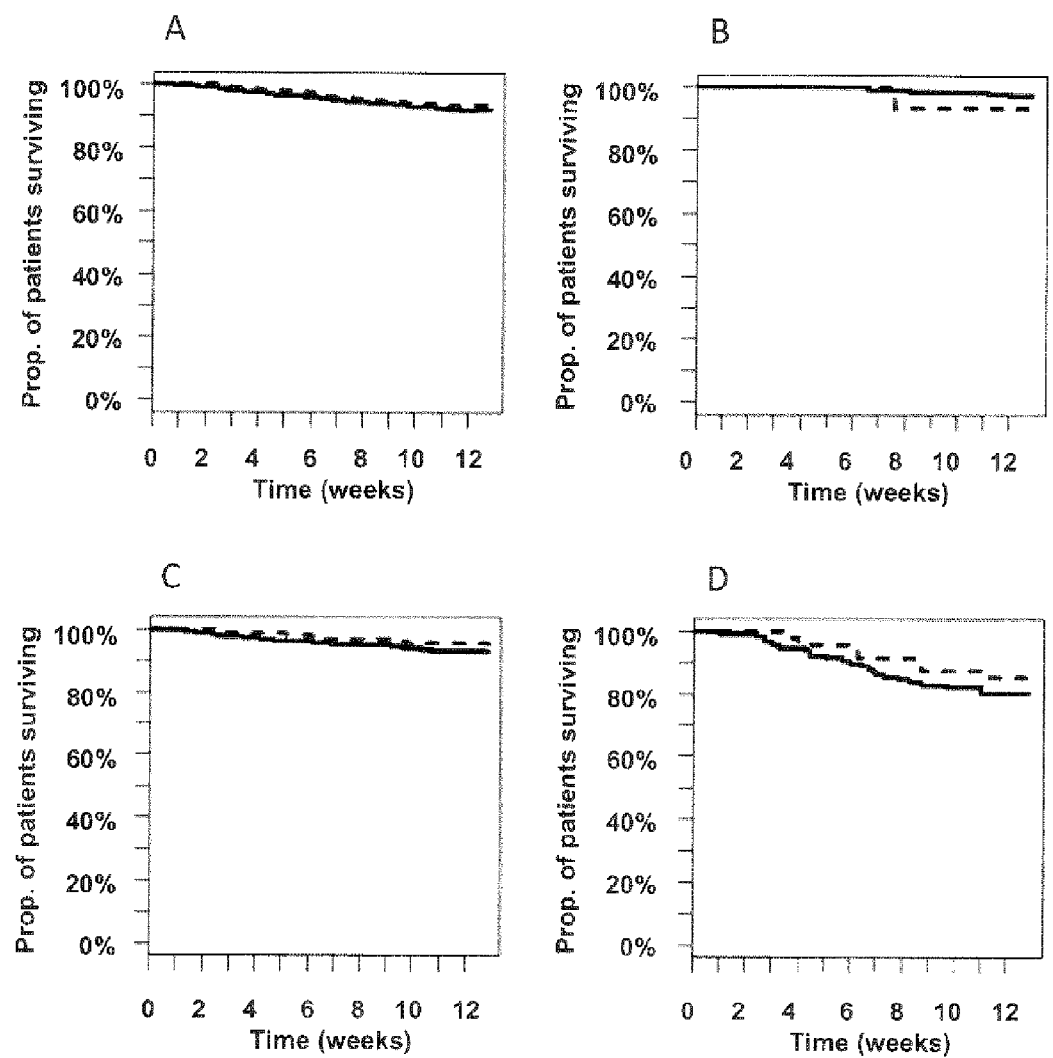
Figure 7:
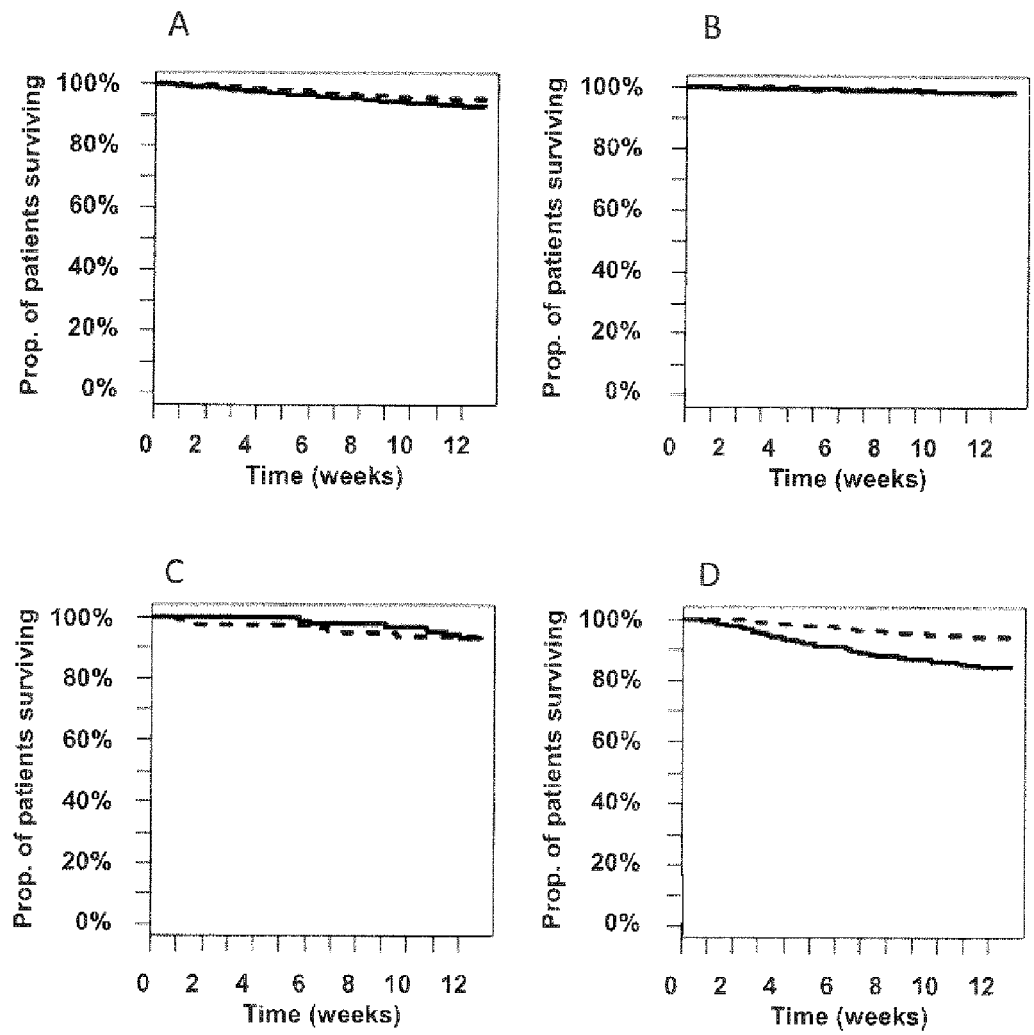
Figure 8:
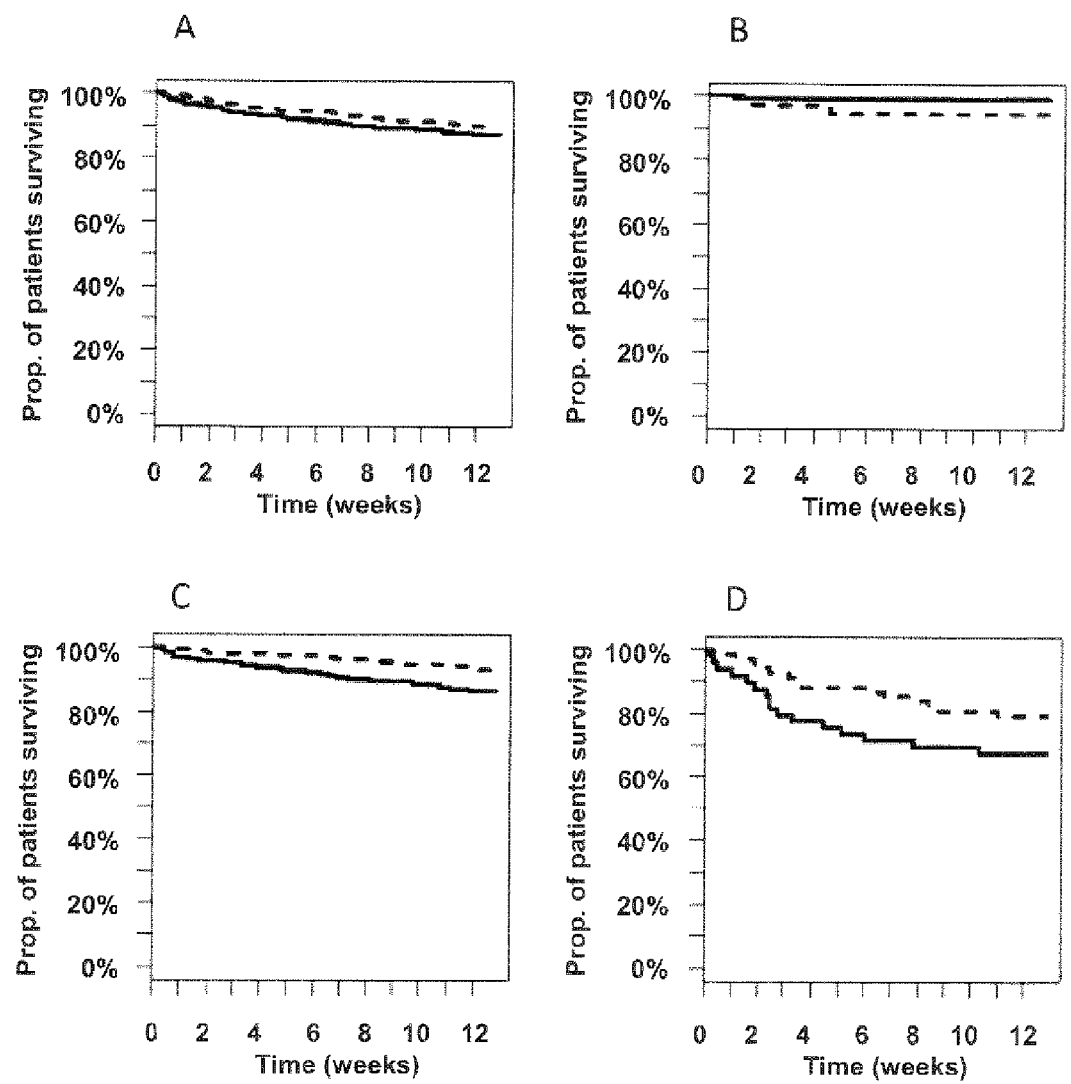
Figure 9:
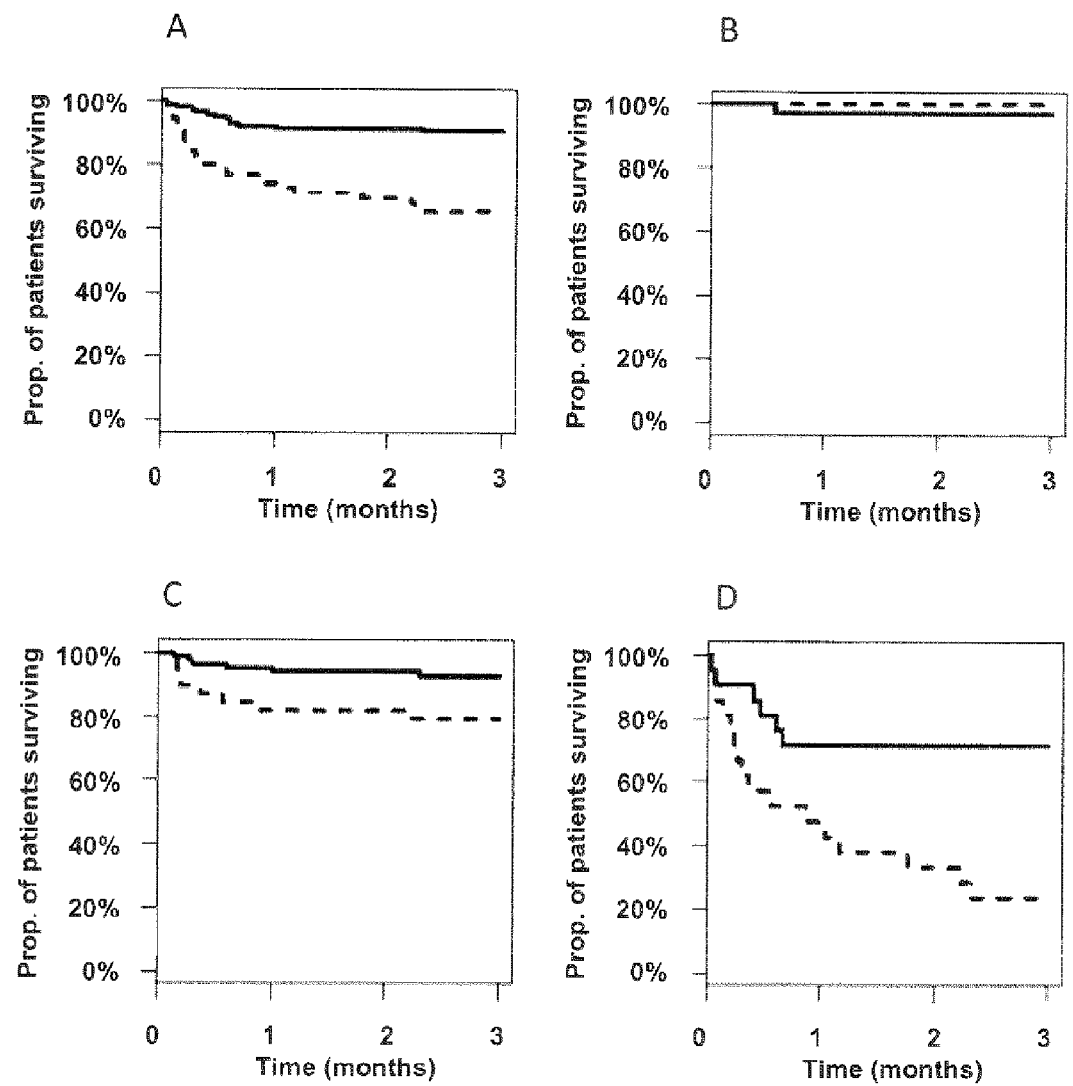
FIGS. 9 to 13 illustrate the survival rate for patients suffering from ischemic stroke, hemorrhagic stroke or transient ischemic attack from the "Copeptin to guide disease severity and Management, Osmostatus and Stress" ("COSMOS").
Figure 10:
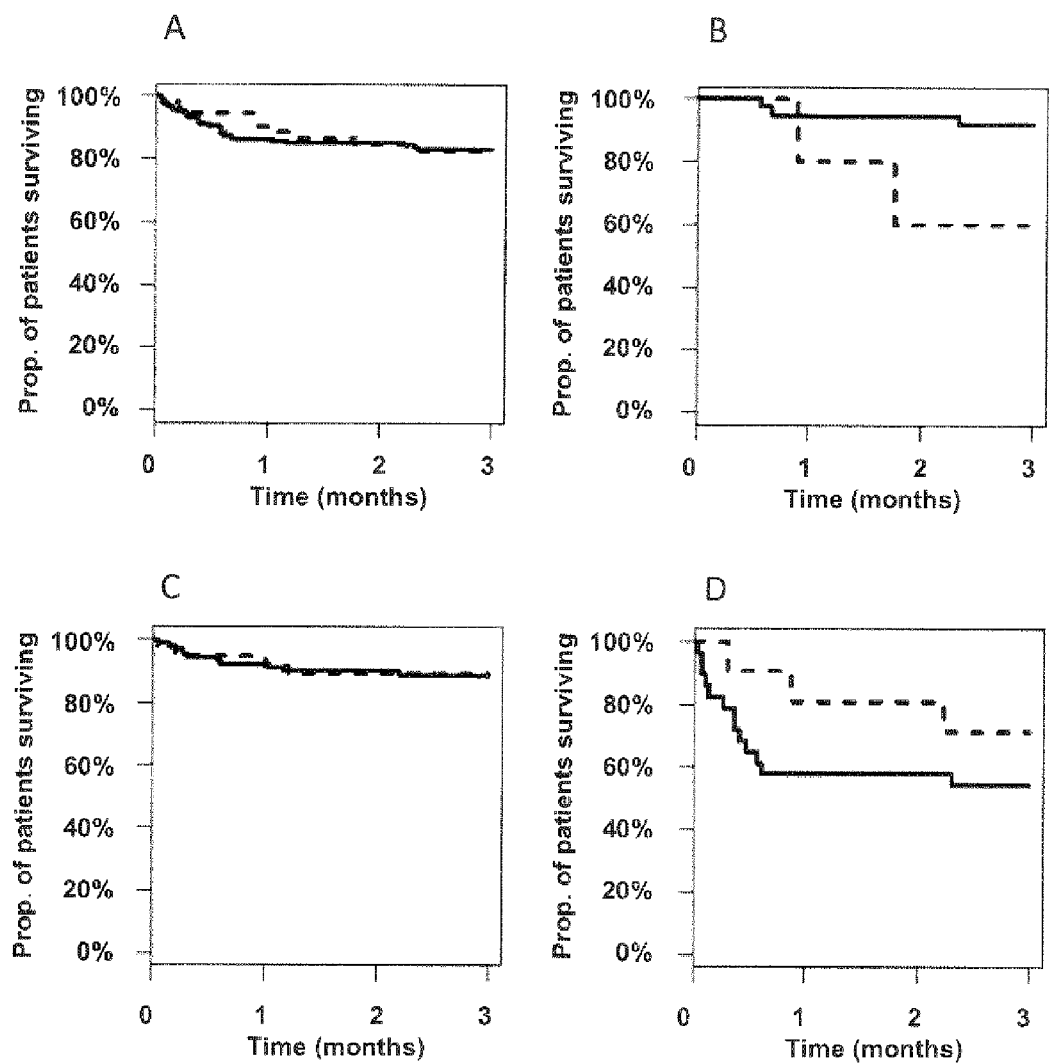
Figure 11:
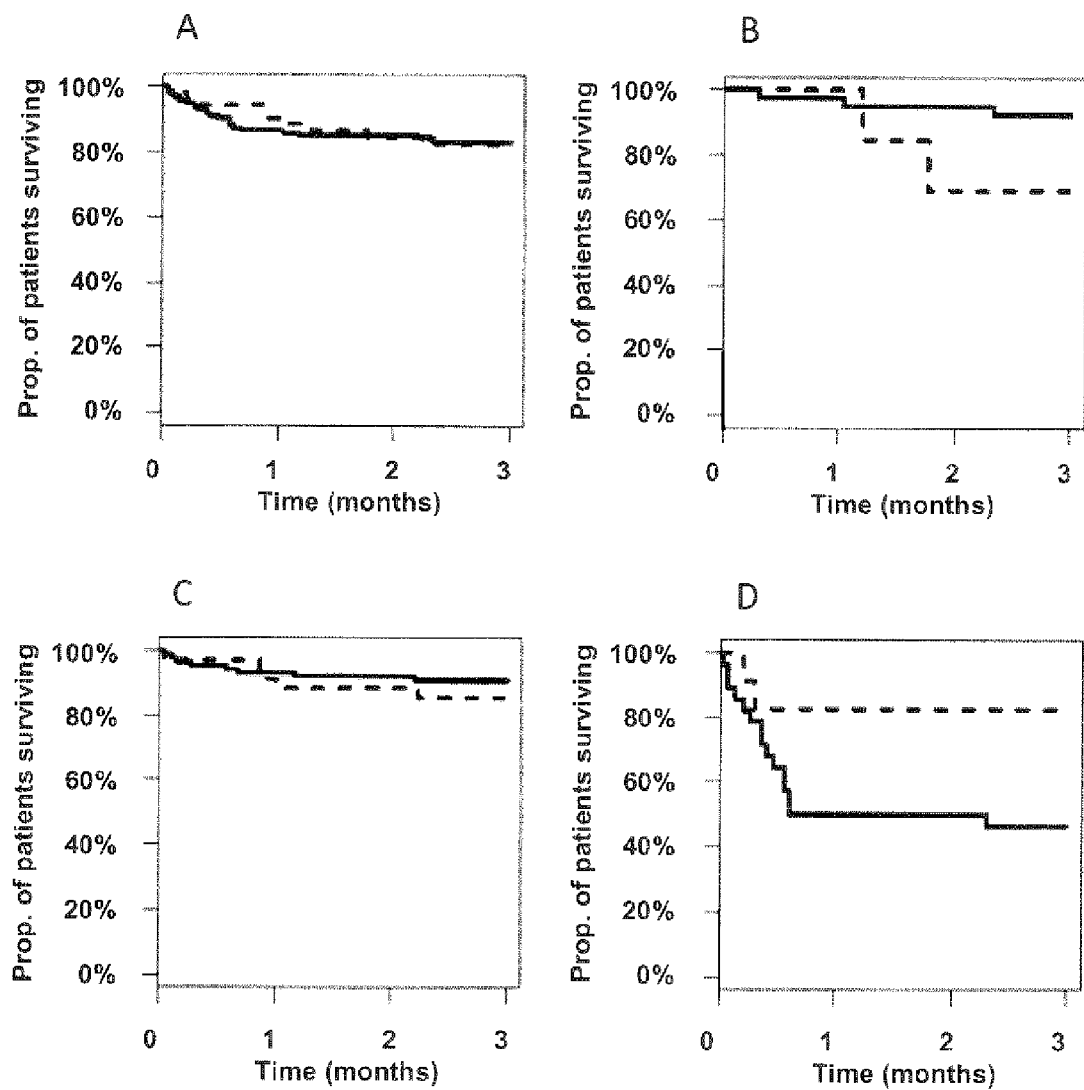
Figure 12:
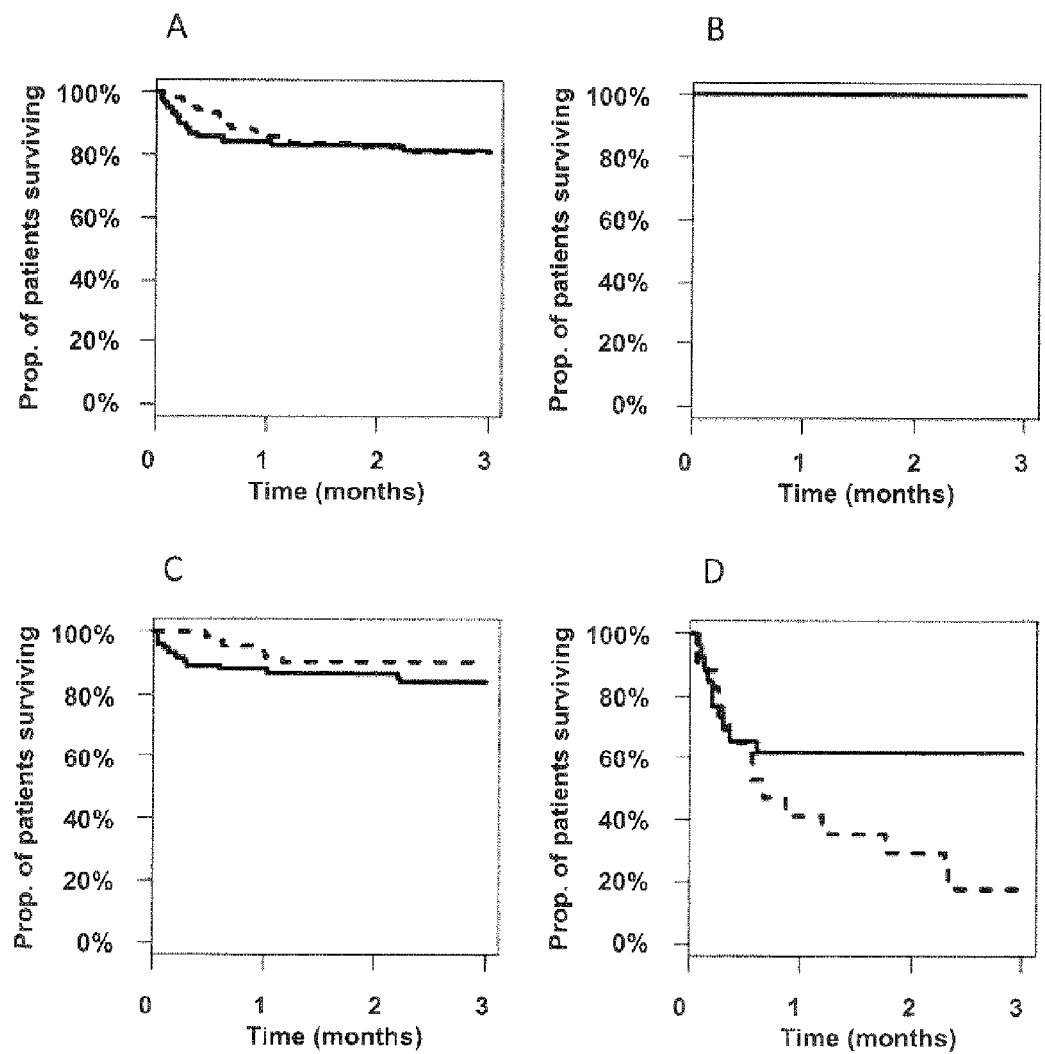
Figure 13:
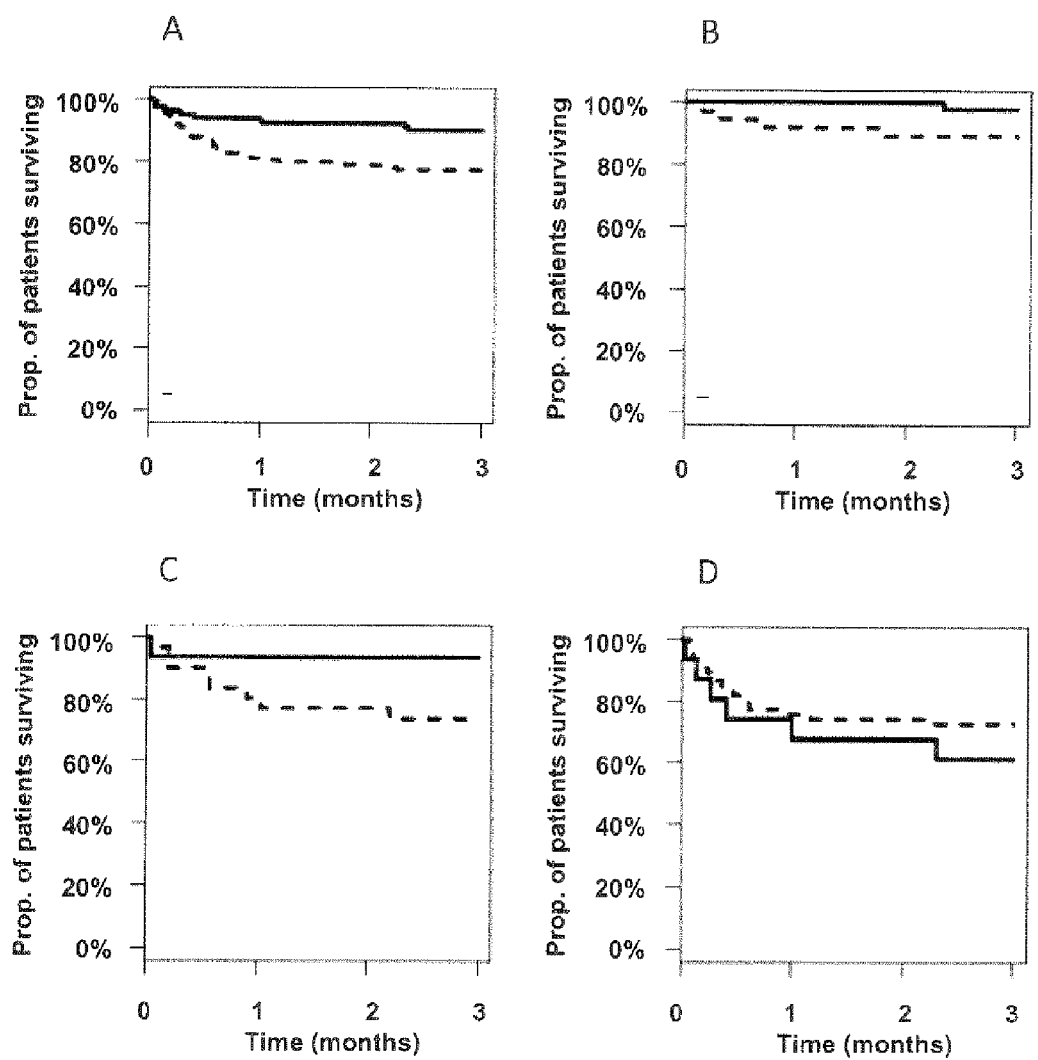
Figure 14:
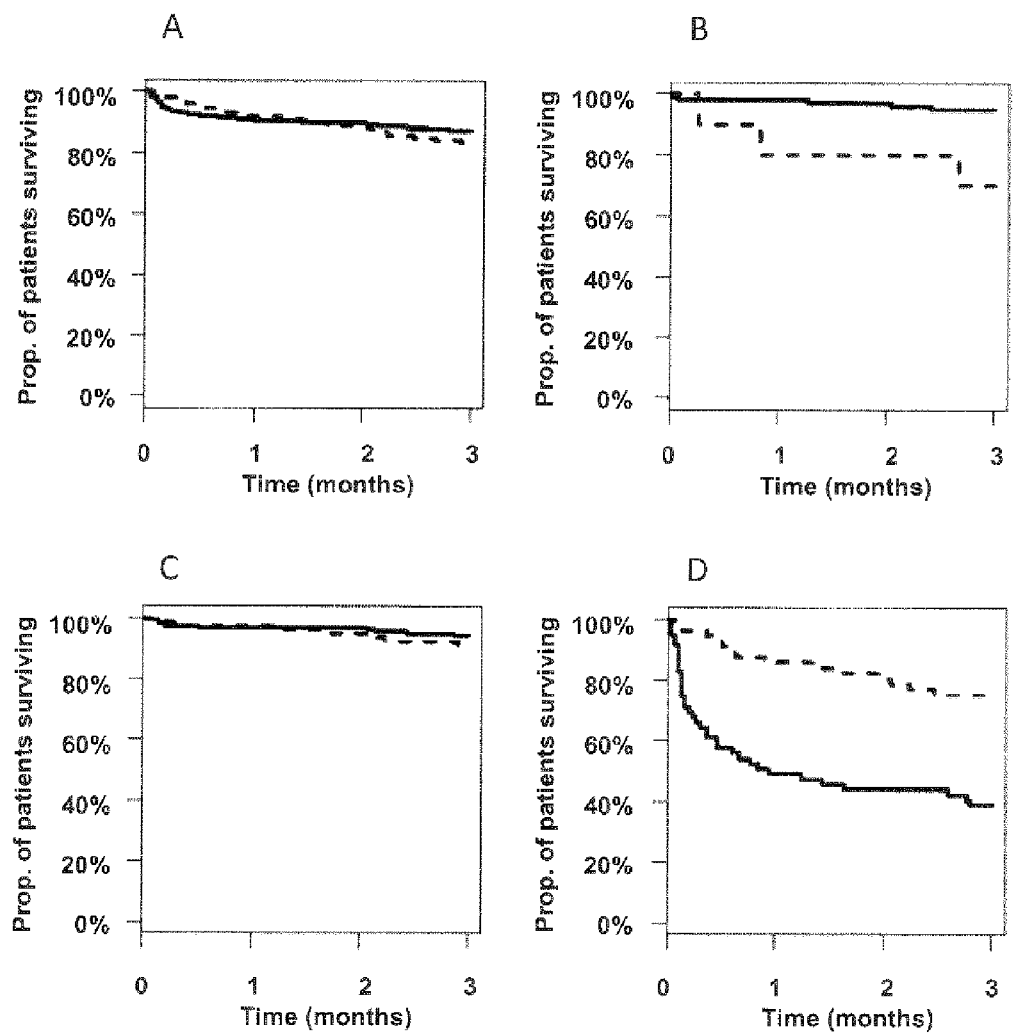
FIGS. 14 to 21 illustrate the survival rate for patients suffering from myocardial infarction from the "Leicester Acute Myocardial Infarction Peptide Study" ("LAMP").
Figure 15:
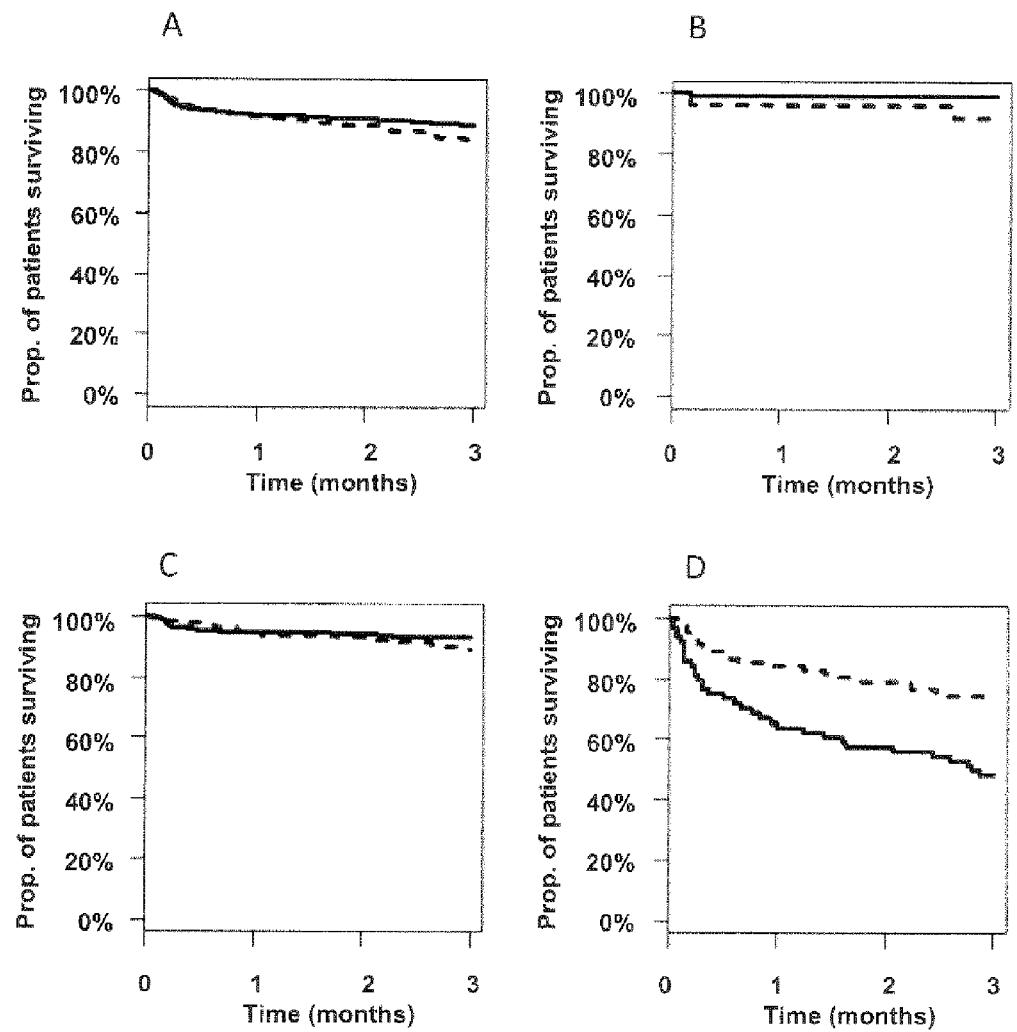
Figure 16:
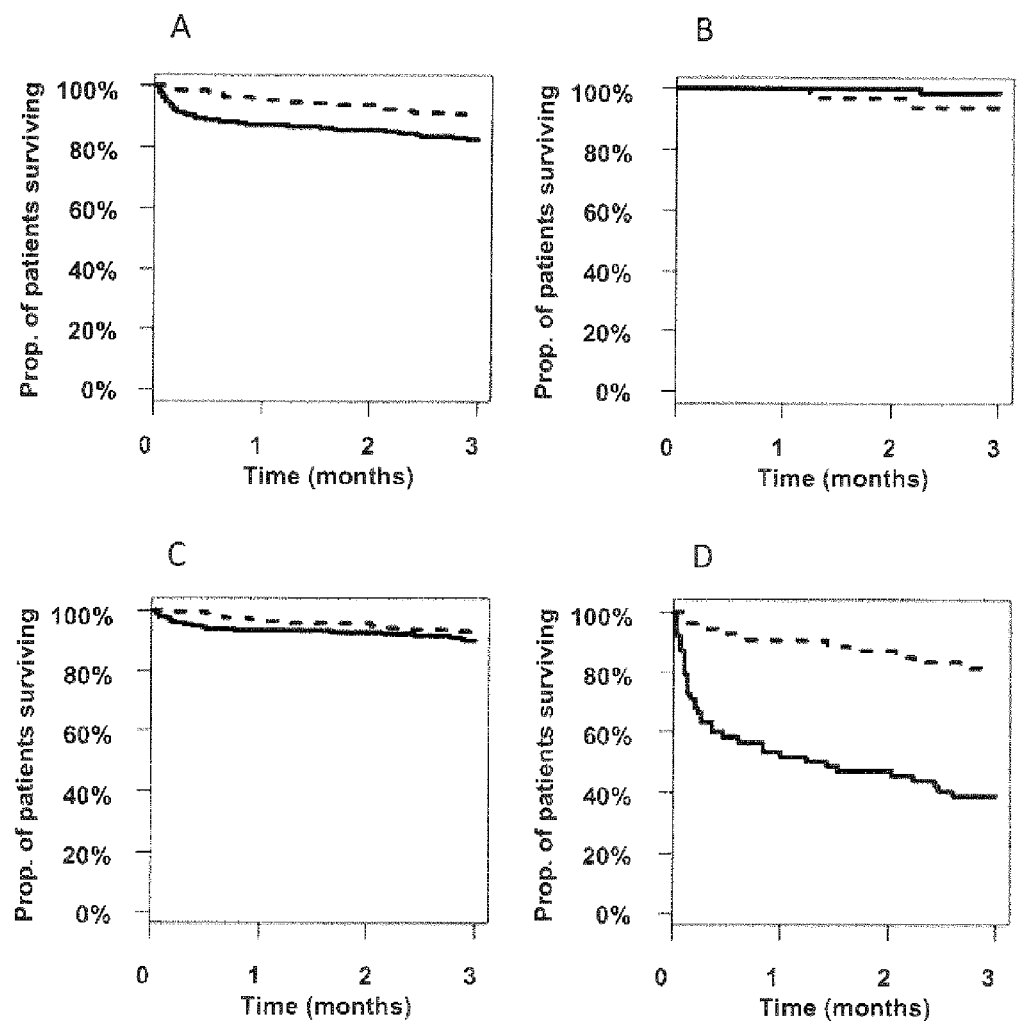
Figure 17:
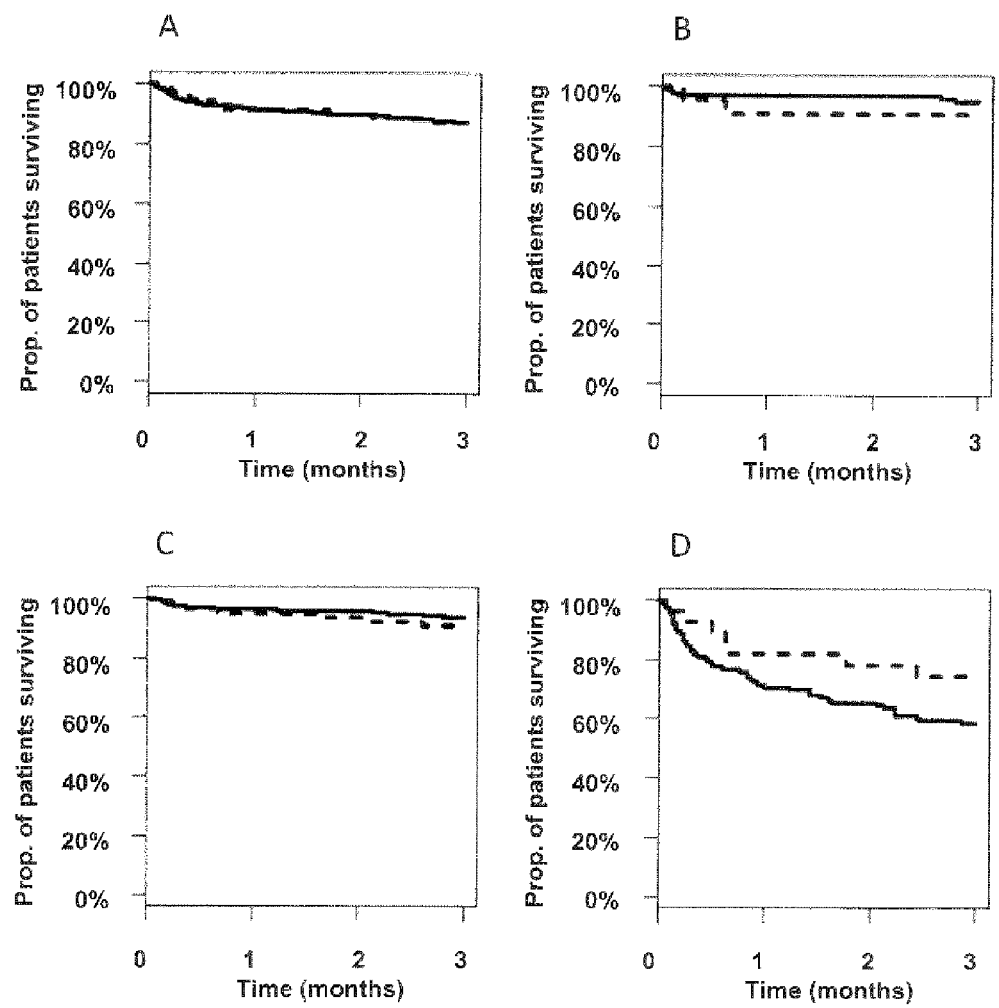
Figure 18:
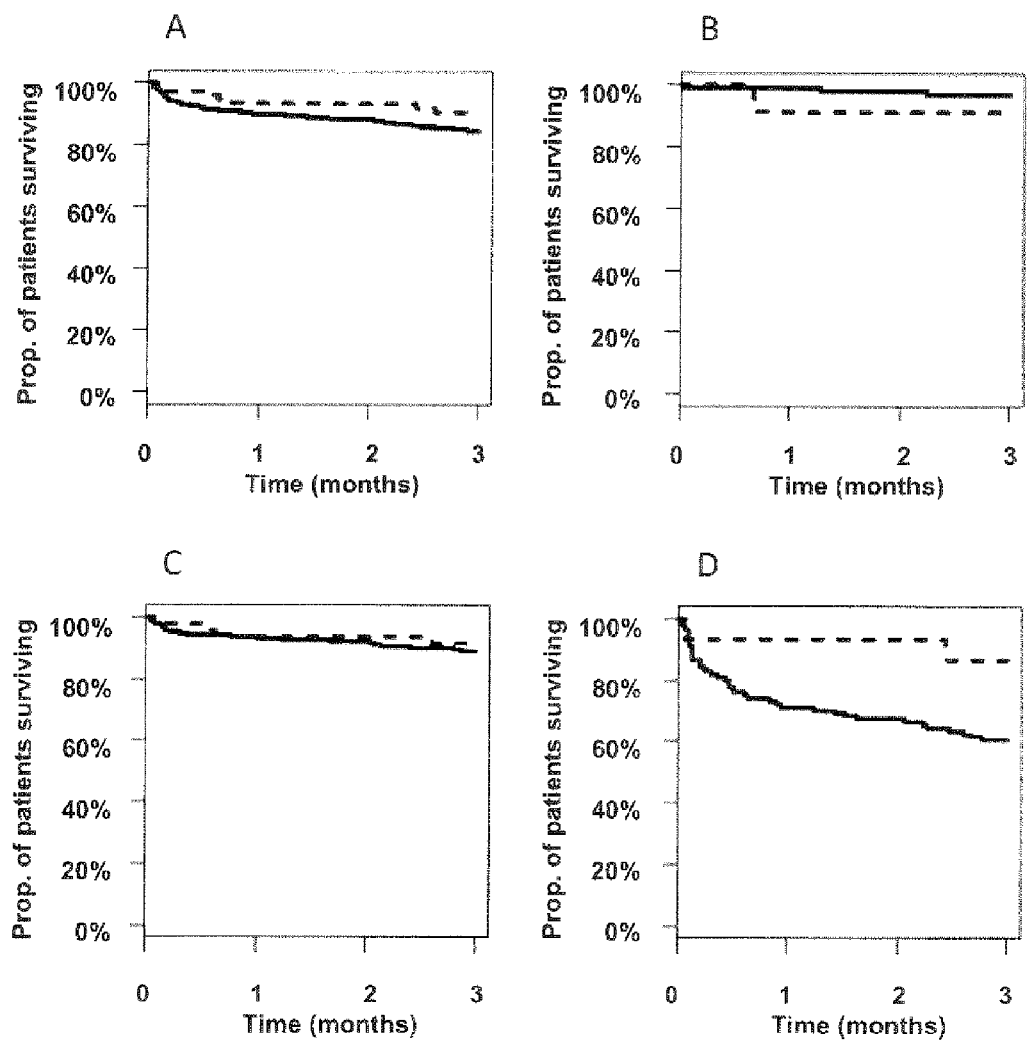
Figure 19:
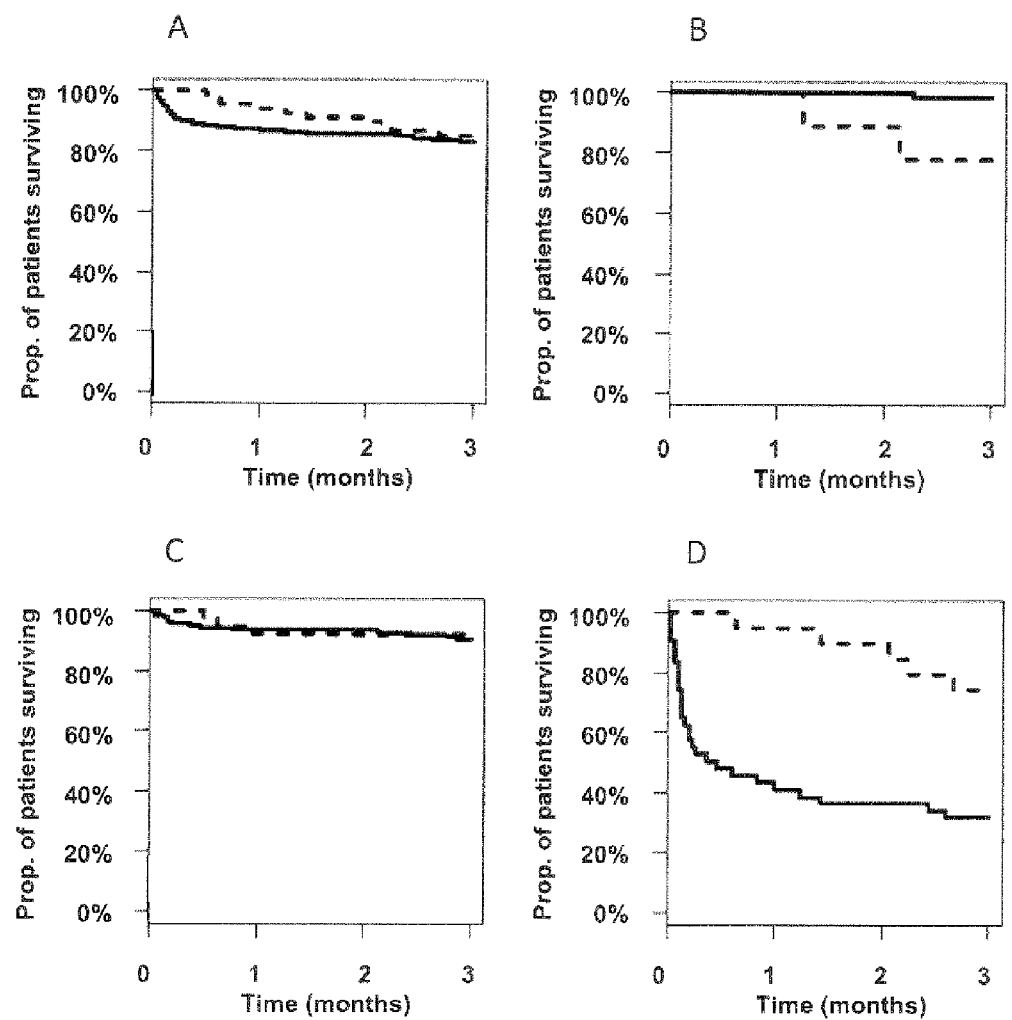
Figure 20:
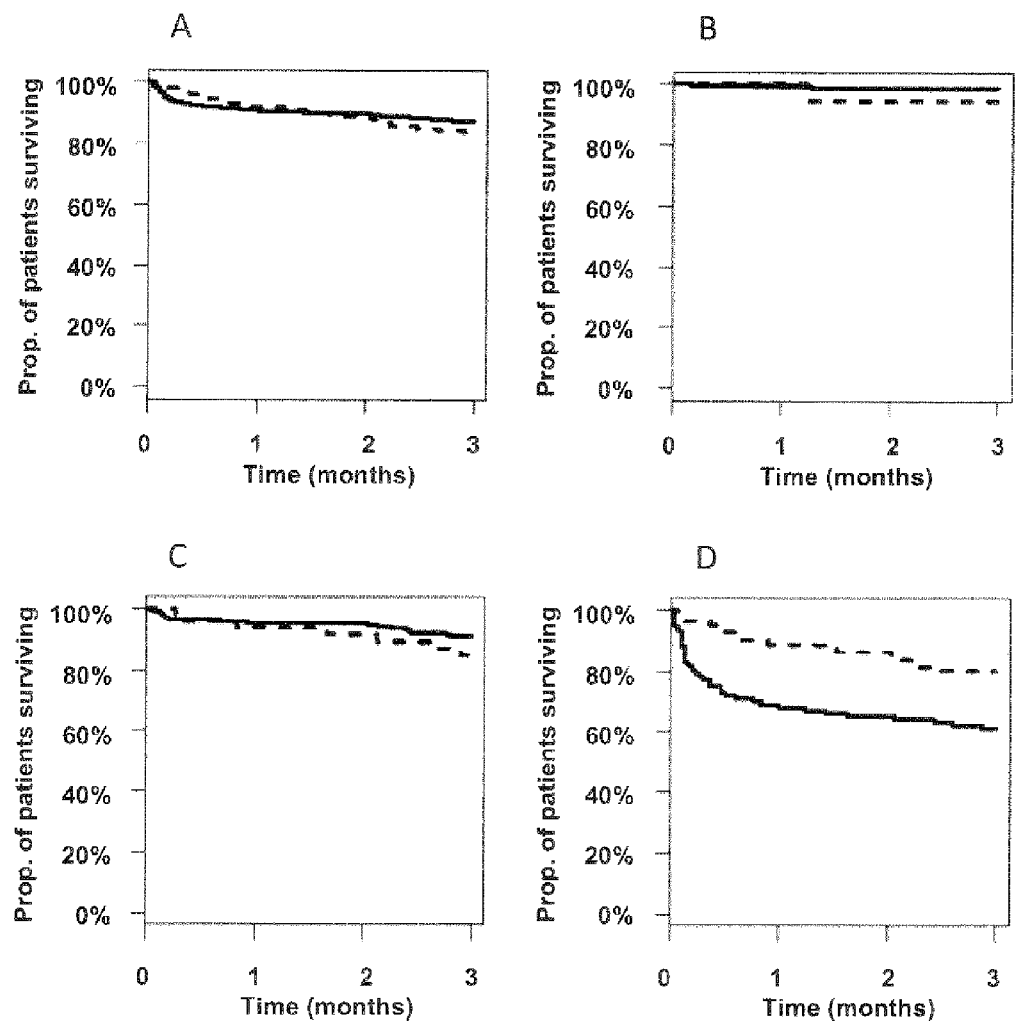
Figure 21:
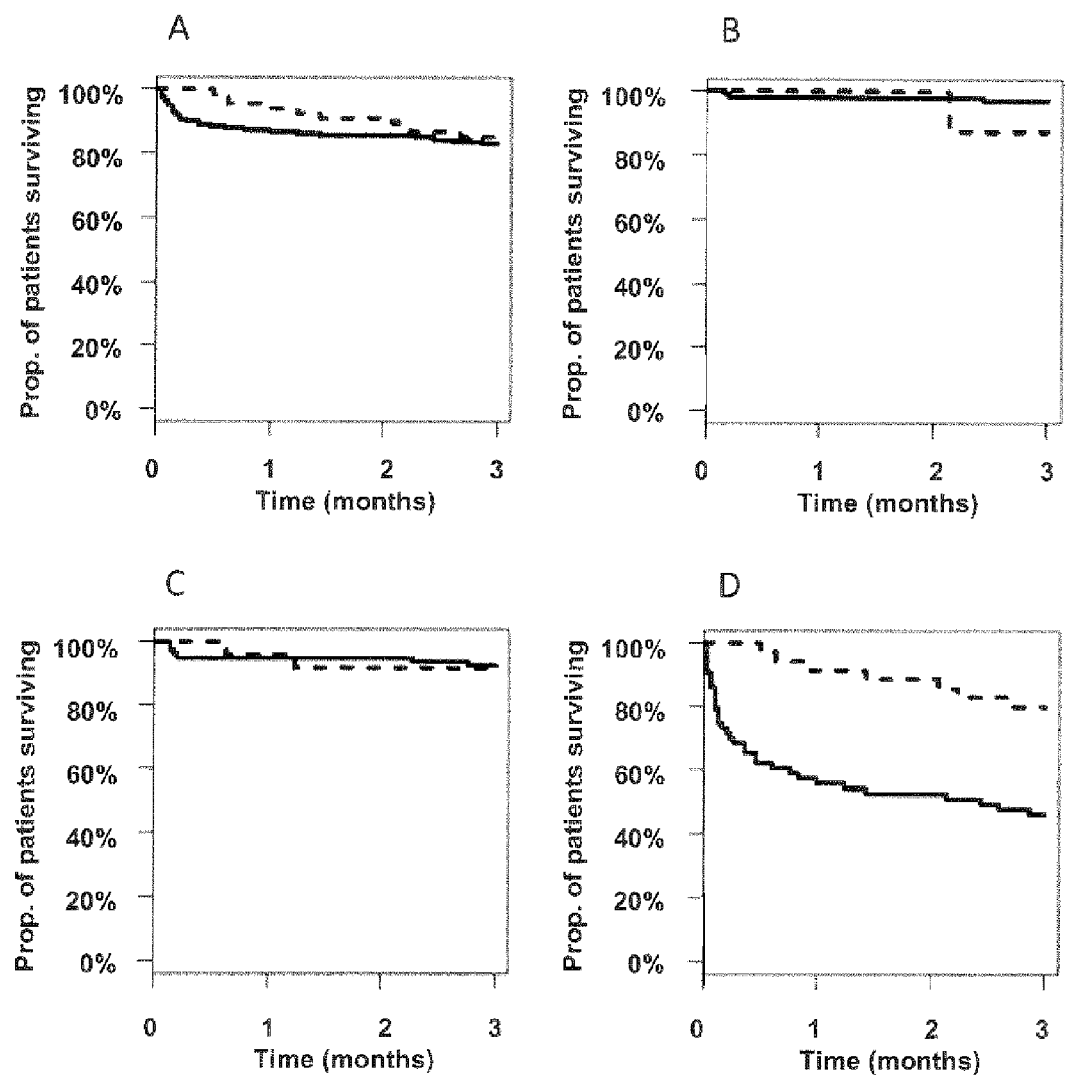
Figure 22:
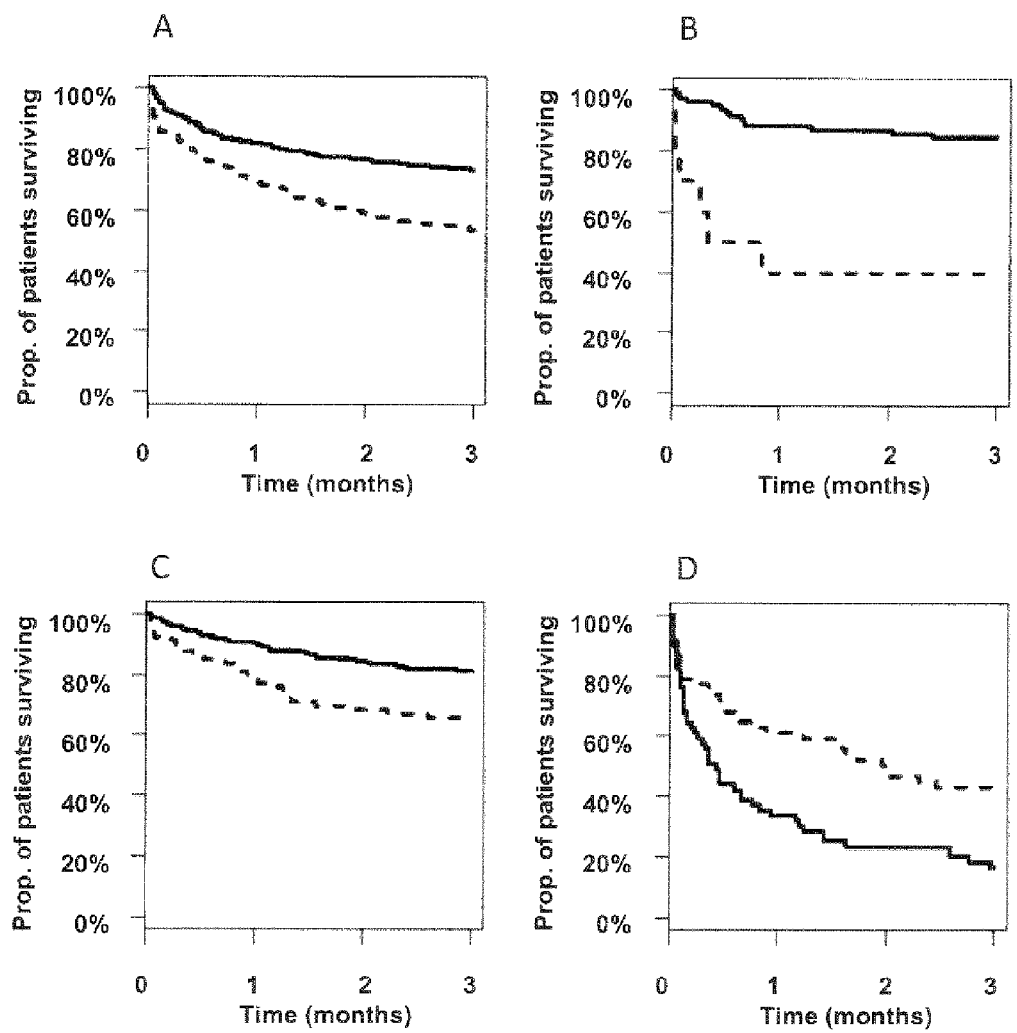
FIGS. 22 to 34 illustrate the rate of major cardiac events for patients suffering from acute myocardial infarction from "LAMP-Study".
Figure 23:
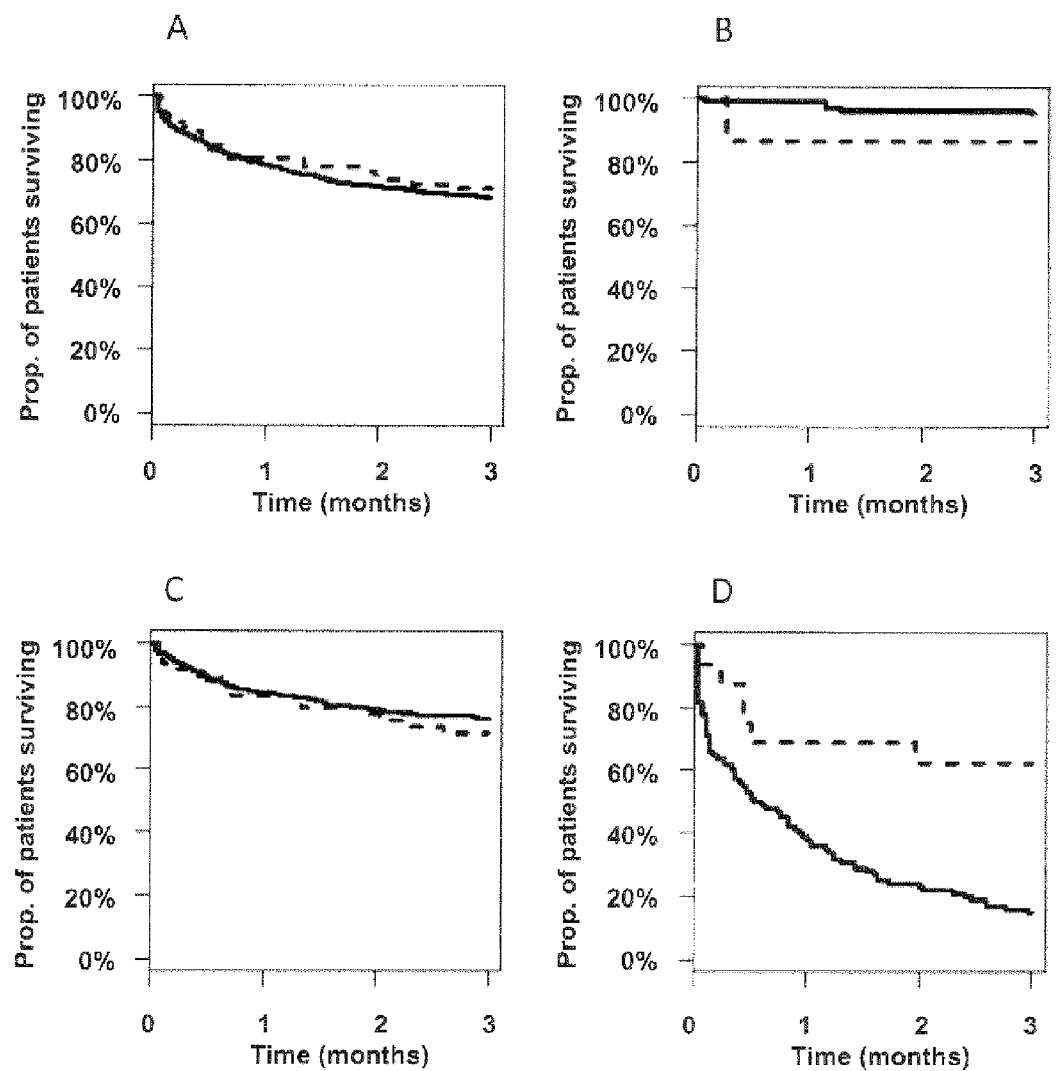
Figure 24:
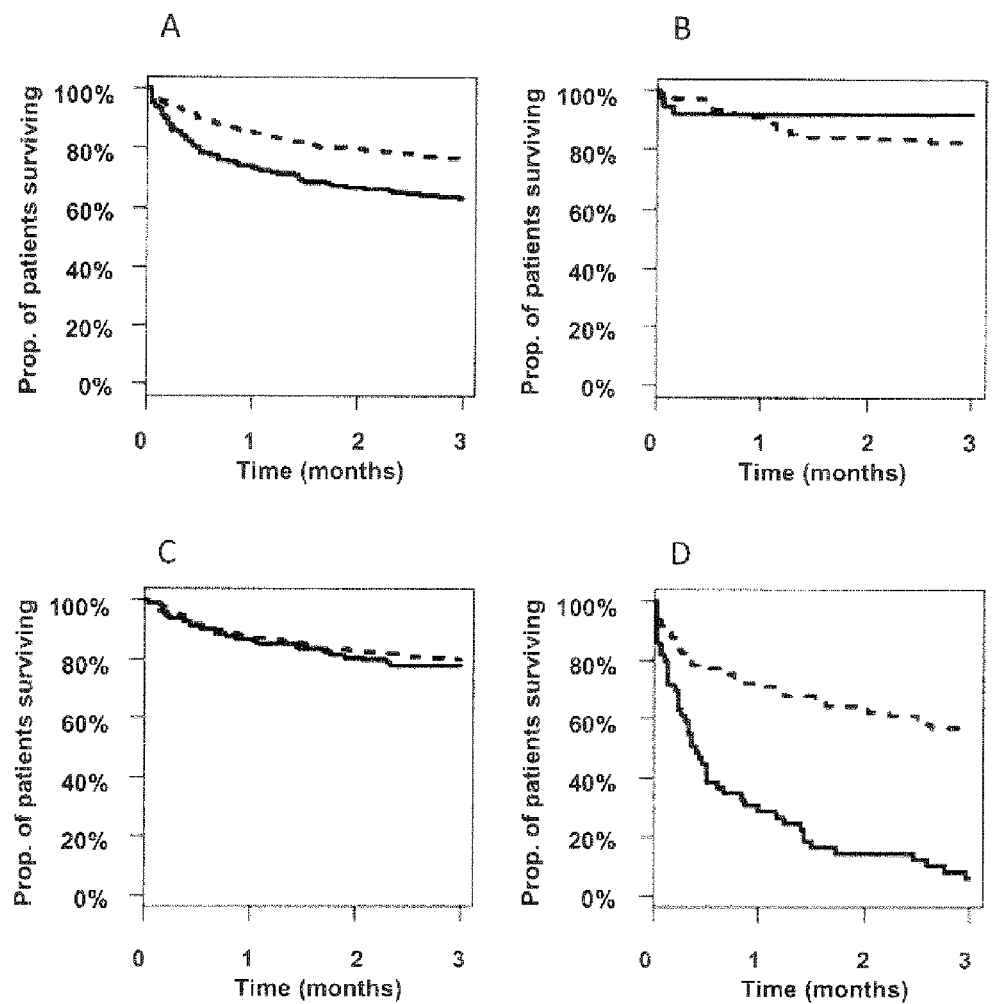
Figure 25:
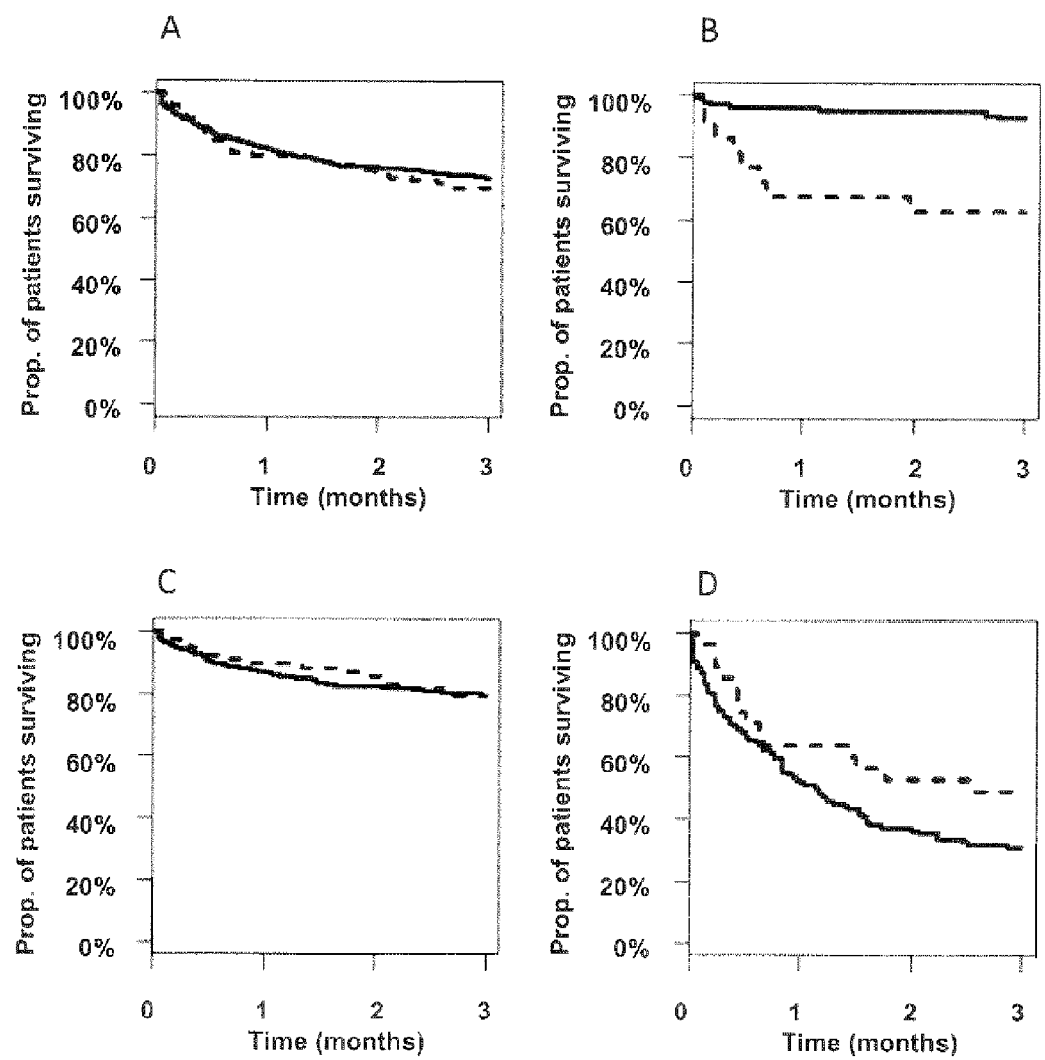
Figure 26:
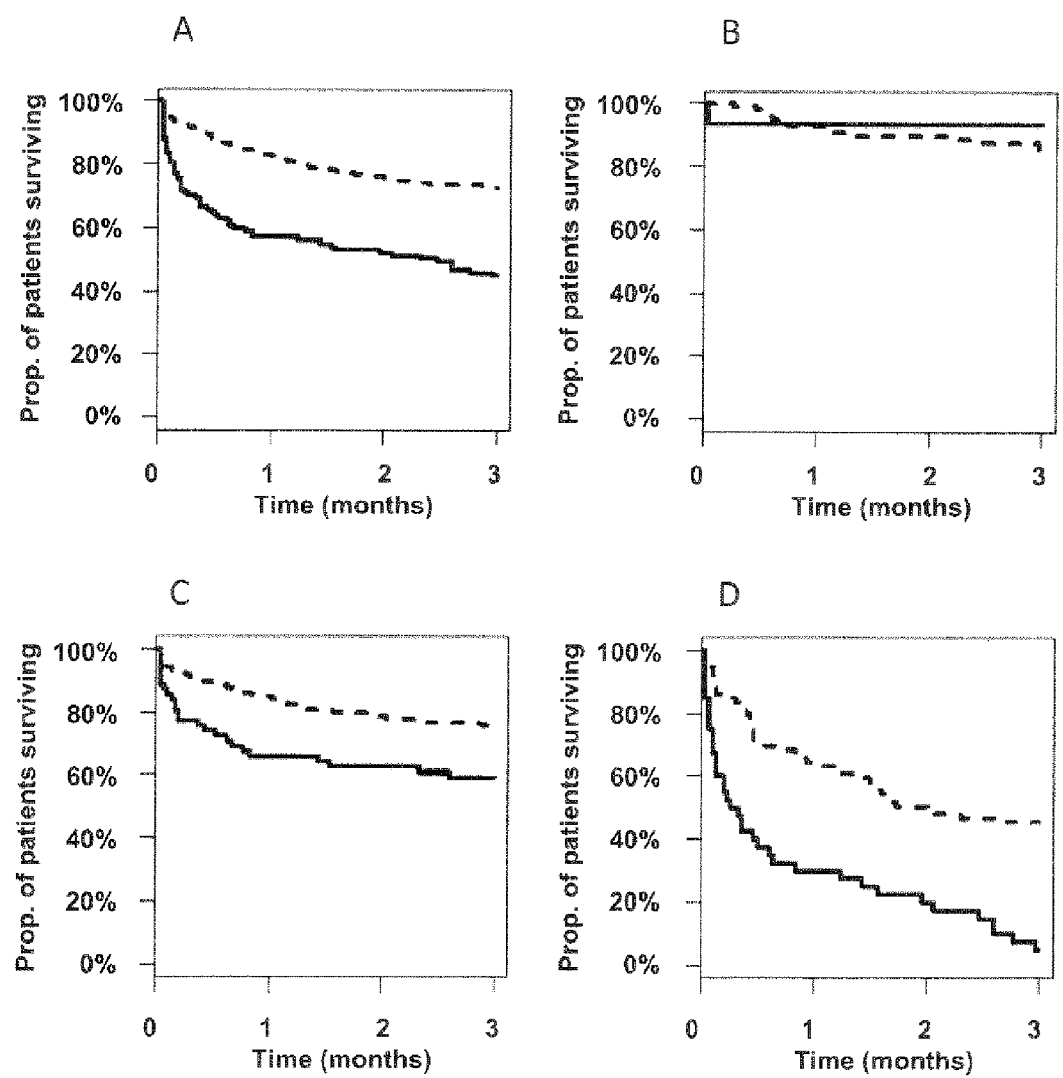
Figure 27:
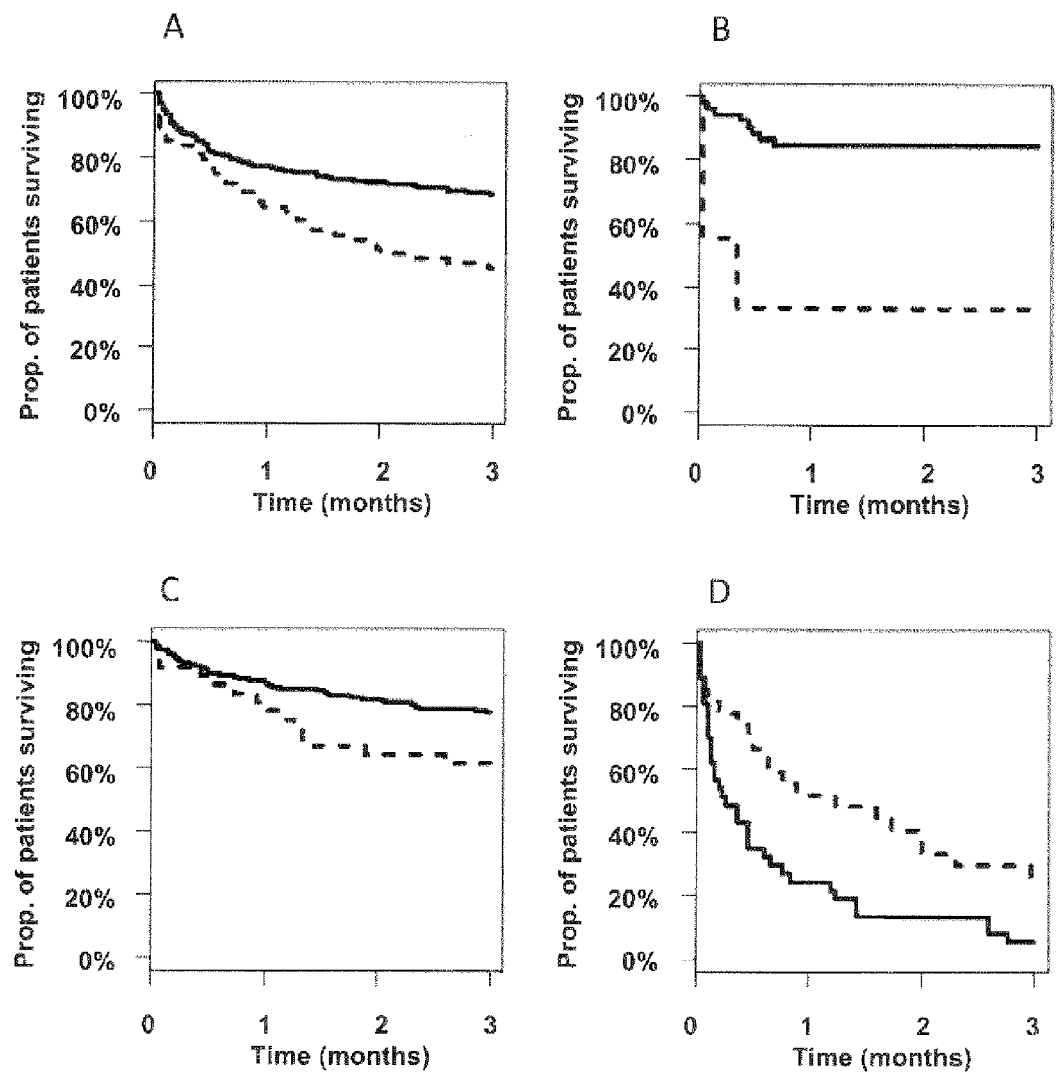
Figure 28:
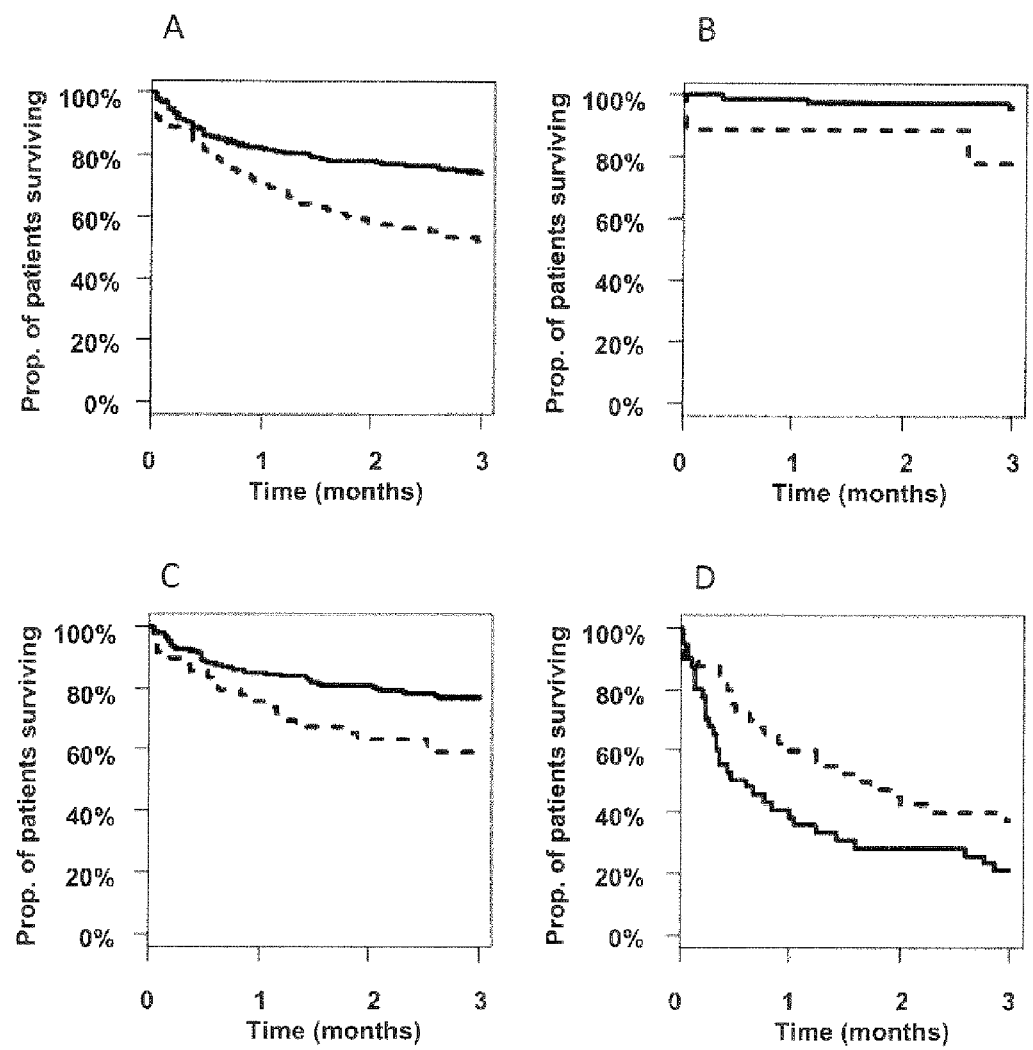
Figure 29:
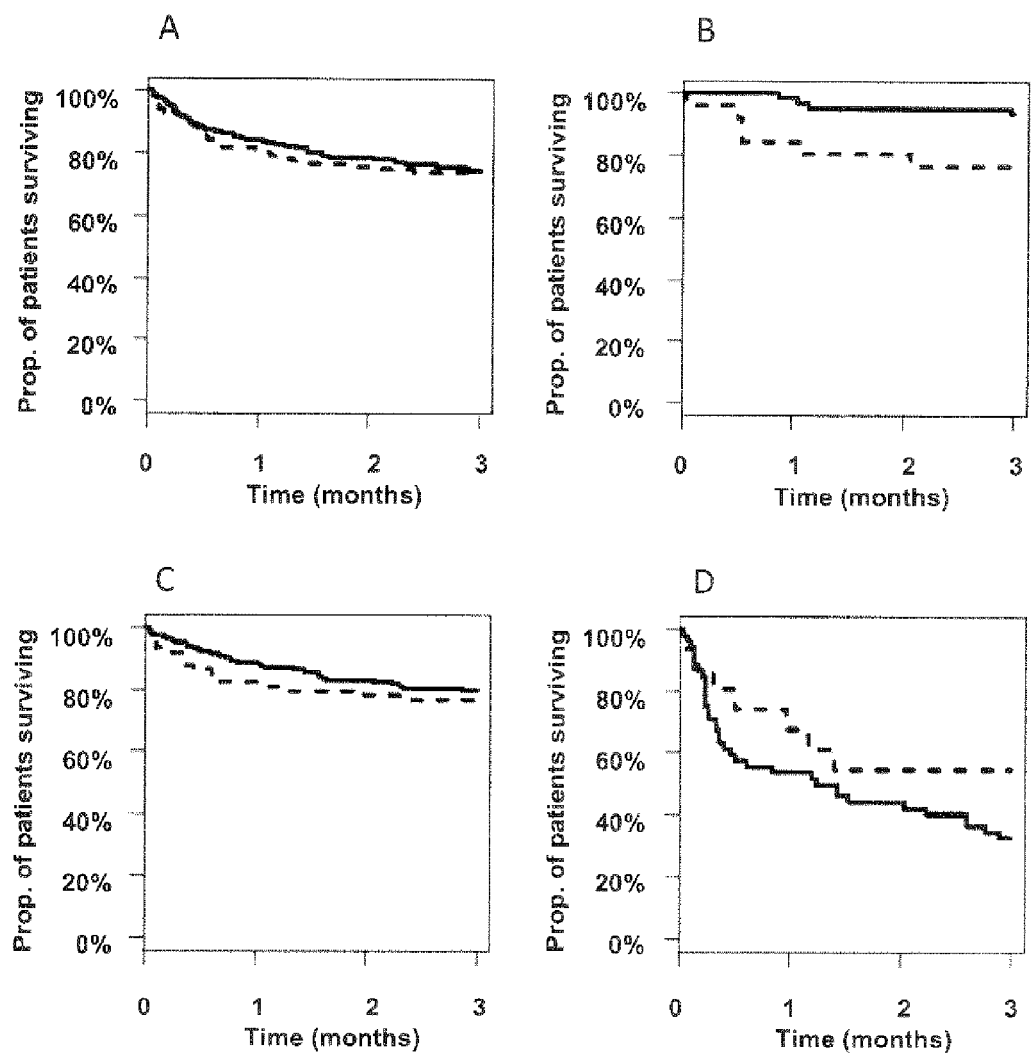
Figure 30:
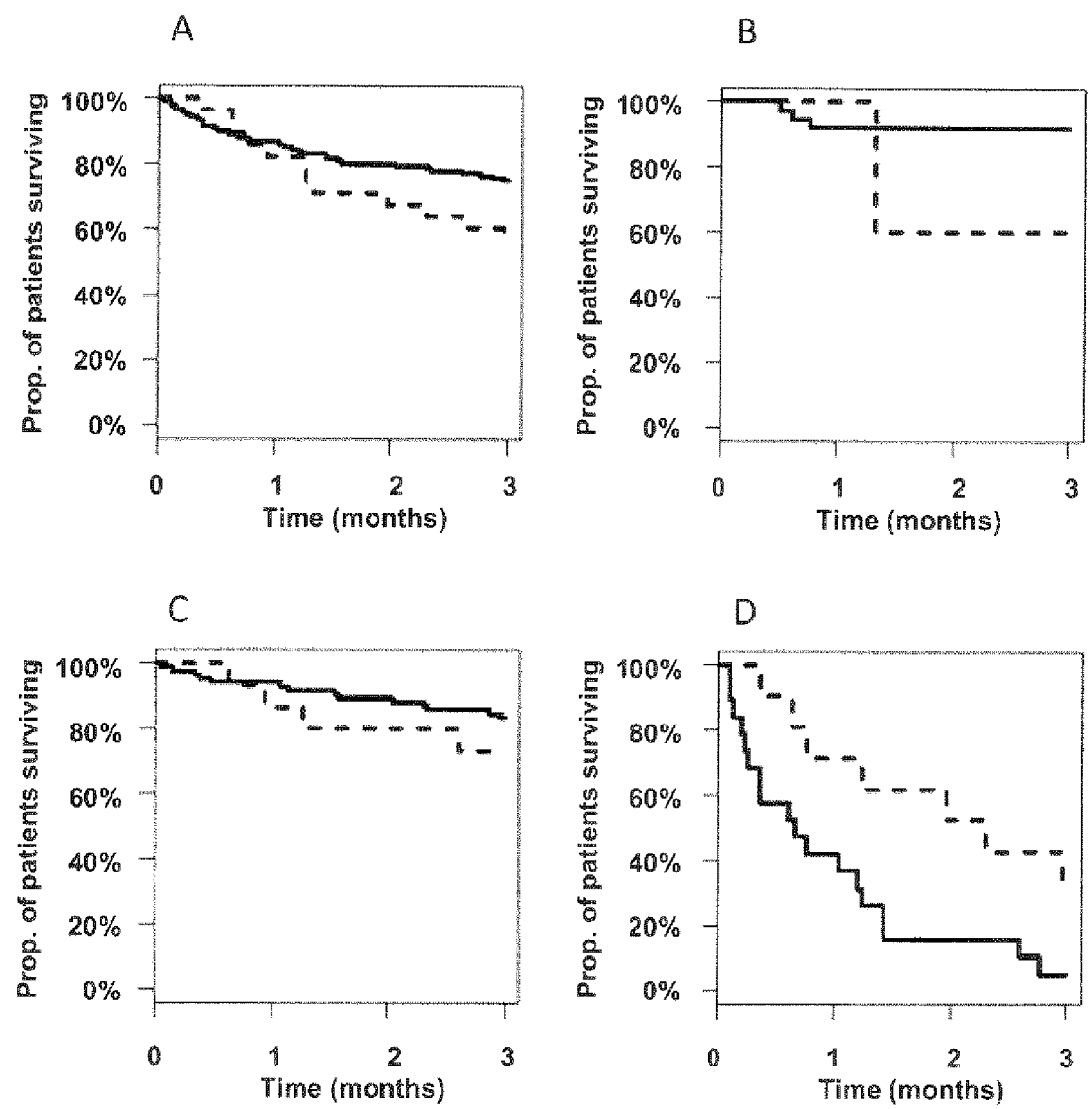
Figure 31:
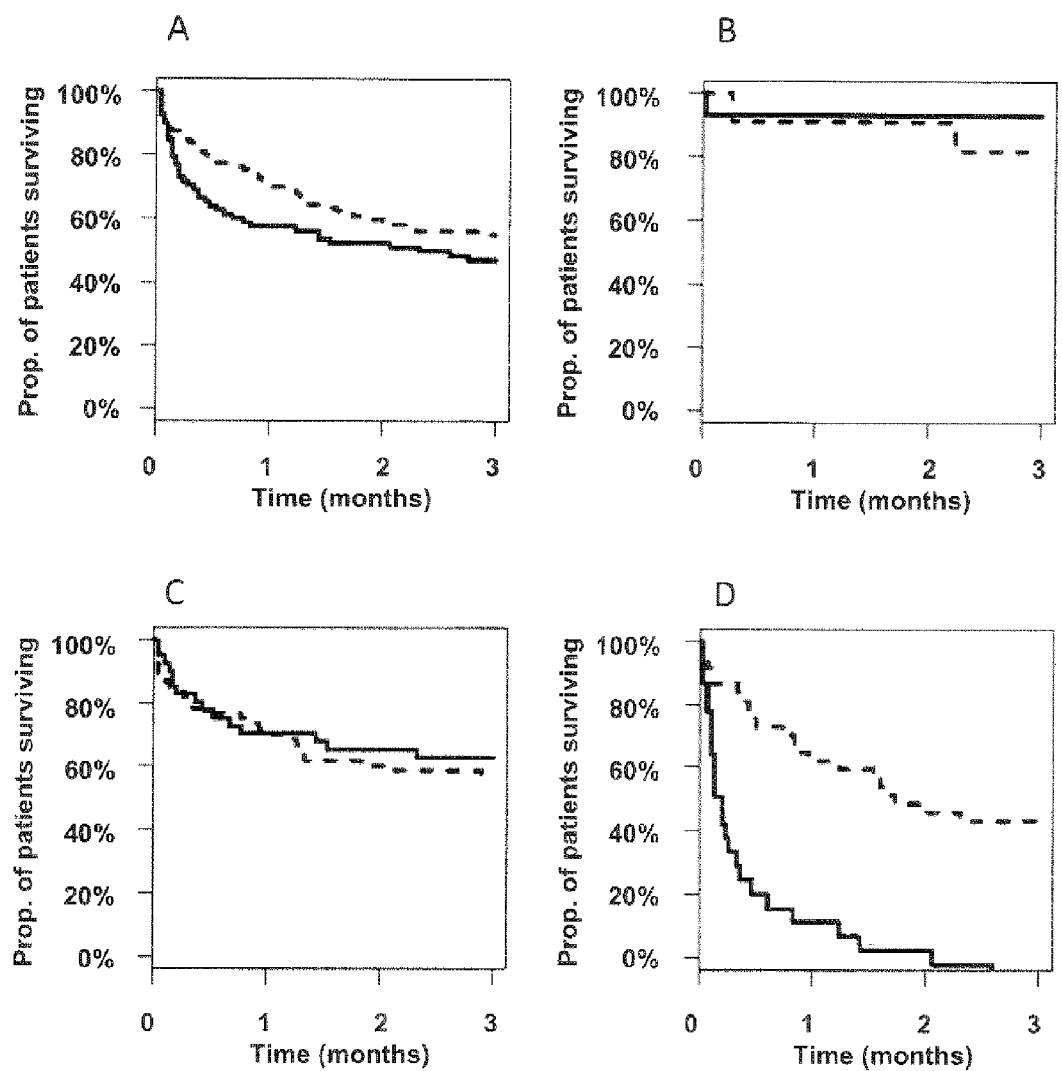
Figure 32:
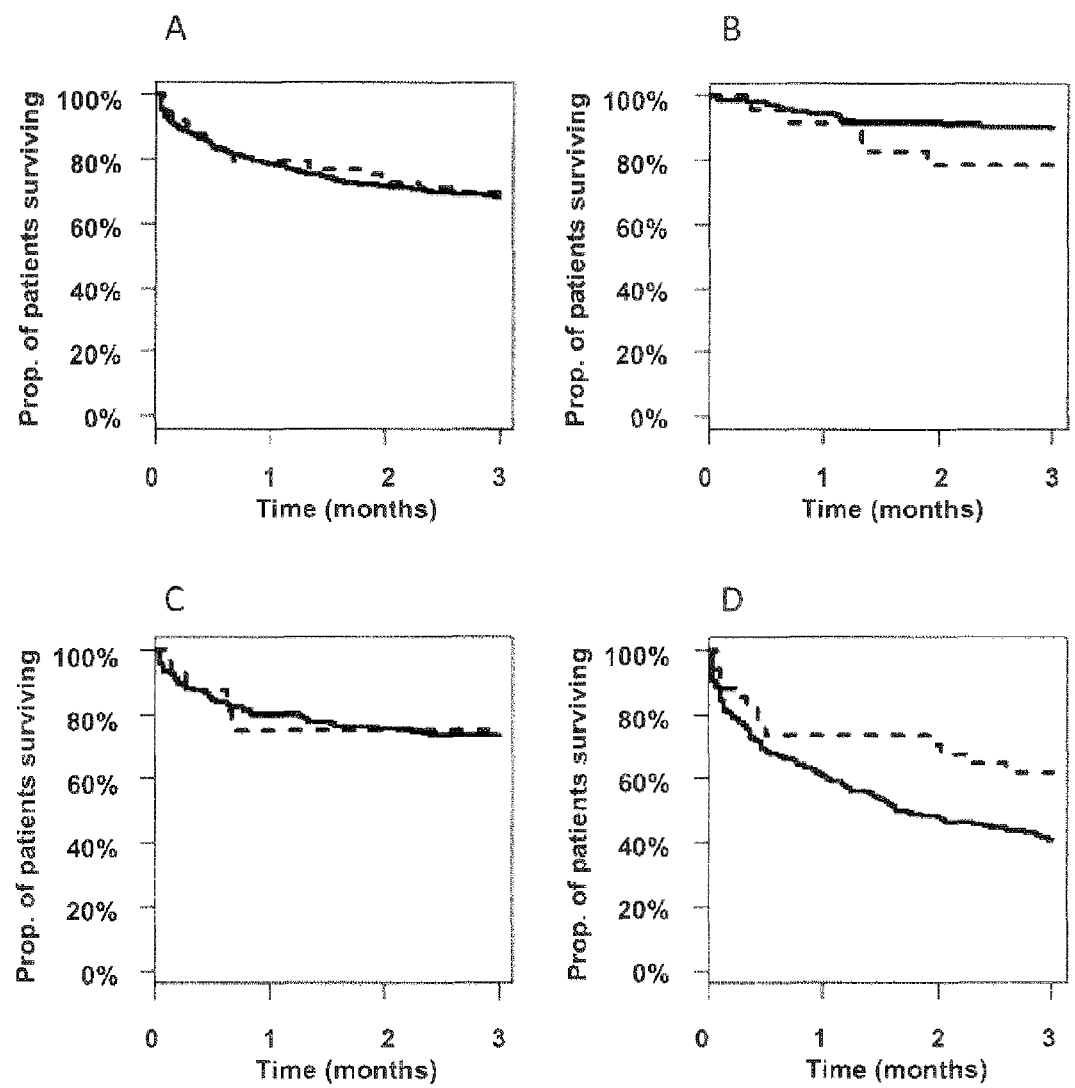
Figure 33:
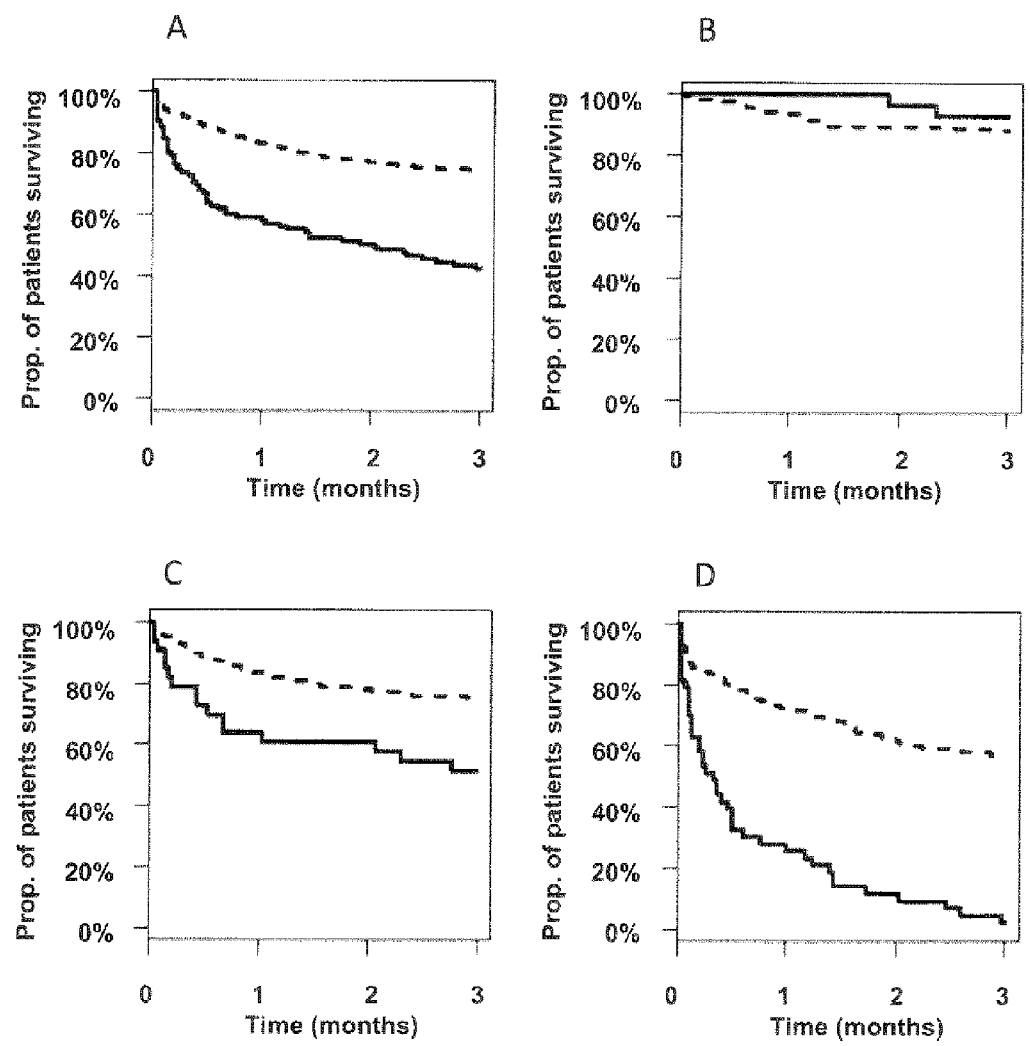
Figure 34:
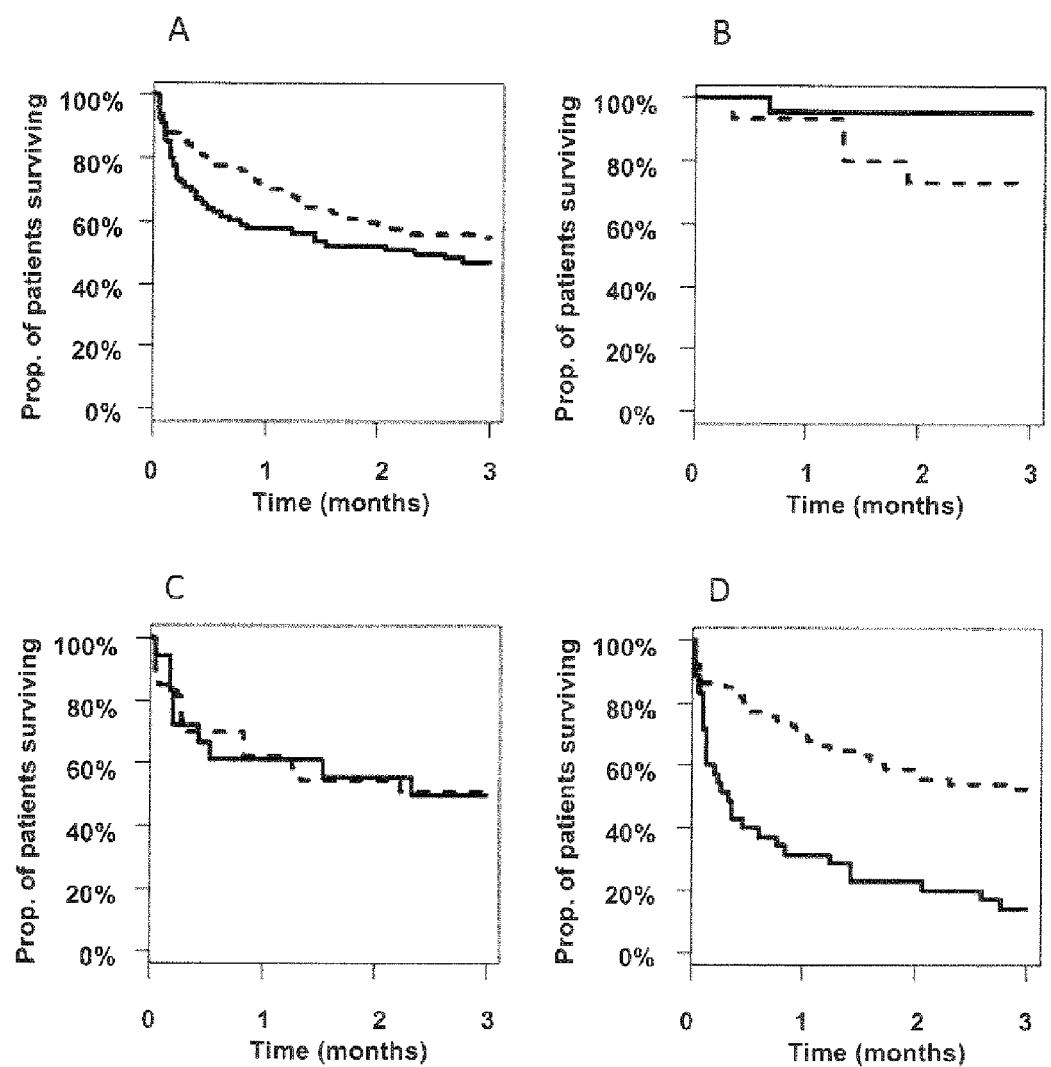

MR-proANP and MR-proADM were detected using novel fully automated sandwich immunoassay systems on the B.R.A.H.M.S KRYPTOR (B.R.A.H.M.S AG, Hennigsdorf/Berlin, Germany) (Caruhel et al. 2009. *Clin Biochem* 42: 725-8). This random access analyzer employs the sensitive Time Resolved Amplified Cryptate Emission (TRACE) technology, based on a non-radioactive-transfer between 2 fluorophores, europium cryptate and XL665. Both automated assays are based essentially on the sandwich chemiluminescence assays which are described in detail elsewhere (Morgenthaler et al. 2004. *Clin Chem* 50:234-6; Morgenthaler et al. 2005 *Clin Chem* 51:1823-9), and which were used in other studies (Khan et al. 2008. *J Am Coll Cardiol* 51:1857-64; Khan et al. 2007. *J Am Coll Cardiol* 49: 1525-32; van Haehling et al. 2009. *J Am Coll Cardiol. in press*; Gegenhuber et al. 2006. *Clin Chem* 52: 827-31).

For MR-proANP detection, 14 µl of patients' serum were incubated for 14 min. The measuring range was 0-10000 pmol/L, the limit of detection 2.1 pmol/L, and the limit of quantitation 4.5 pmol/L. The intra assay CV was 1.2% and the inter laboratory CV 5.4%. This assay uses the same antibody pair as the reference assay (Morgenthaler et al. 2004. *Clin Chem* 50: 234-6), and the correlation between the two assay systems was r=0.99.

For MR-proADM detection, 26 µl serum was incubated for 29 min. The measuring range was 0-100 nmol/L, the limit of detection and limit of quantification were 0.05 and 0.23 nmol/L, respectively. The intra assay CV was 1.9% and the inter laboratory CV was 9.8%. This assay uses the same antibody pair as described in detail elsewhere (Morgenthaler et al. 2005. *Clin Chem* 51: 1823-9), and the correlation between the two assay systems was r=0.99.

CT-proAVP (Copeptin) levels were measured with a chemiluminescence sandwich immunoassay with a lower detection limit of 1.7 pmol/L (Morgenthaler et al. 2006. *Clin Chem* 52:112-9). In 359 healthy individuals (153 men and 206 women), median CT-proAVP levels were 4.2 pmol/L ranging from 1.0-13.8 pmol/L. The inter laboratory CV was <20% and the intra assay CV was <10% for samples >2.25 pmol/L.

CT-proET-1 levels were measured with a chemiluminescence sandwich immunoassay with a lower detection limit of 0.4 pmol/L (Papassotiriou et al. 2006. *Clin Chem* 52: 1144-51). In 326 healthy individuals (150 male and 176 female) CT-proET-1 values followed a Gaussian distribution with a mean (SD) of 44.3 (10.6) pmol/L and a range of 10.5-77.4 pmol/L. The intra assay imprecision (CV) was <5% and the inter laboratory CV was <10%.

BNP was measured with Triage two-site immunoassay reagents (Biosite, San Diego, Calif.) formatted for Beckman Coulter instrumentation (Brea, Calif.). Performance in the laboratory included a limit of quantitation of 5.0 ng/L, within run imprecision (CV) of 1.5% and total imprecision (CV) of 3.0%.

NTproBNP was measured by electrochemiluminescence on the ElecSys 2010 analyzer (Roche Diagnostics, Indianapolis, Ind.). Performance in the laboratory included a limit of quantitation of 10.0 ng/L, within run imprecision (CV) of 1.5% and total imprecision (CV) of 3.0%.

Example 2

Clinical Studies

The present invention is based on patients and samples from the following clinical studies:
I) Post-Stroke Patients (COSMOS Study)
Study Setting, Inclusion/Exclusion Criteria The study was set at the emergency and neurological and neurosurgical clinic of the University Hospital of Basel. All consecutive patients who are admitted to the emergency department with an ischemic or hemorrhagic stroke or transient ischemic attack (TIA) according to the World Health Organization criteria with symptom onset within the last 3 days were included into the study. Patients without an informed consent were excluded.
Baseline Data Collection Access to data of all eligible patients that are not included into this study is important to avoid a selection bias. Thus, we will collect baseline data and information on inclusion and exclusion criteria in all eligible patients irrespective whether they are or are not included into the study. This will allow the comparison of baseline data of eligible patients who consented to participate with those who did not. Baseline data collection in patients will be collected by the investigators and contain:
a) age
b) gender
c) BMI
d) Medical history items: actual history that preceded the hospitalization; ABCD score (Rothwell et al. 2005. *A simple score (ABCD) to identify individuals at high early risk of stroke after transient ischaemic attack. Lancet* 366: 29-36) in patients with transient ischemic attack; family history; relevant co-morbidities also assessed by the charlson index (Goldstein et al. 2004. *Charlson Index comorbidity adjustment for ischemic stroke outcome studies. Stroke* 35: 1941-5) (i.e. hypertension, previous stroke, previous TIA, ischemic heart disease, atrial fibrillation, diabetes mellitus, renal and liver dysfunction, congestive heart failure, dyslipidemia; comorbidities with the risk of hyponatremia (severe hypothyroidism, glucocorticoid insufficiency, neoplasm, HIV infection); smoking history (pack-years) and status (pack per day); current medication; alcohol consumption (glass and grams per day); time from onset of symptoms to admission.
e) Place of residence: i.e. independent living, defined as living at home or in an old people's home with or without support of the family circle and/or professional care (the family circle consists of the spouse and/or other important persons who live together with the patient; dependent living, defined as nursing home long-stay department, other hospital.
f) Clinical items: physical examination including neurological status, NIHSS (to assess the severity of stroke) and Glasgow Coma scale (GCS; Adams et al. 1999. *Baseline NIH Stroke Scale score strongly predicts outcome after stroke: A report of the Trial of Org* 10172 *in Acute Stroke Treatment (TOAST). Neurology* 53: 126-31), blood pressure, pulse rate, weight, volume status (including skin turgor, jugular venous distension, auscultation, if available flow sheet of fluid intake and loss), body temperature; in neurosurgical patients intracerebral pressure if performed within the routine clinical management.
g) Clinical symptoms of hyponatraemia will be evaluated on admission and in case of sodium imbalance in neurological patients. In patients undergoing intracranial surgery we will evaluate clinical symptoms daily. Specifically we will monitor the presence of headache, anorexia, nausea, vomiting, muscle cramps and aches, seizures, confusion, apathetic or lethargic development.
h) Routine/Standard laboratory tests: routine blood sampling including: hematocrit, blood urea nitrogen, bicarbonate, total protein, albumin, uric acid serum and urine electrolytes, urine and serum osmolality, creatinine, lipids, TSH, fT4, T3, and basal cortisol. All blood sampling will be done before any food intake, or smoking, if feasible. Alternatively, influencing factors will be monitored.
i) Imaging: Computer tomography or MRI of the neurocranium (T1, T2, diffusion-weighted image sequence, with or without contrast), if indicated magnetic resonance angiography or conventional cerebral angiography. We will record the time-points of contrast agent application.

Stroke patients will also be classified on the basis of the vascular territory of the ischemic lesion as follows: total anterior circulation syndrome (TACS), partial anterior circulation syndrome (PACS), lacunar circulation syndrome (LACS), posterior circulation syndrome (POCS).
j) Further investigations: Stroke patients will have neurosonography, echocardiography, standard 12-leaf electrocardiography and 24-hour electrocardiography and then will be classified by etiology of strokes according to Trial of Org 10172 in acute Treatment (TOAST) stroke subtype classification, which differs between large artery atherosclerosis, cardioembolism, small-artery occlusion, other etiology, and undetermined etiology.
Informed Consent Statement The study will be approved by the ethics committee of Basel (Ethikkommission beider Basel). It is important to note that this is an exploratory and observational study; the only study related intervention will be the asseveration of 7.5 ml of plasma obtained during the routinely performed blood sampling. Therefore, patients are required to provide written informed consent that they agree for the use of their data for scientific purposes. In patients, in which "informed consent" is not feasible due to sequela of the acute CNS lesion (the latter a prerequisite for inclusion), patients' next to kin can sign an assent form to state the presumptive will of the patient. In case, next of kin are not readily available, a treating physician—who must not be involved in the study—have to certify that there are no objections for inclusion in the study from his point of view. Only after these informed consent procedures the patient can be included in the study.
Management of Participants Throughout the Trial
Step 1. All eligible patients in the emergency department or the neurological ward will be included into the study.
Step 2. All baseline data will be collected.
Step 3. During hospitalization we Clinical items including weight, blood pressure, pulse rate, volume status and body temperature will be assessed by chart review until discharge.
  Fluid treatment and drugs.
  Potential symptoms of hyponatremia, i.e. headache, nausea, vomiting, muscle cramps and aches, anorexia, impaired consciousness, seizure.
  Routinely performed laboratory tests (chemogramm, plasma glucose, serum osmolality, urine osmolality, sodium in urine, hematocrit) will be sampled at the time-points when blood sampling is routinely done on the wards.
Step 4. In all patients, on day 5 of the hospitalization, a clinical examination with NIHSS, Barthel Index and Ranking Scale will be performed (Collin et al. 1988. *The Barthel ADL Index: a reliability study. International Disability Study* 10:

61-3; Bonita and Beaglehole. 1988. *Modification of Ranking Scale: Recovery of motor function after stroke. Stroke* 19: 1497-1500).

The future place of residence (i.e. dependent vs. independent living) will be assessed.

Step 5. In patients with ischemic stroke a telephone follow-up regarding morbidity and mortality (as assessed by the Barthel Index and Ranking Scale) will be obtained after 3 months. An unfavorable outcome will be defined as a Barthel index <85 or modified Ranking scale of 3 to 6.

II) Post-Myocardial Infarction (MI) Patients (Leicester Acute Myocardial Infarction Peptide Study ("LAMP"))

Study Population:

The study involved 983 consecutive patients with acute myocardial infarction (AMI) admitted to the Coronary Care Unit of Leicester Royal Infirmary. Acute myocardial infarction was diagnosed if a patient had a plasma creatinine kinase-MB elevation greater than twice normal or a cardiac Troponin I level >0.1 ng/ml with at least 1 of the following: chest pain lasting >20 min or diagnostic serial electrocardiographic changes consisting of new pathological Q waves or ST-segment and T-wave changes. Acute myocardial infarction was subcategorized into ST-segment elevation myocardial infarction (STEMI) or non-ST-segment myocardial infarction (NSTEMI).

The study complied with the Declaration of Helsinki and was approved by the local ethics committee. Written informed consent was obtained from all patients.

Exclusion criteria were known malignancy, or surgery in the previous month. The estimated glomerular filtration rate (eGFR) was calculated from the simplified formula derived from the MDRD (Modification of Diet in Renal Disease) study, recently validated in patients with HF (Smilde et al. 2006. *Drawbacks and prognostic value of formulas estimating renal function in patients with chronic heart failure and systolic dysfunction. Circulation* 114: 1572-80).

Plasma Samples:

Blood samples were drawn on 1 occasion 3 to 5 days after the onset of chest pain. After 15 min bed rest, 20 ml blood was collected into tubes containing ethylendiaminetetraacetic acid (EDTA) and aprotinin. All plasma samples were stored at −70° C. until assayed in a blinded fashion in a single batch. In a subgroup of 132 patients from the original 983-patient cohort, blood sampling was performed daily for 5 days from admission to discharge.

Echocardiography:

Transthoracic echocardiography was performed in patients using Sonos 5500 instrument (Philips Medical Systems, Reigate, UK). Left ventricular ejection fraction was calculated using the biplane method of discs formula (Schiller et al. 1989. *Recommendations for quantitation of the left ventricule by two-dimensional echocardiography. American Society of Echocardiography committee on standards, subcommittee on quantitation of two-dimensional echocardiograms. J Am Soc Echocardiogr* 2: 358-67).

III) Patients Suffering from Congestive Heart Failure (CHF) and Patients Suffering from Chronic Obstructive Pulmonary Disease (COPD) (Biomarkers in the Assessment of Congestive Heart Failure Study ("BACH"))

Study Population

This study was approved by the institutional review boards (IRB) of the respective enrolling institutions. A total of 1,641 patients from fifteen centers were enrolled from March, 2007 to February, 2008. These centers included 8 from the United States, 6 from Europe and 1 from New Zealand. To be eligible for the trial patients had to report shortness of breath as the primary complaint upon presentation to the emergency department. Patients under 18 years of age or unable to provide consent were excluded from the trial. Patients determined to be experiencing an acute myocardial infarction were also excluded.

For each patient enrolled in the study, physicians assigned to the emergency department who were blinded to the results of ANP, ADM and other investigational markers, assessed the probability that the patient had acute heart failure or pneumonia via two separate Likert scale questionnaires. The physician assigned a value of 0 to 100 percent clinical certainty.

Confirmation of Diagnosis

To determine the actual diagnosis, two cardiologists reviewed all medical records pertaining to the patient and independently classified the diagnosis as dyspnea due to congestive heart failure, pneumonia or due to other underlying disease. Both cardiologists were blinded to each other, the investigational markers, as well as the emergency physician's preliminary diagnosis. They did have access to the emergency department case report forms that included chest radiographic data, radionuclide angiography, echocardiography, medical history, catheterization data and the hospital course for patients who were admitted to the hospital. In the event of diagnostic disagreement among the cardiology reviewers they were asked to meet to come to a common conclusion. In the event they were unable to come to a common conclusion, a third party cardiology adjudicator was assigned by the endpoints committee and asked to review the data and determine which diagnosis was the most accurate.

In order to come to a conclusion of pneumonia, a pneumonia criterion modified from Fine et al. 1990 and Leroy et al. 1995 had to be fulfilled. Further, all diagnosis of pneumonia had to be verified by an endpoints committee pulmonologist assigned to the case.

Measurement of Markers Used for Two Endpoints

The markers were measured at the assigned core lab at the University of Maryland Medical Center. MR-proANP and MR-proADM were detected using novel fully automated sandwich immunoassay systems on the B.R.A.H.M.S KRYPTOR (B.R.A.H.M.S AG, Hennigsdorf/Berlin, Germany) (Caruhel et al. 2009. *Clin Biochem* 42:725-8). This random access analyzer employs the sensitive Time Resolved Amplified Cryptate Emission (TRACE) technology, based on a non-radioactive-transfer between 2 fluorophores, europium cryptate and XL665. Both automated assays are based essentially on the sandwich chemiluminescence assays which are described in detail elsewhere (Morgenthaler et al. 2004. *Clin Chem* 50:234-6; Morgenthaler et al. 2005 *Clin Chem* 51:1823-9), and which were used in other studies (Khan et al. 2008. *J Am Coll Cardiol* 51:1857-64; Khan et al. 2007. *J Am Coll Cardiol* 49: 1525-32; van Haehling et al. 2009. *J Am Coll Cardiol. in press*; Gegenhuber et al. 2006. *Clin Chem* 52: 827-31,).

For MR-proANP detection, 14 µl of patients' serum were incubated for 14 min. The measuring range was 0-10000 pmol/L, the limit of detection 2.1 pmol/L, and the limit of quantitation 4.5 pmol/L. The intra assay CV was 1.2% and the inter laboratory CV 5.4%. This assay uses the same antibody pair as the reference assay (Morgenthaler et al. 2004. *Clin Chem* 50: 234-6), and the correlation between the two assay systems was r=0.99.

For MR-proADM detection, 26 µl serum was incubated for 29 min. The measuring range was 0-100 nmol/L, the limit of detection and limit of quantification were 0.05 and 0.23 nmol/L, respectively. The intra assay CV was 1.9% and the inter laboratory CV was 9.8%. This assay uses the same antibody pair as described in detail elsewhere (Morgenthaler et al.

2005. *Clin Chem* 51: 1823-9), and the correlation between the two assay systems was r=0.99.

Analysis of Data for all Studies:

Survival rates, i.e. the proportion of patients surviving at a given time after entry into the studies, are plotted in the appended figures over time for different combinations of a particular vasoactive hormone with a particular medication. The patients have been stratified into quintiles according to their respective hormone levels. Data for patients having received the particular medication are plotted separately from patients that did not receive a medication. For some cases, two or more quintiles have been pooled were appropriate. Hazard ratios (HR) have been calculated for various combinations of particular vasoactive hormones with particular medications. HR have also been calculated for particular quintiles and/or pooled quintiles and compared to overall HR for each combination.

Table 1 lists the results for the patients from the BACH study (patients suffering from shortness of breath (SOB), acute coronary syndrome, acute heart failure (AHF), arrhythmia, asthma exacerbation, bronchitis, chest pain, influenza, chronic obstructive pulmonary disease (COPD), pneumonia and/or pulmonary embolism.). At low levels of vasoactive hormones, the administration of e.g. calcium-channel blockers, diuretics and statins has an unfavourable effect, while at higher levels the administration of these drugs has a positive effect. In contrast, at high levels of vasoactive hormones, the administration of e.g. antibiotics has an unfavourable effect, while at lower levels the administration of these drugs has a positive effect.

Table 2 lists the results for the patients from the COSMOS study (patients having suffered from ischemic or haemorrhagic stroke or TIA). At low levels of vasoactive hormones, the administration of statins, anti-coagulants and PLAVIX has an unfavourable effect, while at higher levels the administration of these drugs has a positive effect. In contrast, at high levels of vasoactive hormones, the administration of acetylsalicylic acid, thrombolytic drugs, diuretics and steroids has an unfavourable effect, while at lower levels the administration of these drugs has a positive effect.

Table 3 lists the results for the patients from the LAMP study (patients having suffered a myocardial infarction) in respect to death as the unfavourable effect (outcome). At low levels of vasoactive hormones, the administration of the medication (except for thrombolytic drugs when the hormone is proANP) has an unfavourable effect, while at higher levels the administration of the drugs has a positive effect.

Table 4 lists the results for the patients from the LAMP study (patients having suffered a myocardial infarction) in respect to MACE as the unfavourable effect (outcome). At low levels of vasoactive hormones, the administration of the medication (except for thrombolytic drugs when the hormone is proANP) has an unfavourable effect, while at higher levels the administration of the drugs has a positive effect.

TABLE 1

Results for patients from BACH study

| Medication | Biomarker | HR Medicament (overall patient group) | HR Medicament in Marker-Quintile 1 | Range Biomarker Quintile 1 | HR Medicament in Marker-Quintile 2-4 | Range Biomarker Quintile 2-4 | HR Medicament in Marker-Quintile 5 | Range Biomarker Quintile 5 |
|---|---|---|---|---|---|---|---|---|
| ACE-Inhibitor | MR-proADM | 0.7 | 2.6 | 0.03-0.66 | 0.7 | 0.66-1.89 | 0.6 | 1.89-14.6 |
| Antibiotics | MR-proADM | 2.4 | <0.1 | 0.03-0.52 | 2.3 | 0.52-1.63 | 1.7 | 1.63-12.6 |
| Anti-Coagulant | MR-proADM | 2 | <0.1 | 0.03-0.52 | 1.2 | 0.52-1.63 | 1.4 | 1.63-12.6 |
| Platelet Aggregation Inhibitor | MR-proADM | 0.7 | 1 | 0.25-0.64 | 0.6 | 0.64-1.64 | 0.6 | 1.64-11.2 |
| Beta-Blocker | MR-proADM | 1.2 | <0.1 | 0.25-0.64 | 1 | 0.64-1.64 | 0.9 | 1.64-11.2 |
| Calcium-Channel Blocker | MR-proADM | 0.9 | 1.9 | 0.03-0.66 | 0.9 | 0.66-1.89 | 0.6 | 1.89-14.6 |
| Diuretic | MR-proADM | 1.1 | 2.2 | 0.03-0.66 | 0.5 | 0.66-1.89 | 0.8 | 1.89-14.6 |
| Statin | MR-proADM | 0.7 | 3.1 | 0.03-0.52 | 0.4 | 0.52-1.63 | 0.7 | 1.63-12.6 |
| Steroid | MR-proADM | 1 | <0.1 | 0.03-0.52 | 1.1 | 0.52-1.63 | 1.1 | 1.63-12.6 |
| Warfarin | MR-proADM | 1.6 | <0.1 | 0.03-0.52 | 0.8 | 0.52-1.63 | 1.5 | 1.63-12.6 |
| Antibiotics | MR-proANP | 1.2 | <0.1 | 3.9-54.6 | 0.9 | 54.6-431 | 2.7 | 431-2510 |
| AntiCoagulant | MR-proANP | 1.2 | 0.7 | 15.0-89.7 | 1 | 89.7-512 | 1.3 | 512-2670 |
| Platelet Aggregation Inhibitor | MR-proANP | 1 | <0.1 | 19.9-99.7 | 0.8 | 99.7-478 | 1.5 | 478-2840 |
| Beta-Blocker | MR-proANP | 0.4 | 11.7 | 3.9-54.6 | 0.2 | 54.6-431 | 0.3 | 431-2510 |
| Calcium-Channel Blocker | MR-proANP | 0.6 | 1 | 19.9-99.7 | 1.1 | 99.7-478 | 0.2 | 478-2840 |
| Diuretic | MR-proANP | 1.1 | 0.9 | 15.0-89.7 | 0.7 | 89.7-512 | 0.6 | 512-2670 |
| Statin | MR-proANP | 0.8 | 9.6 | 3.9-54.6 | 0.5 | 54.6-431 | 0.6 | 431-2510 |
| Steroid | MR-proANP | 1 | <0.1 | 3.9-54.6 | 1.4 | 54.6-431 | 1.9 | 431-2510 |
| Warfarin | MR-proANP | 1 | 1.5 | 19.9-99.7 | 0.9 | 99.7-478 | 0.9 | 478-2840 |
| Antibiotics | CT-proAVP | 1.5 | 0.5 | 0.71-5.44 | 1.5 | 5.44-43.2 | 1.6 | 43.2-1050 |
| Anti-Coagulant | CT-proAVP | 2 | <0.1 | 0.45-4.78 | 1.4 | 4.78-41.6 | 1.8 | 41.6-1110 |
| Platelet Aggregation Inhibitor | CT-proAVP | 1.1 | <0.1 | 0.45-4.78 | 1 | 4.78-41.6 | 1.1 | 41.6-1110 |
| Beta-Blocker | CT-proAVP | 0.7 | 1.3 | 1.15-4.87 | 0.9 | 4.87-32.6 | 0.2 | 32.6-484 |
| Calcium-Channel Blocker | CT-proAVP | 0.9 | 1.9 | 0.71-5.44 | 0.9 | 5.44-43.2 | 0.6 | 43.2-1050 |
| Diuretic | CT-proAVP | 1.7 | 2.2 | 0.71-5.44 | 1.5 | 5.44-43.2 | 0.9 | 43.2-1050 |
| Statin | CT-proAVP | 0.6 | 1.6 | 1.15-4.87 | 0.4 | 4.87-32.6 | 0.7 | 32.6-484 |
| Steroid | CT-proAVP | 1 | <0.1 | 0.45-4.78 | 1 | 4.78-41.6 | 1.6 | 41.6-1110 |
| Warfarin | CT-proAVP | 1.6 | <0.1 | 0.45-4.78 | 1.8 | 4.78-41.6 | 1.3 | 41.6-1110 |
| ACE-Inhibitor | BNP | 0.8 | | | 1* | 6-706* | 0.5 | 706-12900 |
| Antibiotics | BNP | 1.2 | <0.1 | 0.5-26.4 | 0.9 | 26.4-748 | 2.3 | 748-1070 |
| Anti-Coagulant | BNP | 1.2 | 1 | 3-65 | 0.8 | 65-904 | 1.7 | 904-7850 |
| Platelet Aggregation Inhibitor | BNP | 1.1 | | | 0.9* | 6-706* | 1.7 | 706-12900 |
| Beta-Blocker | BNP | 1.1 | 15.1 | 0.5-26.4 | 0.6 | 26.4-748 | 0.7 | 748-1070 |
| Calcium-Channel Blocker | BNP | 0.5 | 2.6 | 3-65 | 0.6 | 65-904 | 0.2 | 904-7850 |
| Diuretic | BNP | 1.1 | 1.9 | 3-65 | 0.6 | 65-904 | 0.7 | 904-7850 |
| Statin | BNP | 0.7 | 3 | 0.5-26.4 | 0.5 | 26.4-748 | 0.7 | 748-1070 |
| Steroid | BNP | 1 | <0.1 | 0.5-26.4 | 1.5 | 26.4-748 | 1.5 | 748-1070 |
| Warfarin | BNP | 1.3 | <0.1 | 3-65 | 0.9 | 65-904 | 1.9 | 904-7850 |
| ACE-Inhibitor | CT-ET-1 | 0.7 | >100 | 11.8-54 | 0.5 | 54-157 | 0.4 | 157-752 |

TABLE 1-continued

Results for patients from BACH study

| Medication | Biomarker | HR Medicament (overall patient group) | HR Medicament in Marker-Quintile 1 | Range Biomarker Quintile 1 | HR Medicament in Marker-Quintile 2-4 | Range Biomarker Quintile 2-4 | HR Medicament in Marker-Quintile 5 | Range Biomarker Quintile 5 |
|---|---|---|---|---|---|---|---|---|
| Antibiotics | CT-ET-1 | 0.8 | <0.1 | 11.8-54 | 0.4 | 54-157 | 1.9 | 157-752 |
| Anti-Coagulant | CT-ET-1 | 1.2 | <0.1 | 6.9-67 | 0.8 | 67-182 | 1.9 | 182-709 |
| Platelet Aggregation Inhibitor | CT-ET-1 | 1.1 | 2 | 11.8-54 | 0.7 | 54-157 | 0.9 | 157-752 |
| Beta-Blocker | CT-ET-1 | 0.7 | >100 | 6.9-67 | 0.7 | 67-182 | 0.4 | 182-709 |
| Calcium-Channel Blocker | CT-ET-1 | 0.9 | >100 | 6.9-67 | 0.8 | 67-182 | 0.5 | 182-709 |
| Diuretic | CT-ET-1 | 1.8 | >100 | 11.8-54 | 1 | 54-157 | 0.7 | 157-752 |
| Statin | CT-ET-1 | 0.7 | 2.2 | 11.8-54 | 0.5 | 54-157 | 0.7 | 157-752 |
| Steroid | CT-ET-1 | 1 | <0.1 | 11.8-54 | 1 | 54-157 | 2 | 157-752 |
| Warfarin | CT-ET-1 | 1.3 | <0.1 | 6.9-67 | 0.8 | 67-182 | 1.4 | 182-709 |
| Antibiotics | NT-proBNP | 1.2 | <0.1 | 3-75 | 0.8 | 75-5490 | 1.9 | 5490-120000 |
| Anti-Coagulant | NT-proBNP | 1.2 | 0.2 | 3-280 | 1 | 280-7080 | 1.4 | 7080-112000 |
| Platelet Aggregation Inhibitor | NT-proBNP | 0.9 | 0.5 | 3-280 | 0.5 | 280-7080 | 1.5 | 7080-112000 |
| Beta-Blocker | NT-proBNP | 1.3 | <0.1 | 3-222 | 0.7 | 222-4590 | 1.4 | 4590-147000 |
| Calcium-Channel Blocker | NT-proBNP | 0.6 | 5.8 | 3-280 | 0.6 | 280-7080 | 0.2 | 7080-112000 |
| Diuretic | NT-proBNP | 1.1 | 3.4 | 3-280 | 0.5 | 280-7080 | 0.7 | 7080-112000 |
| Statin | NT-proBNP | 0.7 | 6.8 | 3-75 | 0.5 | 75-5490 | 0.6 | 5490-120000 |
| Steroid | NT-proBNP | 1 | 2.5 | 3-280 | 0.9 | 280-7080 | 1.2 | 7080-112000 |
| Warfarin | NT-proBNP | 0.8 | 2.7 | 3-280 | 0.6 | 280-7080 | 0.7 | 7080-112000 |

MR-proADM values in nmol/L, MR-proANP values in pmol/L, CT-proAVP values in pmol/L, BNP values in pg/mL, CT-proET-1 values in pmol/L, NT-proBNP values in pg/mL
*Quintiles 1 to 4 are pooled

TABLE 2

Results COSMOS

| Medication | Biomarker | HR Medicament (overall patient group) | HR Medicament Marker-Quintile 1 | Range Biomarker Quintile 1 | HR Medicament Marker-Quintile 2-4 | Range Biomarker Quintile 2-4 | HR Medicament Marker-Quintile 5 | Range Biomarker Quintile 5 |
|---|---|---|---|---|---|---|---|---|
| Acetylsalicyclic acid | CT-proAVP | 1.3 | | | 0.8* | 0.69-23.5* | 2.6 | 23.5-499 |
| Diuretic | CT-proAVP | 4 | <0.1 | 0.9-3.9 | 3.1 | 3.9-32.9 | 3 | 32.9-778 |
| Thrombolysis | CT-proAVP | 2 | | | 0.9* | 0.88-18.7* | 2.4 | 18.7-168 |
| Acetylsalicyclic acid | CT-proET-1 | 1.4 | 0.5 | 4.5-55.5 | 1.5 | 55.5-93.1 | 2.5 | 93.1-368 |
| Diuretic | CT-proET-1 | 4.3 | <0.1 | 5.3-55.8 | 5.6 | 55.8-95.9 | 2.6 | 95.9-302 |
| Anti-Coagulant | CT-proET-1 | 1.1 | | | 1.1* | 1-93.1* | 0.7 | 93.1-571 |
| Statin | CT-proET-1 | 1 | 5.2 | 1-51.4 | 1 | 51.4-93.1 | 0.6 | 93.1-571 |
| Steroide | CT-proET-1 | 1.9 | <0.1 | 1-51.4 | 2.9 | 51.4-93.1 | 1.3 | 93.1-571 |
| Thrombolysis | CT-proET-1 | 2 | 0.7 | 1.64-51.5 | 1.3 | 51.5-92.1 | 2.3 | 92.1-253 |
| Acetylsalicyclic acid | MR-proADM | 1 | 0.6 | 0.05-0.47 | 0.7 | 0.47-0.91 | 2.4 | 0.91-5.49 |
| Anti-Coagulant | MR-proADM | 1.2 | >100 | 0.05-0.5 | 1.4 | 0.5-0.94 | 0.7 | 0.94-23.8 |
| Plavix | MR-proADM | 0.3 | 1.8 | 0.05-0.47 | 0.2 | 0.47-0.91 | 0.1 | 0.91-5.49 |
| Statin | MR-proADM | 1 | 4.2 | 0.05-0.47 | 1.6 | 0.47-0.91 | 0.3 | 0.91-5.49 |
| Steroide | MR-proADM | 1.9 | <0.1 | 0.05-0.47 | 0.9 | 0.47-0.91 | 2 | 0.91-5.49 |
| Thrombolysis | MR-proADM | 1.6 | <0.1 | 0.05-0.53 | 1 | 0.53-1.0 | 4 | 1.0-8.1 |
| Acetylsalicyclic acid | MR-proANP | 1.3 | <0.1 | 20.8-71.6 | 1.7 | 71.6-240 | 2.3 | 240-1560 |
| Anti-Coagulant | MR-proANP | 1.2 | >100 | 20-71.2 | 0.6 | 71.2-235 | 0.7 | 235-954 |
| Statin | MR-proANP | 1 | 1 | 20-71.2 | 1.1 | 71.2-235 | 0.7 | 235-954 |
| Thrombolysis | MR-proANP | 1.5 | <0.1 | 22.3-69.5 | <0.1 | 69.5-250 | 1.5 | 250-1540 |

MR-proADM values in nmol/L, MR-proANP values in pmol/L, CT-proAVP values in pmol/L, CT-proET-1 values in pmol/L
*Quintiles 1 to 4 are pooled

TABLE 3

Results LAMP (Outcome Death)

| Medication | Biomarker | HR Medicament (overall patient group) | HR Medicament in Marker-Quantile 1 | Range Biomarker Quintile 1 | HR Medicament in Marker-Quantile 2-4 | Range Biomarker Quintile 2-4 | HR Medicament in Marker-Quantile 5 | Range Biomarker Quintile 5 |
|---|---|---|---|---|---|---|---|---|
| Acetylsalicyclic acid | MR-proADM | 0.3 | >100 | 0.035-0.47 | 0.5 | 0.47-1.18 | 0.3 | 1.18-6.75 |
| Diuretic | MR-proADM | 1.3 | 6.6 | 0.035-0.47 | 1.6 | 0.47-1.18 | 0.4 | 1.18-6.75 |
| ACE-Inhibitor | MR-proANP | 0.2 | >100 | 14.5-59.6 | 0.4 | 59.6-283 | 0.2 | 283-1650 |
| Acetylsalicyclic acid | MR-proANP | 0.3 | >100 | 14.5-59.6 | 0.4 | 59.6-283 | 0.4 | 283-1650 |
| Beta-Blocker | MR-proANP | 0.2 | >100 | 14.5-59.6 | 0.2 | 59.6-283 | 0.4 | 283-1650 |
| Calcium-Channel Blocker | MR-proANP | 1 | 2.8 | 4.94-65 | 1.9 | 65-264 | 0.4 | 264-1630 |
| Diuretic | MR-proANP | 1.4 | 10.1 | 4.94-65 | 1.6 | 65-264 | 0.5 | 264-1630 |

TABLE 3-continued

Results LAMP (Outcome Death)

| Medication | Biomarker | HR Medicament (overall patient group) | HR Medicament in Marker-Quantile 1 | Range Biomarker Quintile 1 | HR Medicament in Marker-Quantile 2-4 | Range Biomarker Quintile 2-4 | HR Medicament in Marker-Quantile 5 | Range Biomarker Quintile 5 |
|---|---|---|---|---|---|---|---|---|
| Nitrate | MR-proANP | 0.5 | >100 | 14.5-59.6 | 0.9 | 59.6-283 | 0.3 | 283-1650 |
| Statin | MR-proANP | 0.1 | >100 | 14.5-59.6 | 0.2 | 59.6-283 | 0.2 | 283-1650 |
| Thrombolytic drug | MR-proANP | 1 | <0.1 | 4.94-65 | 1.2 | 65-264 | 1.9 | 264-1630 |
| Acetylsalicylic acid | CT-proAVP | 0.3 | >100 | 0.31-4.6 | 0.4 | 4.6-42.1 | 0.3 | 42.1-1040 |
| Calcium-Channel Blocker | CT-proAVP | 1 | 1.4 | 0.3-3.6 | 2.1 | 3.6-18.7 | 0.5 | 18.7-441 |
| Diuretic | CT-proAVP | 1.3 | 10.1 | 0.31-4.6 | 1.3 | 4.6-42.1 | 0.7 | 42.1-1040 |
| Nitrate | CT-proAVP | 0.5 | 4.8 | 0.31-4.6 | 0.7 | 4.6-42.1 | 0.3 | 42.1-1040 |
| Statin | CT-proAVP | 0.1 | >100 | 0.31-4.6 | 0.2 | 4.6-42.1 | 0.1 | 42.1-1040 |
| Calcium-Channel Blocker | CT-ET-1 | 1 | 2 | 4.63-56.6 | 1.4 | 56.6-118 | 0.6 | 118-671 |
| Nitrate | CT-ET-1 | 0.6 | 1 | 3.7-65.4 | 1 | 65.4-136 | 0.3 | 136-468 |
| Acetylsalicylic acid | NT-proBNP | 0.3 | >100 | 0.12-184 | 0.3 | 184-2700 | 0.5 | 2700-34100 |
| Calcium-Channel Blocker | NT-proBNP | 0.6 | 3 | 0.3-204 | 0.8 | 204-3160 | 0.3 | 3160-11800 |
| Diuretic | NT-proBNP | 1.3 | 2.6 | 0.3-204 | 1.9 | 204-3160 | 0.4 | 3160-11800 |
| Nicorandil | NT-proBNP | 0.5 | 4.8 | 0.3-204 | <0.1 | 204-3160 | 0.5 | 3160-11800 |
| Nitrate | NT-proBNP | 0.7 | 1.9 | 0.12-184 | 0.6 | 184-2700 | 0.5 | 2700-34100 |
| Thrombolytic drug | NT-proBNP | 1 | 2.2 | 0.12-184 | 0.9 | 184-2700 | 0.9 | 2700-34100 |

MR-proADM values in nmol/L, MR-proANP values in pmol/L, CT-proAVP values in pmol/L, CT-proET-1 values in pmol/L, NT-proBNP values in pg/mL

TABLE 4

Results LAMP (Outcome MACE)

| Medication | Biomarker | HR Medicament (overall patient group) | HR Medicament in Marker-Quantile 1 | Range Biomarker Quintile 1 | HR Medicament in Marker-Quantile 2-4 | Range Biomarker Quintile 2-4 | HR Medicament in Marker-Quantile 5 | Range Biomarker Quintile 5 |
|---|---|---|---|---|---|---|---|---|
| ACE Inhibitor | MR-proADM | 0.6 | 2.3 | 0.09-0.53 | 0.9 | 0.53-1.16 | 0.4 | 1.16-6.95 |
| Calcium-Channel Blocker | MR-proADM | 0.9 | 1.8 | 0.04-0.47 | 1.1 | 0.47-1.18 | 0.5 | 1.18-6.75 |
| Diuretic | MR-proADM | 1.8 | 4.8 | 0.04-0.47 | 2 | 0.47-1.18 | 0.6 | 1.18-6.75 |
| Nitrate | MR-proADM | 1.1 | 2.4 | 0.09-0.53 | 0.9 | 0.53-1.16 | 1 | 1.16-6.95 |
| ACE Inhibitor | MR-proANP | 0.6 | 2.4 | 4.9-65 | 0.7 | 65-264 | 0.5 | 264-1630 |
| Calcium-Channel Blocker | MR-proANP | 0.9 | 3 | 14.5-59.6 | 1.2 | 59.6-283 | 0.4 | 283-1650 |
| Diuretic | MR-proANP | 1.9 | 7.4 | 14.5-59.6 | 1.5 | 59.6-283 | 0.7 | 283-1650 |
| Nitrate | MR-proANP | 1.1 | 3.8 | 4.9-65 | 1 | 65-264 | 0.8 | 264-1630 |
| Thrombolytic drug | MR-proANP | 1 | 0.5 | 4.9-65 | 1.3 | 65-264 | 1.5 | 264-1630 |
| ACE Inhibitor | CT-proAVP | 0.6 | 2.3 | 0.3-3.6 | 0.9 | 3.6-18.7 | 0.4 | 18.7-441 |
| Calcium-Channel Blocker | CT-proAVP | 0.9 | 2.4 | 0.31-4.6 | 1.3 | 4.6-42.1 | 0.4 | 42.1-1040 |
| Nitrate | CT-proAVP | 1.1 | 2.8 | 0.3-3.6 | 1.2 | 3.6-18.7 | 0.6 | 18.7-441 |
| ACE Inhibitor | CT-proET-1 | 0.4 | >100 | 3.7-65.4 | 0.7 | 65.4-136 | 0.2 | 136-468 |
| Beta-Blocker | CT-proET-1 | 0.3 | >100 | 3.7-65.4 | 0.5 | 65.4-136 | 0.3 | 136-468 |
| Calcium-Channel Blocker | CT-proET-1 | 1.1 | 5.6 | 4.6-56.6 | 1 | 56.6-118 | 0.7 | 118-671 |
| Diuretic | CT-proET-1 | 1.3 | 2 | 3.7-65.4 | 1.8 | 65.4-136 | 0.4 | 136-468 |
| Nicorandil | CT-proET-1 | 1.2 | 7.1 | 4.6-56.6 | 1.2 | 56.6-118 | 0.7 | 118-671 |
| Nitrate | CT-proET-1 | 1.1 | 2.4 | 4.6-56.6 | 0.9 | 56.6-118 | 0.9 | 118-671 |
| Statin | CT-proET-1 | 0.2 | >100 | 3.7-65.4 | 0.3 | 65.4-136 | 0.2 | 136-468 |
| ACE Inhibitor | NT-proBNP | 0.6 | 1.8 | 0.12-184 | 0.8 | 184-2700 | 0.4 | 2700-34100 |
| Beta-Blocker | NT-proBNP | 0.4 | 2.3 | 0.3-204 | 0.6 | 204-3160 | 0.5 | 3160-11800 |
| Calcium-Channel Blocker | NT-proBNP | 0.9 | 1.4 | 0.3-204 | 1 | 204-3160 | 0.7 | 3160-11800 |
| Nitrate | NT-proBNP | 1 | 2.4 | 0.12-184 | 0.8 | 184-2700 | 0.9 | 2700-34100 |
| Statin | NT-proBNP | 0.5 | 1.3 | 0.12-184 | 0.5 | 184-2700 | 0.6 | 2700-34100 |
| Thrombolytic drug | NT-proBNP | 1 | 1.8 | 0.12-184 | 0.9 | 184-2700 | 0.9 | 2700-34100 |

MR-proADM values in nmol/L, MR-proANP values in pmol/L, CT-proAVP values in pmol/L, CT-proET-1 values in pmol/L, NT-proBNP values in pg/mL

The invention claimed is:
1. A method for the stratification of a subject having an acute or a chronic disease for response to or risk of unfavorable effect from administration of a medication, wherein said disease affects endothelial function, comprising:
  (i) detecting and quantitating in a sample of bodily fluid from said subject the concentration of a vasoactive hormone, a precursor of said vasoactive hormone, or a fragment of said hormone or precursor, selected from the group consisting of
    a. a peptide hormone a precursor of said peptide hormone, and a fragment of said peptide hormone or precursor of said peptide hormone, selected from the group consisting of Adrenomedullin (ADM), proADM, Midregional proADM (MR-proADM), Atrial Natriuretic Peptide (ANP), proANP, Midregional proANP (MR-proANP), Brain natriuretic peptide (BNP), proBNP, N-Terminal proBNP (NT-proBNP), C-type natriuretic peptide (CNP), proCNP, Endothelin-1 (ET-1), proET-1, C-Terminal proET-1 (CT-proET-1), Endothelin-2 (ET-2), proET-2, Endothelin-3 (ET-3), proET-3, Arginine-Vasopressin (AVP), proAVP, C-Terminal-proAVP (CT-proAVP or Copeptin), Dendroaspis natriuretic peptide (DNP), proDNP, Urodilatin, proUrodilatin, Angiotensin II, pro-Angiotensin-II, Urocortin, proUrocortin, Urocortin-2 (Stresscopin-related peptide), proUrocortin-2, Urocortin-3 (Stresscopin), proUrocortin-3, Urotensin-II, proUrotensin-II, Urotensin II-related protein (URP), proURP, Neuropeptide Y (NPY), proNPY, Vasoactive intestinal peptide (VIP), proVIP, Calcitonin gene-related peptide I (CGRP I), proCGRP I, Calcitonin gene-related peptide II (CGRP II), proCGRP II, Relaxin, proRelaxin, Endokinin A, and proEndokinin A;
    b. a small peptide hormone selected from the group consisting of Bradykinin, proBradykinin, Apelin, proApelin, Neurotensin, proNeurotensin, Substance P, Neurokinin A (Substance K), proTachykinin A, N-terminal proTachykinin A (NT-proPTA), Endokinin A/B, proEndokinin A/B, Endokinin C, proEndokinin C, Methionine-Enkephalin, Leucine-Enkephalin, proenkephalin (PENK), and Mid-Regional-PENK (MR-PENK); or
    c. a hormone selected from the group consisting of Serotonin, Prostaglandins and Thromboxane;
    wherein said detection and quantitation comprises a diagnostic assay, said assay comprising
    a'. contacting the sample with a diagnostic assay reagent comprising a capture probe that specifically binds to vasoactive hormone, precursor of said vasoactive hormone or fragment of said hormone or precursor, and
    b'. detecting and quantitating thus-formed complexes of capture probe and vasoactive hormone, precursor of said vasoactive hormone or fragment of said hormone or precursor, and;
  (ii) stratifying said subject based on the thus-determined concentration of the vasoactive hormone, precursor of said vasoactive hormone or fragment of said hormone or precursor into one of the following categories by comparison to pre-determined threshold concentration values correlated to the categories:
    (a) a responder to a medication for treatment of said disease;
    (b) a non-responder to a medication for treatment of said disease not showing an unfavorable effect after having received said medication;
    (c) a subject showing an unfavorable effect after having received said medication,
      wherein the vasoactive hormone is ADM, pro-ADM or MR-proADM,
      wherein the disease is selected from the group consisting of chronic obstructive pulmonary disease (COPD), post stroke condition and post myocardial infarct condition, and
      wherein the medication is selected from the group consisting of an anti-coagulant, warfarin, a thrombolytic drug, a platelet aggregation inhibitor, a β-blocker, a lipid lowering substance, a statin, a diuretic, an Angiotensin-Converting Enzyme (ACE) inhibitor, a calcium channel blocker, a prostacyclin derivative, a hormone therapeutic agent, a steroid, a nitrate, acetylsalicylic acid and an antibiotic;
    (d) a subject showing an unfavorable effect after having received said medication,
      wherein the vasoactive hormone is ANP, pro-ANP, or MR-proANP),
      wherein the disease is selected from the group consisting of COPD, post stroke condition and post myocardial infarct condition, and
      wherein the medication is selected from the group consisting of an anti-coagulant, warfarin, a thrombolytic drug, a platelet aggregation inhibitor, a β-blocker, a lipid lowering substance, a statin, a diuretic, an ACE inhibitor, a calcium channel blocker, a prostacyclin derivative, a hormone therapeutic agent, a steroid, a nitrate, acetylsalicylic acid and antibiotic;
    (e) a subject showing an unfavorable effect after having received said medication,
      wherein the vasoactive hormone is Endothelin-1, proET-1 or CT-proET-1,
      wherein the disease is selected from the group consisting of COPD, post stroke condition and post myocardial infarct condition, and
      wherein the medication is selected from the group consisting of an anti-coagulant, warfarin, a thrombolytic drug, a platelet aggregation inhibitor, a β-blocker, an anti-oxidant, a lipid lowering substance, a statin, a diuretic, an ACE inhibitor, a calcium channel blocker, an endothelin-receptor antagonist, a prostacyclin derivative, a hormone therapeutic agent, a steroid, a nitrate, acetylsalicylic acid, and an antibiotic; or
    (f) a subject showing an unfavorable effect after having received said medication,
      wherein the vasoactive hormone is AVP, proAVP, or CT-proAVP (Copeptin),
      wherein the disease is selected from the group consisting of COPD, post stroke condition and post myocardial infarct condition, and
      wherein the medication is selected from the group consisting of an anti-coagulant, warfarin, a thrombolytic drug, a platelet aggregation inhibitor, a β-blocker, an anti-oxidant, a lipid lowering substance, a statin, a diuretic, an ACE inhibitor, a calcium channel blocker, a prostacyclin derivative, a hormone therapeutic agent, a steroid, a nitrate, acetylsalicylic acid and an antibiotic.

2. The method of claim 1, wherein categories (a) and (b) are considered as a single category.

3. A method for the stratification of a subject having an acute or a chronic disease for risk of an unfavourable effect from administration of a medication, wherein said disease affects endothelial function, comprising:
  (i) detecting and quantitating in a sample of bodily fluid from said subject the concentration of a vasoactive hormone, a precursor of said vasoactive hormone, or a fragment of said hormone or precursor, selected from the group consisting of
    a. a peptide hormone a precursor of said peptide hormone, and a fragment of said peptide hormone or precursor of said peptide hormone, selected from the group consisting of Adrenomedullin (ADM), proADM, Midregional pro-ADM (MR-proADM), Atrial Natriuretic Peptide (ANP), proANP, Midregional proANP (MR-proANP), Brain natriuretic peptide (BNP), proBNP, N-Terminal proBNP (NT-proBNP), C-type natriuretic peptide (CNP), proCNP, Endothelin-1 (ET-1), proET-1, C-Terminal proET-1 (CT-proET-1), Endothelin-2 (ET-2), proET-2, Endothelin-3 (ET-3), proET-3, Arginine-Vasopressin (AVP), proAVP, C-Terminal-proAVP (CT-proAVP or Copeptin), Dendroaspis natriuretic peptide (DNP), proDNP, Urodilatin, proUrodilatin, Angiotensin II, pro-Angiotensin-II, Urocortin, proUrocortin, Urocortin-2 (Stresscopin-related peptide), proUrocortin-2, Urocortin-3 (Stresscopin), proUrocortin-3, Urotensin-II, proUrotensin-II, Urotensin II-related protein (URP), proURP, Neuropeptide Y (NPY), proNPY, Vasoactive intestinal peptide (VIP), proVIP, Calcitonin gene-related peptide I (CGRP I), proCGRP I, Calcitonin gene-related peptide II (CGRP II), proCGRP II, Relaxin, proRelaxin, Endokinin A, and proEndokinin A;
    b. a small peptide hormone selected from the group consisting of Bradykinin, proBradykinin, Apelin, proApelin, Neurotensin, proNeurotensin, Substance P, Neurokinin A (Substance K), proTachykinin A, N-terminal proTachykinin A (NT-proPTA), Endokinin A/B, proEndokinin A/B, Endokinin C, proEndokinin C, Methionine-Enkephalin, Leucine-Enkephalin, proenkephalin (PENK), and Mid-Regional-PENK (MR-PENK); or
    c. a hormone selected from the group consisting of Serotonin, Prostaglandins and Thromboxane;
    wherein said detection and quantitation comprises a diagnostic assay, said assay comprising
    a'. contacting the sample with a diagnostic assay reagent comprising a capture probe that specifically binds to vasoactive hormone, precursor of said vasoactive hormone or fragment of said hormone or precursor, and
    b'. detecting and quantitating thus-formed complexes of capture probe and vasoactive hormone, precursor of said vasoactive hormone or fragment of said hormone or precursor, and;
  (ii) attributing a risk of an unfavorable effect of said medication to the concentration of the vasoactive hormone, precursor of said vasoactive hormone or fragment of said hormone or precursor, by comparison with a predetermined threshold concentration value correlated to said risk in the sample.

4. The method of claim 1, for avoiding an unfavorable effect after receiving a particular medication.

5. The method of claim 1, wherein the precursor fragment of the vasoactive hormone adrenomedullin is MR-proADM.

6. The method of claim 1, wherein the precursor fragment of the vasoactive hormone ANP is MR-proANP.

7. The method of claim 1, wherein the precursor fragment of the vasoactive hormone endothelin-1 is CT-proET 1.

8. The method of claim 1, wherein the precursor fragment of the vasoactive hormone Arg-Vasopressin is C-terminal pro-AVP (Copeptin).

9. The method of claim 1, wherein the medication is selected from the group consisting of an anti-coagulant, a thrombolytic drug, a platelet aggregation inhibitor, a β-blocker, an anti-oxidant, a lipid lowering substance, a diuretic, an ACE inhibitor, a calcium channel blocker, an endothelin-receptor antagonist, a phoshodiesterase type 5 inhibitor, a prostacyclin derivative, a soluble guanylate cyclase activator, a hormone therapeutic agent, a nitrate, an adenosine receptor blocker, a cardiac glycoside, an angiotensin-II antagonist, an anti-diabetic drug, an antiarrhythmic and an antibiotic.

10. The method of claim 9, wherein the medication is selected from the group consisting of ACE inhibitors, diuretics and β-blockers.

11. The method of claim 1, wherein the unfavourable effect is death or major adverse cardiac event (MACE).

12. The method of claim 1, wherein the bodily fluid is selected from the group of blood, serum, plasma, cerebrospinal fluid, urine, saliva, sputum, and pleural effusions.

13. The method of claim 1, wherein the diagnostic assay is an immunoassay.

14. The method of claim 1, wherein the capture molecule is an antibody or a functional fragment thereof that specifically binds to said vasoactive hormone, precursor of said vasoactive hormone or fragment of said hormone or precursor.

15. The method of claim 1, wherein the subject is stratified into a category by comparing the concentration of said vasoactive hormone, precursor of said vasoactive hormone or fragment of said hormone or precursor in the subject, to the concentration of said vasoactive hormone, precursor of said vasoactive hormone or fragment of said hormone or precursor in a reference population of patients, and
  wherein the threshold value for each category is predetermined by correlation of the concentration of said vasoactive hormone, precursor of said vasoactive hormone or fragment of said hormone or precursor in said reference population of patients who are treated with said medication and a reference population of patients who are not treated with said medication, and a threshold for each category of response to or unfavorable effect of the medication is thereby predetermined.

16. The method of claim 15, wherein the threshold value is determined with respect to a hazard ratio determined by comparison of the hazard ratio between the reference population of patients who were treated with said medication with each other and with the hazard ratio of the overall population of reference patients.

17. The method of claim 1, wherein
  if the patient is categorized as a responder to the medication, benefit of the treatment is indicated;
  if the patient is categorized as a non-responder to a medication for treatment of said disease not showing an unfavorable effect after having received said medication, neither risk nor benefit of the treatment is indicated; and
  if the patient is categorized as a subject showing an unfavorable effect after having received said medication, risk of adverse outcome caused by the treatment is indicated.

* * * * *

SEQUENCE LISTING

<160> NUMBER OF SEQ ID NOS: 24

<210> SEQ ID NO 1
<211> LENGTH: 185
<212> TYPE: PRT
<213> ORGANISM: Homo sapiens

<400> SEQUENCE: 1

Met Lys Leu Val Ser Val Ala Leu Met Tyr Leu Gly Ser Leu Ala Phe
1               5                   10                  15

-continued

```
Leu Gly Ala Asp Thr Ala Arg Leu Asp Val Ala Ser Glu Phe Arg Lys
            20                  25                  30
Lys Trp Asn Lys Trp Ala Leu Ser Arg Gly Lys Arg Glu Leu Arg Met
        35                  40                  45
Ser Ser Ser Tyr Pro Thr Gly Leu Ala Asp Val Lys Ala Gly Pro Ala
50                  55                  60
Gln Thr Leu Ile Arg Pro Gln Asp Met Lys Gly Ala Ser Arg Ser Pro
65                  70                  75                  80
Glu Asp Ser Ser Pro Asp Ala Ala Arg Ile Arg Val Lys Arg Tyr Arg
                85                  90                  95
Gln Ser Met Asn Asn Phe Gln Gly Leu Arg Ser Phe Gly Cys Arg Phe
            100                 105                 110
Gly Thr Cys Thr Val Gln Lys Leu Ala His Gln Ile Tyr Gln Phe Thr
        115                 120                 125
Asp Lys Asp Lys Asp Asn Val Ala Pro Arg Ser Lys Ile Ser Pro Gln
130                 135                 140
Gly Tyr Gly Arg Arg Arg Arg Ser Leu Pro Glu Ala Gly Pro Gly Pro
145                 150                 155                 160
Arg Thr Leu Val Ser Ser Lys Pro Gln Ala His Gly Ala Pro Ala Pro
                165                 170                 175
Pro Ser Gly Ser Ala Pro His Phe Leu
            180                 185

<210> SEQ ID NO 2
<211> LENGTH: 164
<212> TYPE: PRT
<213> ORGANISM: Homo sapiens

<400> SEQUENCE: 2

Ala Arg Leu Asp Val Ala Ser Glu Phe Arg Lys Lys Trp Asn Lys Trp
1               5                   10                  15
Ala Leu Ser Arg Gly Lys Arg Glu Leu Arg Met Ser Ser Ser Tyr Pro
            20                  25                  30
Thr Gly Leu Ala Asp Val Lys Ala Gly Pro Ala Gln Thr Leu Ile Arg
        35                  40                  45
Pro Gln Asp Met Lys Gly Ala Ser Arg Ser Pro Glu Asp Ser Ser Pro
50                  55                  60
Asp Ala Ala Arg Ile Arg Val Lys Arg Tyr Arg Gln Ser Met Asn Asn
65                  70                  75                  80
Phe Gln Gly Leu Arg Ser Phe Gly Cys Arg Phe Gly Thr Cys Thr Val
                85                  90                  95
Gln Lys Leu Ala His Gln Ile Tyr Gln Phe Thr Asp Lys Asp Lys Asp
            100                 105                 110
Asn Val Ala Pro Arg Ser Lys Ile Ser Pro Gln Gly Tyr Gly Arg Arg
        115                 120                 125
Arg Arg Arg Ser Leu Pro Glu Ala Gly Pro Gly Arg Thr Leu Val Ser
    130                 135                 140
Ser Lys Pro Gln Ala His Gly Ala Pro Ala Pro Pro Ser Gly Ser Ala
145                 150                 155                 160
Pro His Phe Leu

<210> SEQ ID NO 3
<211> LENGTH: 20
<212> TYPE: PRT
<213> ORGANISM: Homo sapiens
```

```
<400> SEQUENCE: 3

Ala Arg Leu Asp Val Ala Ser Glu Phe Arg Lys Lys Trp Asn Lys Trp
1               5                   10                  15

Ala Leu Ser Arg
            20

<210> SEQ ID NO 4
<211> LENGTH: 40
<212> TYPE: PRT
<213> ORGANISM: Homo sapiens

<400> SEQUENCE: 4

Glu Leu Arg Met Ser Ser Ser Tyr Pro Thr Gly Leu Ala Asp Val Lys
1               5                   10                  15

Ala Gly Pro Ala Gln Thr Leu Ile Arg Pro Gln Asp Met Lys Gly Ala
            20                  25                  30

Ser Arg Ser Pro Glu Asp Ser Ser
            35                  40

<210> SEQ ID NO 5
<211> LENGTH: 52
<212> TYPE: PRT
<213> ORGANISM: Homo sapiens

<400> SEQUENCE: 5

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
            35                  40                  45

Pro Gln Gly Tyr
            50

<210> SEQ ID NO 6
<211> LENGTH: 153
<212> TYPE: PRT
<213> ORGANISM: Homo sapiens

<400> SEQUENCE: 6

Met Ser Ser Phe Ser Thr Thr Thr Val Ser Phe Leu Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
            35                  40                  45

Glu Lys Met Pro Leu Glu Asp Glu Val Val Pro Pro Gln Val Leu Ser
    50                  55                  60

Glu Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
            115                 120                 125

Ser Cys Phe Gly Gly Arg Met Asp Arg Ile Gly Ala Gln Ser Gly Leu
            130                 135                 140
```

```
Gly Cys Asn Ser Phe Arg Tyr Arg Arg
145                 150
```

<210> SEQ ID NO 7
<211> LENGTH: 126
<212> TYPE: PRT
<213> ORGANISM: Homo sapiens

<400> SEQUENCE: 7

```
Asn Pro Met Tyr Asn Ala Val Ser Asn Ala Asp Leu Met Asp Phe Lys
1               5                   10                  15

Asn Leu Leu Asp His Leu Glu Glu Lys Met Pro Leu Glu Asp Glu Val
            20                  25                  30

Val Pro Pro Gln Val Leu Ser Glu Pro Asn Glu Glu Ala Gly Ala Ala
        35                  40                  45

Leu Ser Pro Leu Pro Glu Val Pro Pro Trp Thr Gly Glu Val Ser Pro
    50                  55                  60

Ala Gln Arg Asp Gly Gly Ala Leu Gly Arg Gly Pro Trp Asp Ser Ser
65                  70                  75                  80

Asp Arg Ser Ala Leu Leu Lys Ser Lys Leu Arg Ala Leu Leu Thr Ala
                85                  90                  95

Pro Arg Ser Leu Arg Arg Ser Ser Cys Phe Gly Gly Arg Met Asp Arg
            100                 105                 110

Ile Gly Ala Gln Ser Gly Leu Gly Cys Asn Ser Phe Arg Tyr
        115                 120                 125
```

<210> SEQ ID NO 8
<211> LENGTH: 28
<212> TYPE: PRT
<213> ORGANISM: Homo sapiens

<400> SEQUENCE: 8

```
Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25
```

<210> SEQ ID NO 9
<211> LENGTH: 98
<212> TYPE: PRT
<213> ORGANISM: Homo sapiens

<400> SEQUENCE: 9

```
Asn Pro Met Tyr Asn Ala Val Ser Asn Ala Asp Leu Met Asp Phe Lys
1               5                   10                  15

Asn Leu Leu Asp His Leu Glu Glu Lys Met Pro Leu Glu Asp Glu Val
            20                  25                  30

Val Pro Pro Gln Val Leu Ser Glu Pro Asn Glu Glu Ala Gly Ala Ala
        35                  40                  45

Leu Ser Pro Leu Pro Glu Val Pro Pro Trp Thr Gly Glu Val Ser Pro
    50                  55                  60

Ala Gln Arg Asp Gly Gly Ala Leu Gly Arg Gly Pro Trp Asp Ser Ser
65                  70                  75                  80

Asp Arg Ser Ala Leu Leu Lys Ser Lys Leu Arg Ala Leu Leu Thr Ala
                85                  90                  95

Pro Arg
```

-continued

```
<210> SEQ ID NO 10
<211> LENGTH: 38
<212> TYPE: PRT
<213> ORGANISM: Homo sapiens

<400> SEQUENCE: 10

Pro Glu Val Pro Pro Trp Thr Gly Glu Val Ser Pro Ala Gln Arg Asp
1               5                   10                  15

Gly Gly Ala Leu Gly Arg Gly Pro Trp Asp Ser Ser Asp Arg Ser Ala
            20                  25                  30

Leu Leu Lys Ser Lys Leu
            35

<210> SEQ ID NO 11
<211> LENGTH: 164
<212> TYPE: PRT
<213> ORGANISM: Homo sapiens

<400> SEQUENCE: 11

Met Pro Asp Thr Met Leu Pro Ala Cys Phe Leu Gly Leu Leu Ala Phe
1               5                   10                  15

Ser Ser Ala Cys Tyr Phe Gln Asn Cys Pro Arg Gly Gly Lys Arg Ala
            20                  25                  30

Met Ser Asp Leu Glu Leu Arg Gln Cys Leu Pro Cys Gly Pro Gly Gly
            35                  40                  45

Lys Gly Arg Cys Phe Gly Pro Ser Ile Cys Cys Ala Asp Glu Leu Gly
    50                  55                  60

Cys Phe Val Gly Thr Ala Glu Ala Leu Arg Cys Gln Glu Glu Asn Tyr
65                  70                  75                  80

Leu Pro Ser Pro Cys Gln Ser Gly Gln Lys Ala Cys Gly Ser Gly Gly
                85                  90                  95

Arg Cys Ala Ala Phe Gly Val Cys Cys Asn Asp Glu Ser Cys Val Thr
            100                 105                 110

Glu Pro Glu Cys Arg Glu Gly Phe His Arg Arg Ala Arg Ala Ser Asp
            115                 120                 125

Arg Ser Asn Ala Thr Gln Leu Asp Gly Pro Ala Gly Ala Leu Leu Leu
    130                 135                 140

Arg Leu Val Gln Leu Ala Gly Ala Pro Glu Pro Phe Glu Pro Ala Gln
145                 150                 155                 160

Pro Asp Ala Tyr

<210> SEQ ID NO 12
<211> LENGTH: 145
<212> TYPE: PRT
<213> ORGANISM: Homo sapiens

<400> SEQUENCE: 12

Cys Tyr Phe Gln Asn Cys Pro Arg Gly Gly Lys Arg Ala Met Ser Asp
1               5                   10                  15

Leu Glu Leu Arg Gln Cys Leu Pro Cys Gly Pro Gly Gly Lys Gly Arg
            20                  25                  30

Cys Phe Gly Pro Ser Ile Cys Cys Ala Asp Glu Leu Gly Cys Phe Val
            35                  40                  45

Gly Thr Ala Glu Ala Leu Arg Cys Gln Glu Glu Asn Tyr Leu Pro Ser
    50                  55                  60

Pro Cys Gln Ser Gly Gln Lys Ala Cys Gly Ser Gly Gly Arg Cys Ala
65                  70                  75                  80
```

-continued

```
Ala Phe Gly Val Cys Cys Asn Asp Glu Ser Cys Val Thr Glu Pro Glu
                85                  90                  95

Cys Arg Glu Gly Phe His Arg Arg Ala Arg Ala Ser Asp Arg Ser Asn
            100                 105                 110

Ala Thr Gln Leu Asp Gly Pro Ala Gly Ala Leu Leu Leu Arg Leu Val
        115                 120                 125

Gln Leu Ala Gly Ala Pro Glu Pro Phe Glu Pro Ala Gln Pro Asp Ala
    130                 135                 140

Tyr
145

<210> SEQ ID NO 13
<211> LENGTH: 9
<212> TYPE: PRT
<213> ORGANISM: Homo sapiens

<400> SEQUENCE: 13

Cys Tyr Phe Gln Asn Cys Pro Arg Gly
1               5

<210> SEQ ID NO 14
<211> LENGTH: 39
<212> TYPE: PRT
<213> ORGANISM: Homo sapiens

<400> SEQUENCE: 14

Ala Ser Asp Arg Ser Asn Ala Thr Gln Leu Asp Gly Pro Ala Gly Ala
1               5                   10                  15

Leu Leu Leu Arg Leu Val Gln Leu Ala Gly Ala Pro Glu Pro Phe Glu
                20                  25                  30

Pro Ala Gln Pro Asp Ala Tyr
        35

<210> SEQ ID NO 15
<211> LENGTH: 93
<212> TYPE: PRT
<213> ORGANISM: Homo sapiens

<400> SEQUENCE: 15

Ala Met Ser Asp Leu Glu Leu Arg Gln Cys Leu Pro Cys Gly Pro Gly
1               5                   10                  15

Gly Lys Gly Arg Cys Phe Gly Pro Ser Ile Cys Cys Ala Asp Glu Leu
                20                  25                  30

Gly Cys Phe Val Gly Thr Ala Glu Ala Leu Arg Cys Gln Glu Glu Asn
            35                  40                  45

Tyr Leu Pro Ser Pro Cys Gln Ser Gly Gln Lys Ala Cys Gly Ser Gly
        50                  55                  60

Gly Arg Cys Ala Ala Phe Gly Val Cys Cys Asn Asp Glu Ser Cys Val
65                  70                  75                  80

Thr Glu Pro Glu Cys Arg Glu Gly Phe His Arg Arg Ala
                85                  90

<210> SEQ ID NO 16
<211> LENGTH: 212
<212> TYPE: PRT
<213> ORGANISM: Homo sapiens

<400> SEQUENCE: 16

Met Asp Tyr Leu Leu Met Ile Phe Ser Leu Leu Phe Val Ala Cys Gln
1               5                   10                  15
```

Gly Ala Pro Glu Thr Ala Val Leu Gly Ala Glu Leu Ser Ala Val Gly
            20                  25                  30

Glu Asn Gly Gly Glu Lys Pro Thr Pro Ser Pro Pro Trp Arg Leu Arg
            35                  40                  45

Arg Ser Lys Arg Cys Ser Cys Ser Ser Leu Met Asp Lys Glu Cys Val
 50                  55                  60

Tyr Phe Cys His Leu Asp Ile Ile Trp Val Asn Thr Pro Glu His Val
 65                  70                  75                  80

Val Pro Tyr Gly Leu Gly Ser Pro Arg Ser Lys Arg Ala Leu Glu Asn
            85                  90                  95

Leu Leu Pro Thr Lys Ala Thr Asp Arg Glu Asn Arg Cys Gln Cys Ala
            100                 105                 110

Ser Gln Lys Asp Lys Lys Cys Trp Asn Phe Cys Gln Ala Gly Lys Glu
            115                 120                 125

Leu Arg Ala Glu Asp Ile Met Glu Lys Asp Trp Asn Asn His Lys Lys
 130                 135                 140

Gly Lys Asp Cys Ser Lys Leu Gly Lys Lys Cys Ile Tyr Gln Gln Leu
145                 150                 155                 160

Val Arg Gly Arg Lys Ile Arg Arg Ser Ser Glu Glu His Leu Arg Gln
            165                 170                 175

Thr Arg Ser Glu Thr Met Arg Asn Ser Val Lys Ser Ser Phe His Asp
            180                 185                 190

Pro Lys Leu Lys Gly Lys Pro Ser Arg Glu Arg Tyr Val Thr His Asn
            195                 200                 205

Arg Ala His Trp
            210

<210> SEQ ID NO 17
<211> LENGTH: 195
<212> TYPE: PRT
<213> ORGANISM: Homo sapiens

<400> SEQUENCE: 17

Ala Pro Glu Thr Ala Val Leu Gly Ala Glu Leu Ser Ala Val Gly Glu
 1               5                  10                  15

Asn Gly Gly Glu Lys Pro Thr Pro Ser Pro Pro Trp Arg Leu Arg Arg
            20                  25                  30

Ser Lys Arg Cys Ser Cys Ser Ser Leu Met Asp Lys Glu Cys Val Tyr
            35                  40                  45

Phe Cys His Leu Asp Ile Ile Trp Val Asn Thr Pro Glu His Val Val
 50                  55                  60

Pro Tyr Gly Leu Gly Ser Pro Arg Ser Lys Arg Ala Leu Glu Asn Leu
 65                  70                  75                  80

Leu Pro Thr Lys Ala Thr Asp Arg Glu Asn Arg Cys Gln Cys Ala Ser
            85                  90                  95

Gln Lys Asp Lys Lys Cys Trp Asn Phe Cys Gln Ala Gly Lys Glu Leu
            100                 105                 110

Arg Ala Glu Asp Ile Met Glu Lys Asp Trp Asn Asn His Lys Lys Gly
            115                 120                 125

Lys Asp Cys Ser Lys Leu Gly Lys Lys Cys Ile Tyr Gln Gln Leu Val
            130                 135                 140

Arg Gly Arg Lys Ile Arg Arg Ser Ser Glu Glu His Leu Arg Gln Thr
145                 150                 155                 160

Arg Ser Glu Thr Met Arg Asn Ser Val Lys Ser Ser Phe His Asp Pro

```
                    165                 170                 175
Lys Leu Lys Gly Lys Pro Ser Arg Glu Arg Tyr Val Thr His Asn Arg
            180                 185                 190

Ala His Trp
        195

<210> SEQ ID NO 18
<211> LENGTH: 21
<212> TYPE: PRT
<213> ORGANISM: Homo sapiens

<400> SEQUENCE: 18

Cys Ser Cys Ser Ser Leu Met Asp Lys Glu Cys Val Tyr Phe Cys His
1               5                   10                  15

Leu Asp Ile Ile Trp
            20

<210> SEQ ID NO 19
<211> LENGTH: 45
<212> TYPE: PRT
<213> ORGANISM: Homo sapiens

<400> SEQUENCE: 19

Arg Ser Ser Glu Glu His Leu Arg Gln Thr Arg Ser Glu Thr Met Arg
1               5                   10                  15

Asn Ser Val Lys Ser Ser Phe His Asp Pro Lys Leu Lys Gly Lys Pro
            20                  25                  30

Ser Arg Glu Arg Tyr Val Thr His Asn Arg Ala His Trp
        35                  40                  45

<210> SEQ ID NO 20
<211> LENGTH: 38
<212> TYPE: PRT
<213> ORGANISM: Homo sapiens

<400> SEQUENCE: 20

Cys Ser Cys Ser Ser Leu Met Asp Lys Glu Cys Val Tyr Phe Cys His
1               5                   10                  15

Leu Asp Ile Ile Trp Val Asn Thr Pro Glu His Val Val Pro Tyr Gly
            20                  25                  30

Leu Gly Ser Pro Arg Ser
        35

<210> SEQ ID NO 21
<211> LENGTH: 134
<212> TYPE: PRT
<213> ORGANISM: Homo sapiens

<400> SEQUENCE: 21

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80
```

```
Glu Val Ala Thr Glu Gly Ile Arg Gly His Arg Lys Met Val Leu Tyr
                85                  90                  95
Thr Leu Arg Ala Pro Arg Ser Pro Lys Met Val Gln Gly Ser Gly Cys
            100                 105                 110
Phe Gly Arg Lys Met Asp Arg Ile Ser Ser Ser Gly Leu Gly Cys
        115                 120                 125
Lys Val Leu Arg Arg His
    130

<210> SEQ ID NO 22
<211> LENGTH: 108
<212> TYPE: PRT
<213> ORGANISM: Homo sapiens

<400> SEQUENCE: 22

His Pro Leu Gly Ser Pro Gly Ser Ala Ser Asp Leu Glu Thr Ser Gly
1               5                   10                  15
Leu Gln Glu Gln Arg Asn His Leu Gln Gly Lys Leu Ser Glu Leu Gln
            20                  25                  30
Val Glu Gln Thr Ser Leu Glu Pro Leu Gln Glu Ser Pro Arg Pro Thr
        35                  40                  45
Gly Val Trp Lys Ser Arg Glu Val Ala Thr Glu Gly Ile Arg Gly His
    50                  55                  60
Arg Lys Met Val Leu Tyr Thr Leu Arg Ala Pro Arg Ser Pro Lys Met
65                  70                  75                  80
Val Gln Gly Ser Gly Cys Phe Gly Arg Lys Met Asp Arg Ile Ser Ser
                85                  90                  95
Ser Ser Gly Leu Gly Cys Lys Val Leu Arg Arg His
            100                 105

<210> SEQ ID NO 23
<211> LENGTH: 76
<212> TYPE: PRT
<213> ORGANISM: Homo sapiens

<400> SEQUENCE: 23

His Pro Leu Gly Ser Pro Gly Ser Ala Ser Asp Leu Glu Thr Ser Gly
1               5                   10                  15
Leu Gln Glu Gln Arg Asn His Leu Gln Gly Lys Leu Ser Glu Leu Gln
            20                  25                  30
Val Glu Gln Thr Ser Leu Glu Pro Leu Gln Glu Ser Pro Arg Pro Thr
        35                  40                  45
Gly Val Trp Lys Ser Arg Glu Val Ala Thr Glu Gly Ile Arg Gly His
    50                  55                  60
Arg Lys Met Val Leu Tyr Thr Leu Arg Ala Pro Arg
65                  70                  75

<210> SEQ ID NO 24
<211> LENGTH: 32
<212> TYPE: PRT
<213> ORGANISM: Homo sapiens

<400> SEQUENCE: 24

Ser Pro Lys Met Val Gln Gly Ser Gly Cys Phe Gly Arg Lys Met Asp
1               5                   10                  15
Arg Ile Ser Ser Ser Gly Leu Gly Cys Lys Val Leu Arg Arg His
            20                  25                  30
```